United States Patent
Lanza et al.

(10) Patent No.: US 11,566,228 B2
(45) Date of Patent: *Jan. 31, 2023

(54) HEMANGIO-COLONY FORMING CELLS

(71) Applicant: Astellas Institute for Regenerative Medicine, Marlborough, MA (US)

(72) Inventors: Robert Lanza, Clinton, MA (US); Shi-Jiang Lu, Shrewsbury, MA (US)

(73) Assignee: Astellas Institute for Regenerative Medicine, Westborough, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/902,817

(22) Filed: Feb. 22, 2018

(65) Prior Publication Data

US 2019/0017027 A1 Jan. 17, 2019

Related U.S. Application Data

(63) Continuation of application No. 14/869,561, filed on Sep. 29, 2015, now Pat. No. 9,938,500, which is a continuation of application No. 13/190,988, filed on Jul. 26, 2011, now abandoned, which is a continuation of application No. 11/787,262, filed on Apr. 13, 2007, now Pat. No. 8,017,393.

(60) Provisional application No. 60/918,832, filed on Mar. 19, 2007, provisional application No. 60/860,676, filed on Nov. 22, 2006, provisional application No. 60/852,142, filed on Oct. 16, 2006, provisional application No. 60/846,163, filed on Sep. 20, 2006, provisional application No. 60/801,993, filed on May 19, 2006, provisional application No. 60/792,224, filed on Apr. 14, 2006.

(51) Int. Cl.
- *C12N 5/0789* (2010.01)
- *A61K 35/44* (2015.01)
- *A61K 35/12* (2015.01)

(52) U.S. Cl.
CPC ............ *C12N 5/0647* (2013.01); *A61K 35/44* (2013.01); *A61K 2035/124* (2013.01); *C12N 2500/90* (2013.01); *C12N 2500/99* (2013.01); *C12N 2501/115* (2013.01); *C12N 2501/125* (2013.01); *C12N 2501/145* (2013.01); *C12N 2501/155* (2013.01); *C12N 2501/165* (2013.01); *C12N 2501/20* (2013.01); *C12N 2501/26* (2013.01); *C12N 2501/998* (2013.01); *C12N 2506/02* (2013.01)

(58) Field of Classification Search
None
See application file for complete search history.

(56) References Cited

U.S. PATENT DOCUMENTS

| 5,128,259 | A  | 7/1992  | Morgan et al. |
|-----------|----|---------|---------------|
| 5,599,705 | A  | 2/1997  | Cameron |
| 5,635,387 | A  | 6/1997  | Fei et al. |
| 5,914,268 | A  | 6/1999  | Keller et al. |
| 6,429,012 | B1 | 8/2002  | Kraus et al. |
| 6,479,286 | B1 | 11/2002 | Nelson et al. |
| 6,602,711 | B1 | 8/2003  | Thomson et al. |
| 7,153,684 | B1 | 12/2006 | Hogan |
| 7,220,584 | B2 | 5/2007  | Thomson et al. |
| 7,294,510 | B2 | 11/2007 | Okano et al. |
| 7,374,934 | B2 | 5/2008  | Keller et al. |
| 7,592,176 | B2 | 9/2009  | Pike et al. |
| 7,615,374 | B2 | 11/2009 | Vodyanyk et al. |
| 7,795,026 | B2 | 9/2010  | Shamblott et al. |
| 7,947,499 | B2 | 5/2011  | Gerecht-Nir et al. |
| 8,017,393 | B2 | 9/2011  | Lanza et al. |
| 8,148,152 | B2 | 4/2012  | Kolossov et al. |
| 8,343,762 | B2 | 1/2013  | Itskovitz-Eldor et al. |
| 8,354,277 | B2 | 1/2013  | Amit et al. |
| 8,372,642 | B2 | 2/2013  | Rajesh et al. |
| 8,492,148 | B2 | 7/2013  | Asahara et al. |
| 8,501,474 | B2 | 8/2013  | Yirme et al. |
| 8,822,218 | B2 | 9/2014  | Kimbrel et al. |
| 8,956,867 | B2 | 2/2015  | Kamp et al. |
| 8,962,318 | B2 | 2/2015  | Lim et al. |
| 8,962,321 | B2 | 2/2015  | Kimbrel et al. |
| 8,986,996 | B2 | 3/2015  | Cho et al. |
| 9,018,005 | B2 | 4/2015  | Lim et al. |
| 9,029,146 | B2 | 5/2015  | Lim et al. |
| 9,109,202 | B2 | 8/2015  | Spanholtz |
| 9,121,008 | B2 | 9/2015  | Tsai |

(Continued)

FOREIGN PATENT DOCUMENTS

| AU | 2009244231 A1 | 11/2009 |
| AU | 2009244236 A1 | 11/2009 |

(Continued)

OTHER PUBLICATIONS

Tian et al, Experimental Hematology, 2004, vol. 32, pp. 1000-1009. (Year: 2004).*

(Continued)

*Primary Examiner* — Allison M Fox
(74) *Attorney, Agent, or Firm* — McCarter & English, LLP; Maria Laccotripe Zacharakis

(57) ABSTRACT

Methods of generating and expanding human hemangio-colony forming cells in vitro and methods of expanding and using such cells are disclosed. The methods permit the production of large numbers of hemangio-colony forming cells as well as derivative cells, such as hematopoietic and endothelial cells. The cells obtained by the methods disclosed may be used for a variety of research, clinical, and therapeutic applications.

20 Claims, 30 Drawing Sheets

Specification includes a Sequence Listing.

(56) References Cited

U.S. PATENT DOCUMENTS

| | | |
|---|---|---|
| 9,206,392 B2 | 12/2015 | Amit et al. |
| 9,388,384 B2 | 7/2016 | Kim et al. |
| 9,410,123 B2 | 8/2016 | Lanza et al. |
| 9,458,425 B1 | 10/2016 | Itskovitz-Eldor et al. |
| 9,598,675 B2 | 3/2017 | Shim et al. |
| 9,655,925 B2 | 5/2017 | Lowdell |
| 9,725,698 B2 | 8/2017 | Wang et al. |
| 9,745,551 B2 | 8/2017 | Wang et al. |
| 9,938,499 B2 | 4/2018 | Slukvin et al. |
| 9,938,500 B2 | 4/2018 | Lanza et al. |
| 9,988,602 B2 | 6/2018 | Lanza et al. |
| 9,988,603 B2 | 6/2018 | Li et al. |
| 10,226,488 B2 | 3/2019 | Wang et al. |
| 10,557,122 B2 | 2/2020 | Wang et al. |
| 10,597,635 B2 | 3/2020 | Amit et al. |
| 2002/0035735 A1 | 3/2002 | Schatten et al. |
| 2003/0166273 A1 | 9/2003 | Kaufman et al. |
| 2003/0175954 A1 | 9/2003 | Shamblott et al. |
| 2004/0013676 A1 | 1/2004 | Bae et al. |
| 2004/0052771 A1 | 3/2004 | Lim |
| 2004/0096967 A1 | 5/2004 | Gryseels et al. |
| 2004/0229350 A1 | 11/2004 | Strelchenko et al. |
| 2005/0032210 A1 | 2/2005 | Sato et al. |
| 2005/0042751 A1 | 2/2005 | Goldman et al. |
| 2005/0054100 A1 | 3/2005 | Rennard et al. |
| 2005/0153443 A1 | 7/2005 | Lanza et al. |
| 2005/0176142 A1 | 8/2005 | Nakorn et al. |
| 2005/0221482 A1 | 10/2005 | Burt |
| 2005/0221487 A1 | 10/2005 | Zon et al. |
| 2006/0099198 A1 | 5/2006 | Thomson et al. |
| 2007/0042344 A1 | 2/2007 | Choi et al. |
| 2007/0053885 A1 | 3/2007 | Nishikawa et al. |
| 2007/0128727 A1 | 6/2007 | Kraemer et al. |
| 2007/0141703 A1 | 6/2007 | Stanley et al. |
| 2007/0218552 A1 | 9/2007 | Giarratana et al. |
| 2007/0298496 A1 | 12/2007 | Kuo et al. |
| 2008/0003674 A1 | 1/2008 | Slukvin et al. |
| 2008/0014180 A1 | 1/2008 | Lanza et al. |
| 2008/0014183 A1 | 1/2008 | Okano et al. |
| 2008/0026460 A1 | 1/2008 | Palecek et al. |
| 2008/0057041 A1 | 3/2008 | Chung et al. |
| 2008/0081370 A1 | 4/2008 | Hematti et al. |
| 2008/0108044 A1 | 5/2008 | Rajesh et al. |
| 2008/0160564 A1 | 7/2008 | Rich |
| 2008/0166327 A1 | 7/2008 | Asahara et al. |
| 2008/0166751 A1 | 7/2008 | Asahara et al. |
| 2009/0239298 A1 | 9/2009 | Gerecht et al. |
| 2009/0246875 A1 | 10/2009 | Yamanaka et al. |
| 2009/0304646 A1 | 12/2009 | Sakurada et al. |
| 2010/0184212 A1 | 7/2010 | Stice et al. |
| 2010/0233135 A1 | 9/2010 | Arnaout |
| 2011/0053267 A1 | 3/2011 | Nakauchi et al. |
| 2011/0064705 A1 | 3/2011 | Lanza et al. |
| 2011/0086424 A1 | 4/2011 | Lanza et al. |
| 2011/0151554 A1 | 6/2011 | Yuo et al. |
| 2012/0003738 A1 | 1/2012 | Costa et al. |
| 2012/0027731 A1 | 2/2012 | Lanza et al. |
| 2012/0238020 A1 | 9/2012 | Mitchell et al. |
| 2013/0004464 A1 | 1/2013 | Nadal-Ginard |
| 2013/0084267 A1 | 4/2013 | Fisk et al. |
| 2014/0271616 A1 | 9/2014 | Nejadnik et al. |
| 2015/0140657 A1 | 5/2015 | Kimbrel et al. |
| 2016/0011545 A1 | 1/2016 | Lanza et al. |
| 2017/0121681 A1 | 5/2017 | Lanza et al. |
| 2017/0152481 A1 | 6/2017 | Lanza et al. |
| 2017/0342384 A1 | 11/2017 | Dar-Oaknin et al. |
| 2019/0002828 A1 | 1/2019 | Lanza et al. |
| 2019/0002829 A1 | 1/2019 | Li et al. |
| 2019/0071637 A1 | 3/2019 | Slukvin et al. |
| 2019/0112573 A1 | 4/2019 | Xu et al. |
| 2019/0161726 A1 | 5/2019 | Komazawa et al. |
| 2019/0167733 A1 | 6/2019 | Wang et al. |
| 2020/0080059 A1 | 3/2020 | Thomson et al. |
| 2020/0131475 A1 | 4/2020 | Kimbrel et al. |
| 2020/0157503 A1 | 5/2020 | Lanza et al. |
| 2020/0263132 A1 | 8/2020 | Lanza et al. |

FOREIGN PATENT DOCUMENTS

| | | |
|---|---|---|
| AU | 2013201444 A1 | 3/2013 |
| CN | 1556197 A | 12/2004 |
| CN | 101045914 A | 10/2007 |
| CN | 101045915 A | 10/2007 |
| CN | 101052710 A | 10/2007 |
| CN | 101528915 A | 9/2009 |
| CN | 101981181 A | 2/2011 |
| CN | 102083960 A | 6/2011 |
| CN | 102083963 A | 6/2011 |
| CN | 102660495 A | 9/2012 |
| CN | 102822332 A | 12/2012 |
| CN | ZL200980125862 | 12/2014 |
| CN | 104328087 A | 2/2015 |
| CN | 106434527 A | 2/2017 |
| EP | 1644486 A2 | 4/2006 |
| EP | 2013331 A2 | 1/2009 |
| EP | 2288690 A2 | 3/2011 |
| EP | 2291513 A2 | 3/2011 |
| EP | 2377923 A1 | 10/2011 |
| EP | 2377924 A1 | 10/2011 |
| EP | 2377925 A1 | 10/2011 |
| EP | 2426197 A1 | 3/2012 |
| EP | 2495311 A1 | 9/2012 |
| EP | 2507359 A1 | 10/2012 |
| EP | 2507365 A1 | 10/2012 |
| EP | 2712921 A1 | 4/2014 |
| EP | 2872619 A2 | 5/2015 |
| EP | 2970912 A1 | 1/2016 |
| EP | 3020405 A1 | 5/2016 |
| EP | 3492577 A1 | 6/2019 |
| JP | 2002-515756 A | 5/2002 |
| JP | 2004-504834 A | 2/2004 |
| JP | 2004-531262 A | 10/2004 |
| JP | 2004-535389 A | 11/2004 |
| JP | 2005-511084 A | 4/2005 |
| JP | 2007-89432 A | 4/2007 |
| JP | 2008-535493 A | 9/2008 |
| JP | 2009-533059 A | 9/2009 |
| JP | 2011-519576 A | 7/2011 |
| JP | 2011-519577 A | 7/2011 |
| JP | 2013-512673 A | 4/2013 |
| JP | 2013-512676 A | 4/2013 |
| JP | 2013-126423 A | 6/2013 |
| JP | 5630781 B2 | 11/2014 |
| JP | 2015-57070 A | 3/2015 |
| JP | 2015-61539 A | 4/2015 |
| JP | 5748654 B2 | 7/2015 |
| JP | 2016-63838 A | 4/2016 |
| NZ | 518191 A | 1/2004 |
| NZ | 572842 A | 1/2012 |
| WO | WO-1995/17500 A1 | 6/1995 |
| WO | WO-1999/67360 A2 | 12/1999 |
| WO | WO-2000/11139 A1 | 3/2000 |
| WO | WO-2001/036589 A2 | 5/2001 |
| WO | 2002/089730 A2 | 11/2002 |
| WO | WO-2003/046141 A2 | 6/2003 |
| WO | WO-2003/050251 A2 | 6/2003 |
| WO | WO-2004/007698 A1 | 1/2004 |
| WO | WO-2004/029231 A1 | 4/2004 |
| WO | WO-2004/044146 A2 | 5/2004 |
| WO | WO-2005/040391 A1 | 5/2005 |
| WO | WO-2005/049812 A1 | 6/2005 |
| WO | WO-2005/078073 A2 | 8/2005 |
| WO | WO-2005/118780 A1 | 12/2005 |
| WO | 2006/001954 A2 | 1/2006 |
| WO | WO-2006/050330 A2 | 5/2006 |
| WO | WO-2006/090882 A1 | 8/2006 |
| WO | WO-2006/130651 A2 | 12/2006 |
| WO | WO-2007/005595 A1 | 1/2007 |
| WO | WO-2007/032634 A1 | 3/2007 |
| WO | WO-2007/037682 A1 | 4/2007 |
| WO | WO-2007/095064 A2 | 8/2007 |
| WO | WO-2007/120811 A2 | 10/2007 |

(56) References Cited

FOREIGN PATENT DOCUMENTS

| | | |
|---|---|---|
| WO | 2007/122233 A1 | 11/2007 |
| WO | WO-2008/058779 A1 | 5/2008 |
| WO | 2008/151390 A1 | 12/2008 |
| WO | WO-2008/151386 A1 | 12/2008 |
| WO | WO-2009/045360 A2 | 4/2009 |
| WO | WO-2009/052389 A1 | 4/2009 |
| WO | WO-2009/104825 A1 | 8/2009 |
| WO | 2009/119105 A1 | 10/2009 |
| WO | 2009/122747 A1 | 10/2009 |
| WO | WO-2009/137624 A2 | 11/2009 |
| WO | WO-2009/137629 A2 | 11/2009 |
| WO | WO-2010/025506 A1 | 3/2010 |
| WO | 2011/025179 A2 | 3/2011 |
| WO | 2011/026221 A1 | 3/2011 |
| WO | WO-2011/068896 A1 | 6/2011 |
| WO | WO-2011/069127 A1 | 6/2011 |
| WO | 2013/108949 A1 | 7/2013 |
| WO | 2014/138485 A1 | 9/2014 |
| WO | 2014/146057 A2 | 9/2014 |
| WO | 2015/179301 A1 | 11/2015 |
| WO | 2015/191632 A1 | 12/2015 |
| WO | 2016/160860 A1 | 10/2016 |
| WO | 2019/213366 A1 | 11/2019 |

OTHER PUBLICATIONS

Wang et al, Immunity, 2004, vol. 21, pp. 31-41. (Year: 2004).*

Xiong et al, Developmental Dynamics, 2008, vol. 237, pp. 1218-1231. (Year: 2008).*

Zambidis et al, Blood, 2005, vol. 106, pp. 860-870. (Year: 2005).*

Dang et al, Biotechnology and Bioengineering, 2002, vol. 78, No. 4, pp. 442-453. (Year: 2002).*

Alikani et al., Nonviable human pre-implantation embryos as a source of stem cells for research and potential therapy. Stem Cell Rev. Dec. 2005;1(4):337-43.

Baek et al., Stroma-free mass production of clinical-grade red blood cells (RBCs) by using poloxamer 188 as an RBC survival enhancer. Transfusion. Nov. 2009;49(11):2285-95.

Bagamery et al., Are platelets activated after a rapid, one-step density gradient centrifugation? Evidence from flow cytometric analysis. Clin Lab Haematol. Feb. 2005;27(1):75-7.

Bhatia, Hematopoiesis from human embryonic stem cells. Ann N Y Acad Sci. Jun. 2007;1106:219-22.

Bordoni et al., Hepatocyte-conditioned medium sustains endothelial differentiation of human hematopoietic-endothelial progenitors. Hepatology. May 2007;45(5):1218-28.

Bowles et al., HOXB4 overexpression promotes hematopoietic development by human embryonic stem cells. Stem Cells. May 2006;24(5):1359-69.

Cerdan et al., Hematopoietic Differentiation. Embryonic Stem Cells. J.R. Masters (Ed.). Chapter 5, pp. 53-83, (2007).

Chan-Ling et al., Hematopoietic stem cells provide repair functions after laser-induced Bruch's membrane rupture model of choroidal neovascularization. Am J Pathol. Mar. 2006;168(3):1031-44.

Cheng et al., Human mesenchymal stem cells support megakaryocyte and pro-platelet formation from CD34(+) hematopoietic progenitor cells. J Cell Physiol. Jul. 2000;184(1):58-69.

Choi et al., A common precursor for hematopoietic and endothelial cells. Development. Feb. 1998;125(4):725-32.

Choi et al., In vitro development of a hemangioblast from a human embryonic stem cell, SNUhES#3. Life Sci. Jul. 3, 2009;85(1-2):39-45.

Chun et al.. Megakaryocyte Production from Feeder Cell-Free Cultures of Human Embryonic Stem Cells (hESC). Blood, 2009;114:Abstract 2528.

Cibelli et al., Parthenogenetic stem cells in nonhuman primates. Science. Feb. 1, 2002;295(5556):819.

Cibelli et al., Somatic Cell Nuclear Transfer in Humans: Pronuclear and Early Embryonic Development. ebiomed: The Journal of Regenerative Medicine. Nov. 26, 2001;2(5):25-31.

Dolzhanskiy et al., The development of human megakaryocytes: III. Development of mature megakaryocytes from highly purified committed progenitors in synthetic culture media and inhibition of thrombopoietin-induced polyploidization by interleukin-3. Blood. Jan. 15, 1997;89(2):426-34.

Dore et al., Transcription factor networks in erythroid cell and megakaryocyte development. Blood. Jul. 14, 2011;118(2):231-9.

Douay et al., Stem cells—a source of adult red blood cells for transfusion purposes: present and future. Crit Care Clin. Apr. 2009;25(2):383-98.

Fedele et al., CD38 is expressed on human mature monocyte-derived dendritic cells and is functionally involved in CD83 expression and IL-12 induction. Eur J Immunol. May 2004;34(5):1342-50.

Fujimoto et al., Production of functional platelets by differentiated embryonic stem (ES) cells in vitro. Blood. Dec. 1, 2003;102(12):4044-51.

Geens et al., Human embryonic stem cell lines derived from single blastomeres of two 4-cell stage embryos. Hum Reprod. Nov. 2009;24(11):2709-17.

Giarratana et al., Ex vivo generation of fully mature human red blood cells from hematopoietic stem cells. Nat Biotechnol. Jan. 2005;23(1):69-74.

Grant et al., Adult hematopoietic stem cells provide functional hemangioblast activity during retinal neovascularization. Nat Med. Jun. 2002;8(6):607-12.

Guo et al., Hemangioblastic characteristics of fetal bone marrow-derived Flk1(+)CD31(-)CD34(-) cells. Exp Hematol. Jul. 2003;31(7):650-8.

Hematti et al., Nonhuman primate embryonic stem cells as a preclinical model for hematopoietic and vascular repair. Exp Hematol. Sep. 2005;33(9):980-6.

Hiroyama et al., Establishment of mouse embryonic stem cell-derived erythroid progenitor cell lines able to produce functional red blood cells. PLoS One. Feb. 6, 2008;3(2):e1544, 11 pages.

Huangfu et al., Induction of pluripotent stem cells from primary human fibroblasts with only Oct4 and Sox2. Nat Biotechnol. Nov. 2008;26(11):1269-75.

Ireland, Visualizing Human Biology, Third Edition. Wiley and Sons Inc., p. 527, (2008).

Jarnjak-Jankovic et al., A full scale comparative study of methods for generation of functional Dendritic cells for use as cancer vaccines. BMC Cancer. Jul. 3, 2007;7:119. 9 pages.

Kaufman et al., Hematopoietic colony-forming cells derived from human embryonic stem cells. Proc Natl Acad Sci U S A. Sep. 11, 2001;98(19):10716-21.

Kennedy et al., Development of the hemangioblast defines the onset of hematopoiesis in human ES cell differentiation cultures. Blood. Apr. 1, 2007;109(7):2679-87.

Klimanskaya et al., Approaches for Derivation and Maintenance of Human Embryonic Stem Cells: Detailed Procedures and Alternatives. Essentials of Stem Cell Biology, Third Edition. Academic Press. Chapter 29, pp. 409-434, (2014).

Klimanskaya et al., Approaches for Derivation and Maintenance of Human ES Cells: Detailed Procedures and Alternatives. Handbook of Stem Cells. Elsevier Academic Press, Amsterdam. vol. 1, Embryonic Stem Cells. Robert Lanza (Ed). Chapter 41, pp. 437-449, (2004).

Lechmann et al., CD83 on dendritic cells: more than just a marker for maturation. Trends Immunol. Jun. 2002;23(6):273-5.

Li et al., In vitro differentiation into megakaryocytes and generation of platelets from CD34+ cells of umbilical cord blood. Zhong Nan Da Xue Xue Bao Yi Xue Ban. Oct. 2006;31(5):776-81.

Li et al., Large Scale Generation of Functional Megakaryocyties from Human Embryonic Stem Cells (hESCs) Under Stromal-Free Conditions. Blood, ASH Annual Meeting. 2009;114:Abstract 2540.

Life technologies, Guidelines for Maintaining Cultured Cells. Retrieved online at: https://www.lifetechnologies.com/us/en/home/references/gibco-cell-culture-basics/cell-culture-protocols/maintaining-cultured-cells.html. 4 pages, (2014).

Lin et al., Multilineage potential of homozygous stem cells derived from metaphase II oocytes. Stem Cells. 2003;21(2):152-61.

Loges et al., Identification of the adult human hemangioblast. Stem Cells Dev. Jun. 2004;13(3):229-42.

(56) References Cited

OTHER PUBLICATIONS

Lowry et al., Generation of human induced pluripotent stem cells from dermal fibroblasts. Proc Natl Acad Sci U S A. Feb. 26, 2008;105(8):2883-8.
Lu et al., Biologic properties and enucleation of red blood cells from human embryonic stem cells. Blood. Dec. 1, 2008;112(12):4475-84.
Lu et al., GeneChip analysis of human embryonic stem cell differentiation into hemangioblasts: an in silico dissection of mixed phenotypes. Genome Biol. 2007;8(11):R240, 19 pages.
Lu et al., Generation of functional hemangioblasts from human embryonic stem cells. Nat Methods. Jun. 2007;4(6):501-9.
Lu et al., Hemangioblasts from human embryonic stem cells generate multilayered blood vessels with functional smooth muscle cells. Regen Med. Jan. 2009;4(1):37-47.
Lu et al., Protocol for culturing, differentiating and expanding hES-BC cells. Supplemental Protocol. Nature Methods. 2007;4:1-3.
Lu et al., Recombinant HoxB4 fusion proteins enhance hematopoietic differentiation of human embryonic stem cells. Stem Cells Dev. Aug. 2007;16(4):547-59.
Lu et al., Robust generation of hemangioblastic progenitors from human embryonic stem cells. Regen Med. Sep. 2008;3(5):693-704.
Ma et al., Generation of functional erythrocytes from human embryonic stem cell-derived definitive hematopoiesis. Proc Natl Acad Sci U S A. Sep. 2, 2008;105(35):13087-92.
Ma et al., Novel method for efficient production of multipotential hematopoietic progenitors from human embryonic stem cells. Int J Hematol. Jun. 2007;85(5):371-9.
Maherali et al., Guidelines and techniques for the generation of induced pluripotent stem cells. Cell Stem Cell. Dec. 4, 2008;3(6):595-605.
Matsumoto et al., Stepwise development of hematopoietic stem cells from embryonic stem cells. PLoS One. 2009;4(3):e4820, 10 pages.
Mercher et al., Notch signaling specifies megakaryocyte development from hematopoietic stem cells. Cell Stem Cell. Sep. 11, 2008;3(3):314-26.
Mitalipova et al., Human embryonic stem cell lines derived from discarded embryos. Stem Cells. 2003;21(5):521-6.
Nakamura, In vitro production of transfusable red blood cells. Biotechnol Genet Eng Rev. 2008;25:187-201.
Neildez-Nguyen et al., Human erythroid cells produced ex vivo at large scale differentiate into red blood cells in vivo. Nat Biotechnol. May 2002;20(5):467-72.
Nih, Stem Cells: Scientific Progress and Future Research Directions. National Institutes of Health, Department of Health and Human Services. pp. 1-4, Jun. 2001.
Nishikii et al., Metalloproteinase regulation improves in vitro generation of efficacious platelets from mouse embryonic stem cells. J Exp Med. Aug. 4, 2008;205(8):1917-27.
Olivier et al., Large-scale production of embryonic red blood cells from human embryonic stem cells. Exp Hematol. Dec. 2006;34(12):1635-42.
Ozawa et al., Erythroid cells play essential roles in angiogenesis by bone marrow cell implantation. J Mol Cell Cardiol. May 2006;40(5):629-38.
Park et al., Reprogramming of human somatic cells to pluripotency with defined factors. Nature. Jan. 10, 2008;451(7175):141-7.
Passegue et al., Normal and leukemic hematopoiesis: are leukemias a stem cell disorder or a reacquisition of stem cell characteristics? Proc Natl Acad Sci U S A. Sep. 30, 2003;100 Suppl 1:11842-9.
Pearson et al., The stepwise specification of embryonic stem cells to hematopoietic fate is driven by sequential exposure to Bmp4, activin A, bFGF and VEGF. Development. Apr. 2008;135(8):1525-35.
Pick et al., Differentiation of human embryonic stem cells in serum-free medium reveals distinct roles for bone morphogenetic protein 4, vascular endothelial growth factor, stem cell factor, and fibroblast growth factor 2 in hematopoiesis. Stem Cells. Sep. 2007;25(9):2206-14.
Pilat et al., HOXB4 enforces equivalent fates of ES-cell-derived and adult hematopoietic cells. Proc Natl Acad Sci U S A. Aug. 23, 2005;102(34):12101-6.
Purpura et al., Analysis of the temporal and concentration-dependent effects of BMP-4, VEGF, and TPO on development of embryonic stem cell-derived mesoderm and blood progenitors in a defined, serum-free media. Exp Hematol. Sep. 2008;36(9):1186-98.
Qiu et al., Globin switches in yolk sac-like primitive and fetal-like definitive red blood cells produced from human embryonic stem cells. Blood. Feb. 15, 2008;111(4):2400-8.
Rajesh et al., Differential requirements for hematopoietic commitment between human and rhesus embryonic stem cells. Stem Cells. Feb. 2007;25(2):490-9.
Reems et al., In vitro megakaryocyte production and platelet biogenesis: state of the art. Transfus Med Rev. Jan. 2010;24(1):33-43.
Reijo Pera et al., Gene expression profiles of human inner cell mass cells and embryonic stem cells. Differentiation. Jul. 2009;78(1):18-23.
Reubinoff et al., Embryonic stem cell lines from human blastocysts: somatic differentiation in vitro. Nat Biotechnol. Apr. 2000;18(4):399-404.
Revazova et al., Patient-specific stem cell lines derived from human parthenogenetic blastocysts. Cloning Stem Cells. 2007 Fall;9(3):432-49.
Rogers et al., Phospholipase Czeta causes Ca2+ oscillations and parthenogenetic activation of human oocytes. Reproduction. Dec. 2004;128(6):697-702.
Sauvageau et al., Overexpression of HOXB4 in hematopoietic cells causes the selective expansion of more primitive populations in vitro and in vivo. Genes Dev. Jul. 15, 1995;9(14):1753-65.
Schenke-Layland et al., Reprogrammed mouse fibroblasts differentiate into cells of the cardiovascular and hematopoietic lineages. Stem Cells. Jun. 2008;26(6):1537-46.
Seliger et al., Chemical production of excited states. Chemiluminescence of carcinogenic hydrocarbons accompanying their metabolic hydroxylation and a proposal for common active site geometries for hydroxylation. J Phys Chem. Sep. 1, 1976;80(20):2296-306.
Senger, Pathways to Pregnancy and Parturition. Current Conceptions, Inc., Pullman, WA. Chapter 13, pp. 221-222, (1997).
Shinoda et al., alpha4-Integrin(+) endothelium derived from primate embryonic stem cells generates primitive and definitive hematopoietic cells. Blood. Mar. 15, 2007;109(6):2406-15.
Springer et al., VEGF gene delivery to muscle: potential role for vasculogenesis in adults. Mol Cell. Nov. 1998;2(5):549-58.
Svingen et al., Hox transcription factors and their elusive mammalian gene targets. Heredity (Edinb). Aug. 2006;97(2):88-96.
Takahashi et al., Induction of pluripotent stem cells from adult human fibroblasts by defined factors. Cell. Nov. 30, 2007;131(5):861-72.
Takayama et al., Generation of functional platelets from human embryonic stem cells in vitro via ES-sacs, VEGF-promoted structures that concentrate hematopoietic progenitors. Blood. Jun. 1, 2008;111(11):5298-306.
Tober et al., The megakaryocyte lineage originates from hemangioblast precursors and is an integral component both of primitive and of definitive hematopoiesis. Blood. Feb. 15, 2007;109(4):1433-41.
Tseng et al., Generation of immunogenic dendritic cells from human embryonic stem cells without serum and feeder cells. Regen Med. Jul. 2009;4(4):513-26.
Ucla, Induced Pluripotent Stem Cells (iPS). Retrieved online at: https://stemcell.ucla.edu/induced-pluripotent-stem-cells. 2 pages, (2016).
Umeda et al., Development of primitive and definitive hematopoiesis from nonhuman primate embryonic stem cells in vitro. Development. Apr. 2004;131(8):1869-79.
Van De Velde et al., The four blastomeres of a 4-cell stage human embryo are able to develop individually into blastocysts with inner cell mass and trophectoderm. Hum Reprod. Aug. 2008;23(8):1742-7.
Verfaillie et al., Kinetics of engraftment of CD34(−) and CD34(+) cells from mobilized blood differs from that of CD34(−) and CD34(+) cells from bone marrow. Exp Hematol. Sep. 2000;28(9):1071-9.

(56) References Cited

OTHER PUBLICATIONS

Vodyanik et al., Human embryonic stem cell-derived CD34+ cells: efficient production in the coculture with OP9 stromal cells and analysis of lymphohematopoietic potential. Blood. Jan. 15, 2005;105(2):617-26.
Wang, Endothelial and hematopoietic cell fate of human embryonic stem cells. Trends Cardiovasc Med. Apr. 2006;16(3):89-94.
Watanabe et al., A ROCK inhibitor permits survival of dissociated human embryonic stem cells. Nat Biotechnol. Jun. 2007;25(6):681-6.
Wernig et al., In vitro reprogramming of fibroblasts into a pluripotent ES-cell-like state. Nature. Jul. 19, 2007;448(7151):318-24. Supplemental Materials, 1 page.
Woll et al., Human embryonic stem cell-derived NK cells acquire functional receptors and cytolytic activity. J Immunol. Oct. 15, 2005;175(8):5095-103.
Woll et al., Human embryonic stem cells differentiate into a homogeneous population of natural killer cells with potent in vivo antitumor activity. Blood. Jun. 11, 2009;113(24):6094-101.
Yu et al., Pluripotent stem cell lines. Genes Dev. Aug. 1, 2008;22(15):1987-97.
Yuan et al., Stem cell science on the rise in China. Cell Stem Cell. Jan. 6, 2012;10(1):12-5.
Zambidis et al., Expression of angiotensin-converting enzyme (CD143) identifies and regulates primitive hemangioblasts derived from human pluripotent stem cells. Blood. Nov. 1, 2008;112(9):3601-14.
Zhao et al., Effect of different hemopoietic microenvironment on the differentiation of hemopoietic cells from human embryonic stem cells. Zhong Nan Da Xue Xue Bao Yi Xue Ban. Dec. 2007;32(6):992-6.
Zwaka, Use of Genetically Modified Stem Cells in Experimental Gene Therapies. Stem Cell Information. NIH, National Institutes of Health, retrieved online at: https://web.archive.org/web/20171029014802/https://stemcells.nih.gov/info/Regenerative_Medicine/2006Chapter4.htm. Chapter 4, (2016).
Australian Examination Report for Application No. 2007238660, dated Mar. 6, 2012.
Australian Office Action for Application No. 2007238660, dated Jan. 10, 2013.
Chinese Examination Report for Application No. 200780021822.6, dated Dec. 16, 2011.
Chinese Examination Report for Application No. 200780021822.6, dated Jul. 30, 2010.
Chinese Office Action for Application No. 200980125860.5, dated Jan. 17, 2012.
Chinese Office Action for Application No. 200980125862.4, dated Dec. 31, 2011.
Chinese Rejection Decision for Application No. 200780021822.6, dated Jul. 30, 2012.
Chinese Second Office Action for Application No. 200980125860.5, dated Dec. 25, 2012.
Chinese Second Office Action for Application No. 200980125862.4, dated Aug. 9, 2012.
Chinese Third Office Action for Application No. 200980125862.4, dated Jan. 7, 2013.
European Examination Report for Application No. 07755391.5, dated Apr. 1, 2011.
European Examination Report for Application No. 07755391.5, dated Jul. 5, 2010.
European Examination Report for Application No. 07755391.5, dated Mar. 2, 2009.
European Extended Search Report for Application No. 13180755.4, dated Mar. 3, 2014, 9 Pages.
European Office Action for Application No. 07755391.5, dated Nov. 27, 2012.
European Official Notification Telephone Conference for Application No. 07755391.5, dated Sep. 26, 2011.
European Search Report for Application No. 09743610.9 dated Jan. 26, 2012, 8 pages.
European Search Report for Application No. 09743615.8, dated Jan. 26, 2012.
European Search Report for Application No. 10835231.1, dated Apr. 14, 2015.
European Search Report for Application No. 11155399.6, dated Sep. 19, 2011.
European Search Report for Application No. 11155482.0, dated Feb. 6, 2012.
European Search Report for Application No. 11155495.2, dated Sep. 19, 2011.
European Search Report for Application No. 11155500.9, dated Sep. 19, 2011.
European Search Report for Application No. 17174456.8 EP, dated Nov. 24, 2017.
International Search Report and Written Opinion for Application No. PCT/US2007/009106, dated Dec. 19, 2007.
International Search Report and Written Opinion for Application No. PCT/US2009/043043, dated Sep. 22, 2009, 21 pages.
International Search Report and Written Opinion for Application No. PCT/US2009/043050, dated Oct. 6, 2009, 13 Pages.
International Search Report and Written Opinion for Application No. PCT/US2010/058593, dated Apr. 19, 2011, 12 pages.
International Search Report and Written Opinion for Application No. PCT/US2010/058990, dated Apr. 4, 2011.
Japanese Office Action for Application No. 2009-505494, dated Sep. 28, 2012.
Japanese Office Action for Application No. 2017-206725, dated Nov. 14, 2019, 13 pages.
Mexican Office Action for Application No. MX/a/2010/012088, dated Feb. 27, 2012.
Mexican Office Action for Application No. MX/a/2010/012088, dated Jul. 13, 2012.
Mexican Office Action for Application No. MX/a/2010/012089, dated Feb. 24, 2012.
Mexican Office Action for Application No. MX/a/2010/012089, dated Oct. 26, 2012.
New Zealand Examination Report for Application No. 572842, dated Jun. 24, 2011.
New Zealand Examination Report for Application No. 572842, dated Nov. 3, 2011.
New Zealand Examination Report for Application No. 572842, dated Oct. 17, 2011.
New Zealand Examination Report for Application No. 596761, dated Dec. 7, 2011.
New Zealand Notice of Allowance for Application No. 572842, dated Jan. 12, 2012.
New Zealand Office Action for Application No. 572842, dated May 31, 2010.
Supplemental European Search Report for Application No. 10835074.5, dated Dec. 17, 2013, 6 pages.
U.S. Non-Final Office Action for U.S. Appl. No. 11/787,262, dated Oct. 2, 2009.
U.S. Non-Final Office Action for U.S. Appl. No. 11/787,262, dated Sep. 2, 2010.
U.S. Non-Final Office Action for U.S. Appl. No. 12/991,096, dated Oct. 2, 2012.
U.S. Notice of Allowance for U.S. Appl. No. 11/787,262, dated Apr. 27, 2011.
U.S. Restriction Requirement for U.S. Appl. No. 11/787,262, dated May 4, 2010.
U.S. Restriction Requirement for U.S. Appl. No. 12/991,096, dated May 21, 2012.
U.S. Restriction Requirement for U.S. Appl. No. 12/991,111, dated Dec. 10, 2012.
Law et al.. Analysis of human megakaryocytic cells using dual-color immunofluorescence labeling. Cytometry. 2000;41(4):308-315.
Ledran et al., Efficient hematopoietic differentiation of human embryonic stem cells on stromal cells derived from nematopoietic niches. Cell Stem Cell. 2008;3(1):85-98.
Lordier et al., Megakaryocyte endomitosis is a failure of late cytokinesis related to defects in the contractile ring and Rho/Rock signaling. Blood. 2008; 112(8):3164-3174.

(56) References Cited

OTHER PUBLICATIONS

Lu et al., CD34+CD38- hematopoietic precursors derived from human embryonic stem cells exhibit an embryonic gene expression pattern. Blood. 2004; 103(11):4134-4141.
Lu et al., Platelets generated from human embryonic stem cells are functional in vitro and in the microcirculation of living mice. Cell Res 2011;21(3):530-545.
Matsunaga et al., Ex vivo large-scale generation of human platelets from cord blood CD34+ cells. Stem Cells. 2006;24(12):2877-2887.
Moreau et al., Large-scale production of megakaryocytes from human pluripotent stem cells by chemically defined forward programming. Nat Commun. 2016;7:11208.
Morikawa et al., BMP Sustains Embryonic Stem Cell Self-Renewal through Distinct Functions of Different Krüppel-like Factors. Stem Cell Reports. 2016;6(1):64-73.
Munoz et al., Conventional pluripotency markers are unspecific for bovine embryonic-derived cell-lines. Theriogenology. 2008;69(9):1159-1164.
Nagata et al., Proplatelet formation of megakaryocytes is triggered by autocrine-synthesized estradiol. Genes Dev. 2003;17(23):2864-2869.
Nakajima et al., Effect of Wf-536, a novel ROCK inhibitor, against metastasis of B16 melanoma. Cancer Chemother Pharmacol 2003;52(4):319-324.
Ott et al., BET bromodomain inhibition targets both c-Myc and IL7R in high-risk acute lymphoblastic leukemia. Blood. 2012;120(14):2843-2852.
Pang et al., Induction of human neuronal cells by defined transcription factors. Nature. 2011;476(7359):220-223.
Paris et al., Equine embryos and embryonic stem cells: defining reliable markers of pluripotency. Theriogenology. 2010;74(4):516-524.
Philipp et al., The effects of Mpl-ligand, interleukin-6 and interleukin-11 on megakaryocyte and platelet alpha-granule proteins. Thromb Haemost. 1998;80(6):968-975.
Piper et al., In vivo recovery of human platelets in severe combined immunodeficient mice as a measure of platelet damage. Transfusion. 2007;47(8): 1540-1549.
Qi et al., BMP4 supports self-renewal of embryonic stem cells by inhibiting mitogen-activated protein kinase pathways. Proc Natl Acad Sci U S A. 2004;101(16):6027-6032.
Qiu et al., Differentiation of human embryonic stem cells into hematopoietic cells by coculture with human fetal liver Cells recapitulates the globin switch that occurs early in development. Exp Hematol. 2005;33(12):1450-1458.
Rafii et al., Human ESC-derived hemogenic endothelial cells undergo distinct waves of endothelial to hematopoietic transition. Blood. 2013;121(5):770-780.
Robert et al., Glycoprotein Iba receptor instability is associated with loss of quality in platelets produced in culture. Stem Cells Dev. 2011;20(3):379-390.
Robert et al., Megakaryocyte and platelet production from human cord blood stem cells. Methods Mol Biol. 2012;788:219-247.
Sachs et al., In vivo thrombus formation in murine models. Circ Res. 2007;100(7):979-991.
Santoso et al.. The presence of messenger RNA for HLA class 1 in human platelets and its capability for protein biosynthesis. Br J Haematol. 1993;84(3):451-456.
Sasaki et al., The novel and specific Rho-kinase inhibitor (S)-(+)-2-methyl-1-[(4-methyl-5-isoquinoline)sulfonyl]-homopiperazine as a probing molecule for Rho-kinase-involved pathway. Pharmacol Ther. 2002;93(2-3):225-232.
Seiler et al., Experimental limitations using reprogrammed cells for hematopoietic differentiation. J Biomed Biotechnol. 2011;2011:895086.
Stasi et al., Thrombopoietic agents. Blood Rev. 2010;24(4-5):179-190.
Stroncek, Universal platelets: "A" change in dogma. Blood. Apr. 15, 2005;105(8):3008.
Sullenbarger et al., Prolonged continuous in vitro human platelet production using three-dimensional scaffolds. Exp Hematol. 2009;37(1):101-110.
Szabo et al., Direct conversion of human fibroblasts to multilineage blood progenitors [published correction appears in Nature. Aug. 2018;560(7719):E32] Nature 2010;468(7323):521-526.
Taguchi et al., Disparate effects of interleukin 11 and thrombopoietin on megakaryocytopoiesis in vitro. Cytokine. 2001;15(5):241-249.
Takayama et al., Pluripotent stem cells reveal the developmental biology of human megakaryocytes and provide a source of platelets for clinical application Cell Mol Life Sci. 2012;69(20):3419-3428.
Takayama et al., Transient activation of c-MYC expression is critical for efficient platelet generation from human induced pluripotent stem cells. J Exp Med 2010;207(13):2817-2830.
Takeuchi et al., Directed transdifferentiation of mouse mesoderm to heart tissue by defined factors. Nature. 2009;459(7247):708-711.
Tanaka et al., Stem cell factor enhances proliferation, but not maturation, of murine megakaryocytic progenitors in serum-free culture. Blood. 1992;80(7):1743-1749.
Thurlow et al., Analysis of human bone marrow with monoclonal antibodies. J Histochem Cytochem. 1985;33(12):1183-1189.
Tian et al., Differentiation of embryonic stem cells towards hematopoietic cells: progress and pitfalls. Curr Opin Hematol 2008;15(4):312-318.
Tijssen et al., Genome-wide analysis of simultaneous GATA1/2, RUNX1, FLI1, and SCL binding in megakaryocytes identifies hematopoietic regulators. Dev Cell. 2011;20(5):597-609.
Tsuji et al., Novel approach for formation of platelet-like particles from mouse embryonic stem cells without using feeder cells. Kurume Med J. 2009;56(3-4):61-69.
Valtieri et al., Enforced TAL-1 expression stimulates primitive, erythroid and megakaryocytic progenitors but blocks the granulopoietic differentiation program. Cancer Res. 1998;58(3):562-569.
Vo et al., De novo generation of HSCs from somatic and pluripotent stem cell sources. Blood. 2015;125(17):2641-2648.
Wang et al., Generation of hematopoietic repopulating cells from human embryonic stem cells independent of ectopic HOXB4 expression. J Exp Med 2005;201(10):1603-1614.
Xie et al., Thrombopoietin promotes mixed lineage and megakaryocytic colony-forming cell growth but inhibits primitive and definitive erythropoiesis in cells isolated from early murine yolk sacs. Blood. 2003;101(4):1329-1335.
Zhan et al., Functional antigen-presenting leucocytes derived from human embryonic stem cells in vitro. Lancet. 2004;364(9429):163-171.
Andreu et al., Prevention of HLA immunization with leukocyte-poor packed red cells and platelet concentrates obtained by filtration. Blood. 1988;72(3):964-969.
Athanssiou et al., Increased expression of the ETS-related transcription factor FLI-1/ERGB correlates with and can induce the megakaryocytic phenotype. Cell Growth Differ. 1996;7(11):1525-1534.
Bertolini et al., Megakaryocytic progenitors can be generated ex vivo and safely administered to autologous peripheral blood progenitor cell transplant recipients. Blood. 1997;89(8):2679-2688.
Brevini et al., No shortcuts to pig embryonic stem cells. Theriogenology. 2010;74(4):544-550.
Buta et al., Reconsidering pluripotency tests: do we still need teratoma assays?. Stem Cell Res. 2013;11(1):552-562.
Chadwick et al., Cytokines and BMP-4 promote hematopoietic differentiation of human embryonic stem cells. Blood. 2003;102(3):906-915.
Chang et al., Definitive-like erythroid cells derived from human embryonic stem cells coexpress high levels of embryonic and fetal globins with little or no adult globin. Blood. 2006;108(5):1515-1523.
Chang et al., Proplatelet formation is regulated by the Rho/ROCK pathway. Blood. 2007;109(10):4229-4236.
Chen et al., A point mutation in the integrin beta 3 cytoplasmic domain (S752->P) impairs bidirectional signaling through alpha Iib beta 3 (platelet glycoprotein IIb-IIIa). Blood. 1994;84(6):1857-1865.

(56) References Cited

OTHER PUBLICATIONS

Chen et al., Large generation of megakaryocytes from serum-free expanded human CD34+ cells. Biochem Biophys Res Commun. 2009;378(1):112-117.
Cho et al., A critical role for extracellular protein disulfide isomerase during thrombus formation in mice. J Clin Invest. 2008;118(3):1123-1131.
Cho et al., Enhancement of thrombogenesis by plasma fibronectin cross-linked to fibrin and assembled in platelet thrombi. Blood. 2006;107(9):3555-3563.
Chockalingam et al., Management of patients refractory to platelet transfusion. J Infus Nurs. 2007;30(4):220-225.
Coller et al., Anti-GPIIb/IIIa drugs: current strategies and future directions. Thromb Haemost. 2001;86(1):427-443.
Cortin et al., Efficient in vitro megakaryocyte maturation using cytokine cocktails optimized by statistical experimental design. Exp Hematol 2005;33(10):1182-1191.
Day et al., Murine thrombosis models. Thromb Haemost. 2004;92(3):486-494.
Doe et al., Novel Rho kinase inhibitors with anti-inflammatory and vasodilatory activities. J Pharmacol Exp Ther. 2007;320(1):89-98.
Encabo et al., IL-6 precludes the differentiation induced by IL-3 on expansion of CD34+ cells from cord blood. Haematologica. 2003;88(4):388-395.
Falati et al., Real-time in vivo imaging of platelets, tissue factor and fibrin during arterial thrombus formation in the mouse. Nat Med. 2002;8(10):1175-1181.
Fan et al., Megakaryocyte Production From Feeder Cell-Free Culture of Human Embryonic Stem Cells (hESC). Blood. 2009;114(22):2528, Poster II-505, 3 pages.
Feng et al., PU.1 and C/EBPalpha/beta convert fibroblasts into macrophage-like cells. Proc Natl Acad Sci U S A. 2008;105(16):6057-6062.
Feng et al., Scalable generation of universal platelets from human induced pluripotent stem cells. Stem Cell Reports. 2014;3(5):817-831.
Figueiredo et al., RNA Interference as a Tool to Reduce the Risk of Rejection in Cell-Based Therapies. RNA Interference. IntechOpen. Ibrokhim Y. Abdurakhmonov (Ed.). Chapter 15, pp. 311-324, (2016).
Fujiki et al., Role of human interleukin-9 as a megakaryocyte potentiator in culture. Exp Hematol. 2002;30(12):1373-1380.
Furie et al., In vivo thrombus formation. J Thromb Haemost. 2007;5 Suppl 1:12-17.
Furie et al., Mechanisms of thrombus formation. N Engl J Med. 2008;359(9):938-949.
Gaur et al., Megakaryocytes derived from human embryonic stem cells: a genetically tractable system to study megakaryocytopoiesis and integrin function. J Thromb Haemost 2006;4(2):436-442.
Giammona et al., Nicotinamide (vitamin B3) increases the polyploidisation and proplatelet formation of cultured primary human megakaryocytes. Br J Haematol. 2006;135(4):554-566.
Ginsberg et al., Inside-out integrin signalling. Curr Opin Cell Biol. 1992;4(5):766-771.
Gomez et al., Derivation of cat embryonic stem-like cells from in vitro-produced blastocysts on homologous and heterologous feeder cells. Theriogenology. 2010;74(4):498-515.
Guerriero et al., Stromal cell-derived factor 1alpha increases polyploidization of megakaryocytes generated by human hematopoietic progenitor cells. Blood. 2001;97(9):2587-2595.
Guo et al., c-Myc-mediated control of cell fate in megakaryocyte-erythrocyte progenitors. Blood. 2009;114(10):2097-2106.
Hod et al., Platelet transfusion refractoriness. Br J Haematol. 2008;142(3):348-360.
Hu et al., Full reconstitution of human platelets in humanized mice after macrophage depletion. Blood. 2012;120(8):1713-1716.
Iacopetti et al., Application of Platelet-Rich Gel to Enhance Wound Healing in the Horse: A Case Report. Journal of Equine Veterinary Science. 6 pages, (2011). Pre-publication edition.
Ishizaki et al., Pharmacological properties of Y-27632, a specific inhibitor of rho-associated kinases. Mol Pharmacol. 2000;57(5):976-983.
Iwasaki et al., GATA-1 converts lymphoid and myelomonocytic progenitors into the megakaryocyte/erythrocyte lineages. Immunity. 2003;19(3):451-462.
Jean et al., Pluripotent genes in avian stem cells. Dev Growth Differ. 2013;55(1):41-51.
Jeanpierre et al., BMP4 regulation of human megakaryocytic differentiation is involved in thrombopoietin signaling. Blood 2008;112(8):3154-3163.
Junt et al., Dynamic visualization of thrombopoiesis within bone marrow. Science. 2007;317(5845):1767-1770.
Kanaji et al., Megakaryocyte proliferation and ploidy regulated by the cytoplasmic tail of glycoprotein Ibalpha. Blood. 2004;104(10):3161-3168.
Karsunky et al., Flt3 ligand regulates dendritic cell development from Flt3+ lymphoid and myeloid-committed progenitors to Flt3+ dendritic cells in vivo J Exp Med. 2003;198(2):305-313.
Khan et al., New strategies in acute myeloid leukemia: redefining prognostic markers to guide therapy. Clin Cancer Res. 2012;18(19):5163-5171.
Kimura et al., Interleukin 6 is a differentiation factor for human megakaryocytes in vitro. Eur J Immunol. 1990;20(9):1927-1931.
Klimchenko et al., A common bipotent progenitor generates the erythroid and megakaryocyte lineages in embryonic stem cell-derived primitive hematopoiesis. Blood. 2009;114(8):1506-1517.
Kuter, New thrombopoietic growth factors. Blood. 2007;109(11):4607-4616.
Lagrue-Lak-Hal et al., Expression and function of the collagen receptor GPVI during megakaryocyte maturation. J Biol Chem. 2001;276(18):15316-15325.
Lalezari et al., Ability of thrombocytes to acquire HLA specificity from plasma. Blood. 1982,59(1):167-170.
Lane et al., Stromal-derived factor 1-induced megakaryocyte migration and platelet production is dependent on matrix metalloproteinases. Blood. 2000;96(13):4152-4159.
Larson et al., Regulation of proplatelet formation and platelet release by integrin alpha IIb beta3. Blood. 2006;108(5):1509-1514.

* cited by examiner

Figure 1: Hematopoietic colony forming units
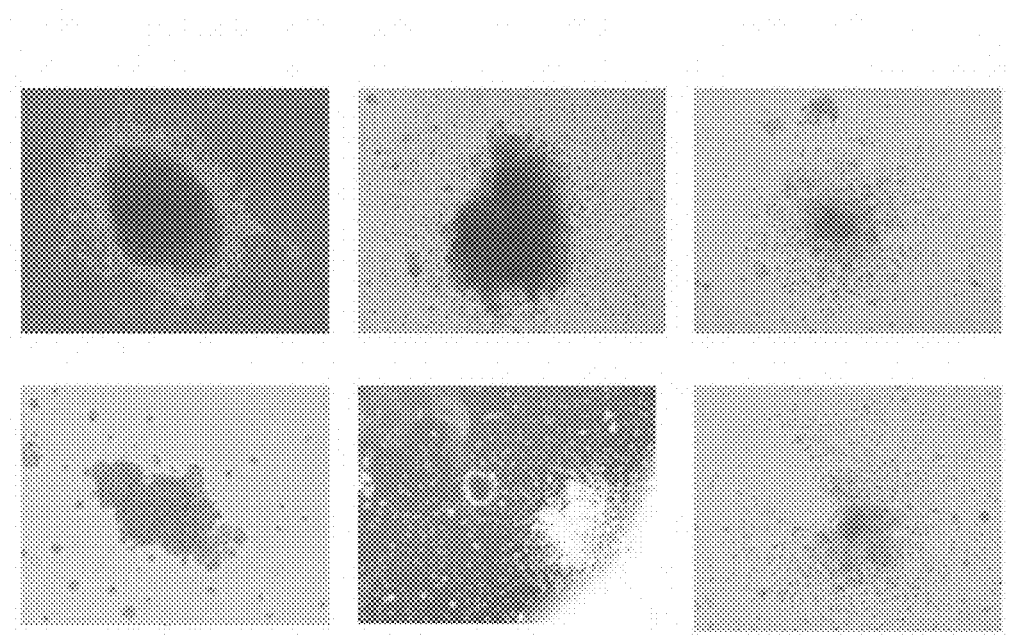
Hematopoietic CFUs derived from hemangioblast replating

Figure 2: Erythrocyte colony forming units
CFU-E                    CFU-E
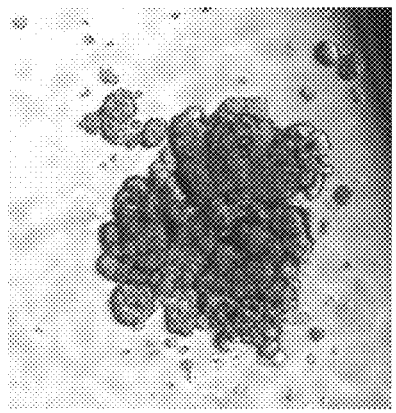 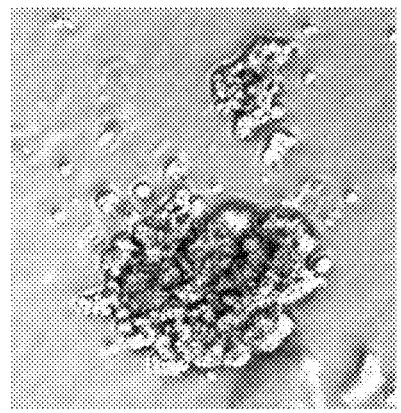
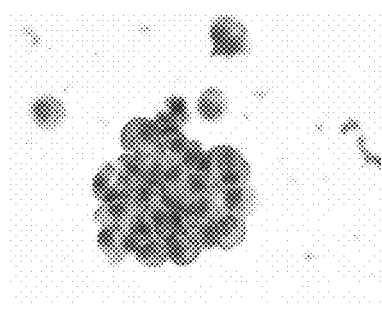 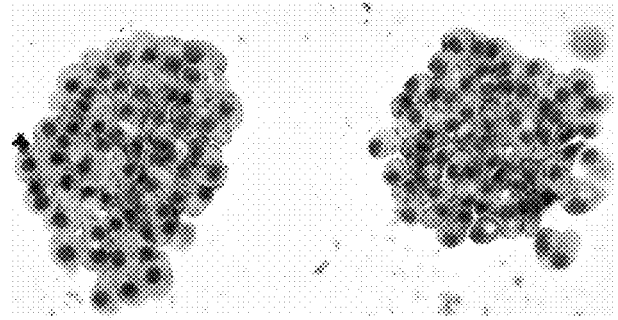

Figure 3: Multipotent colony forming units
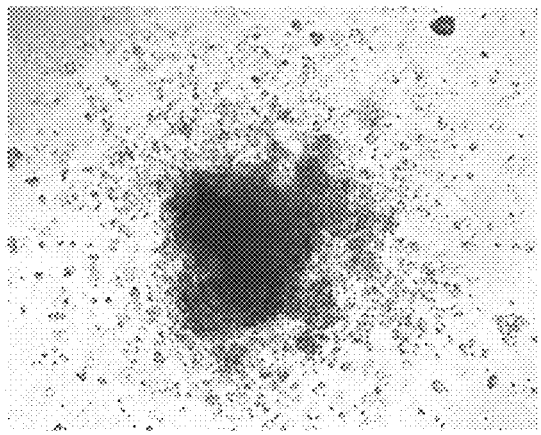
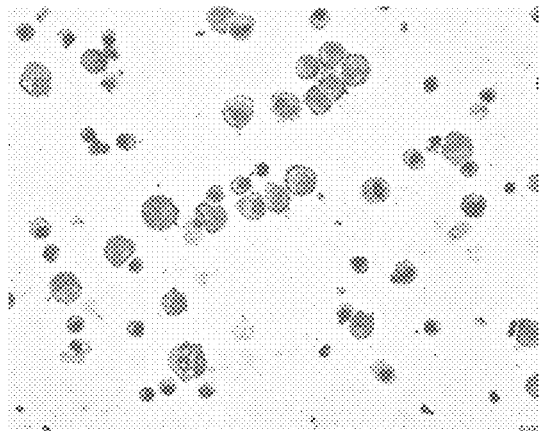
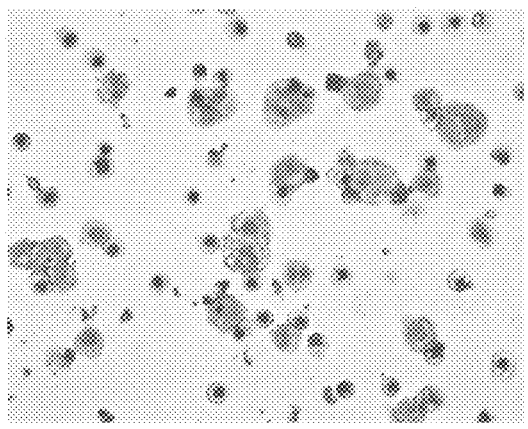
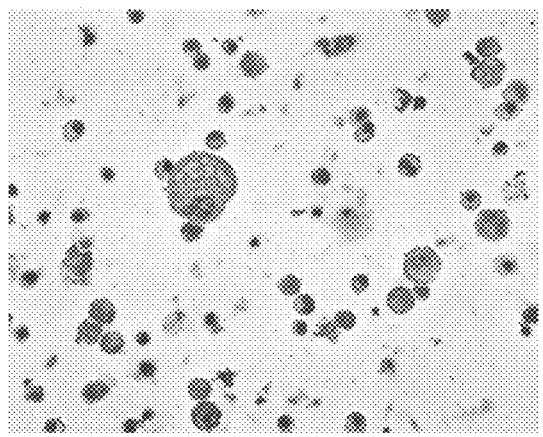
CFU-GEMM/Mix

Figure 4: Multipotent colony forming units
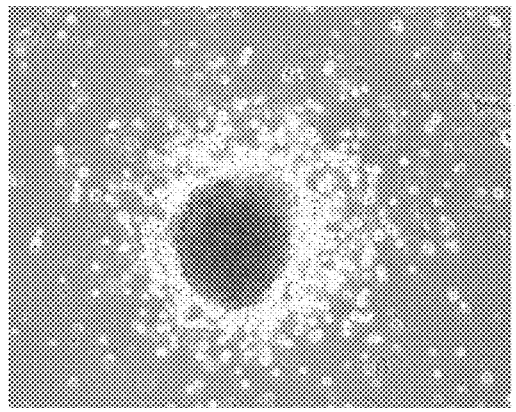
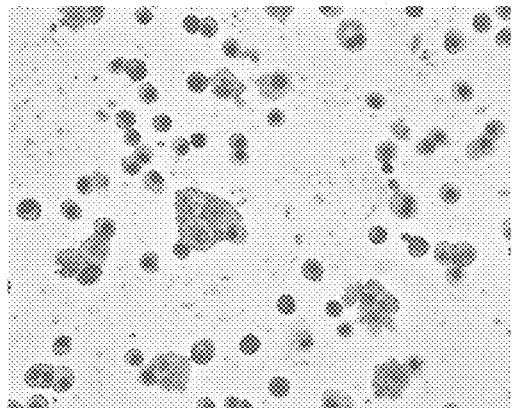
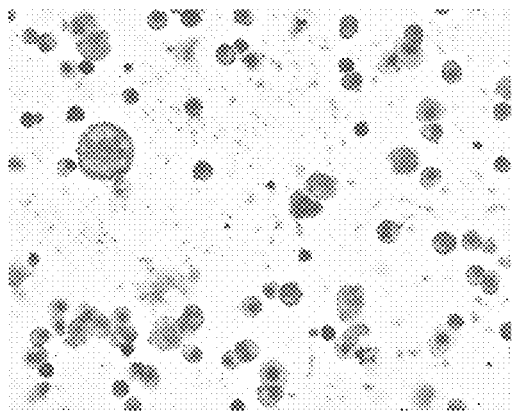
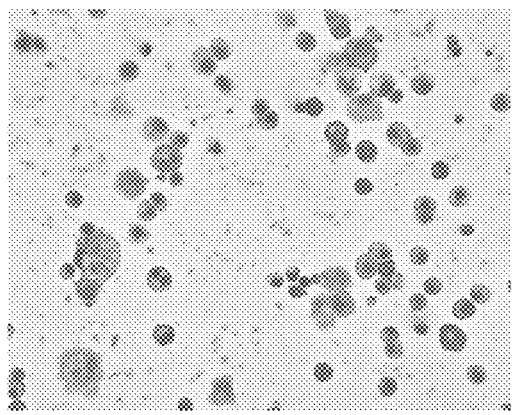
CFU-GEMM/Mix

Figure 5: Granulocyte colony forming units (CFU-G) and macrophage colony forming units (CFU-M)
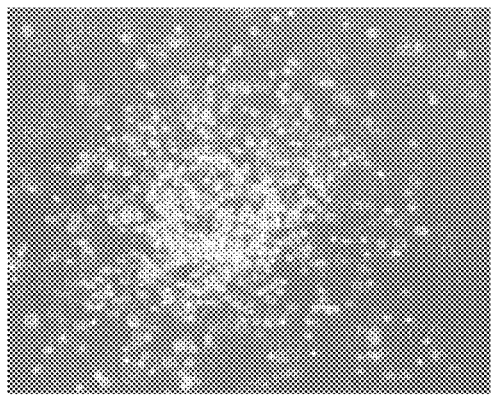
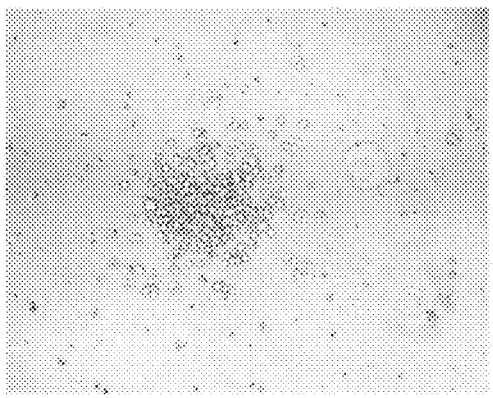
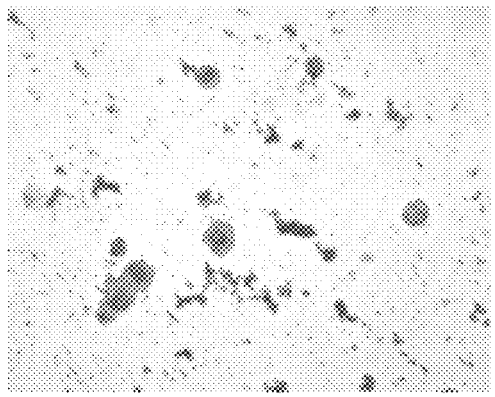
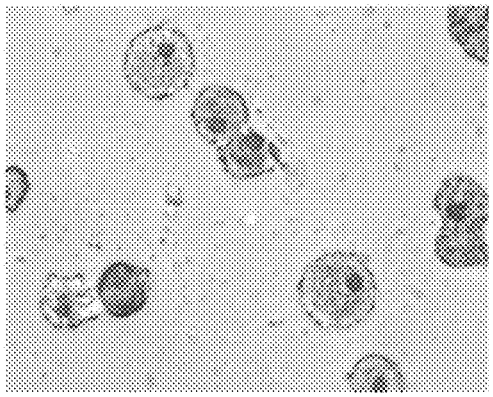
CFU-G  CFU-M

Figure 6: Granulocyte/macrophage colony forming units (CFU-GM) and megakaryocyte macrophage colony forming units (CFU-Mk)
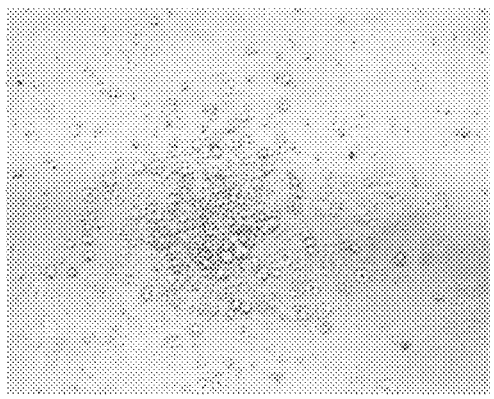
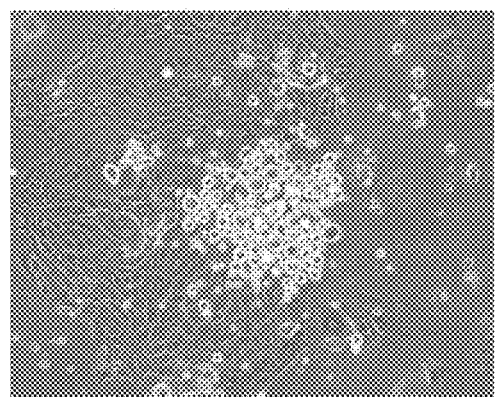
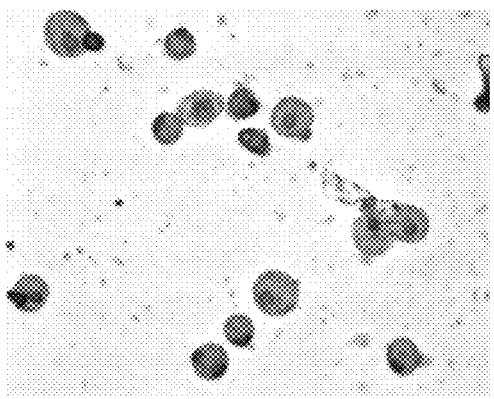
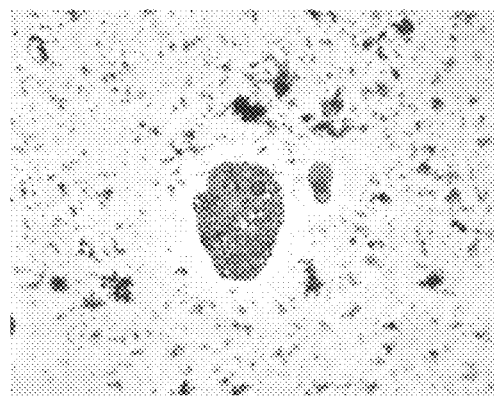
CFU-GM              CFU-Mk

Tube-cord formation of hemangioblasts (derived from H9 ES cells) replated on Matrigel.

Tube-cord formation of hemangioblasts (derived from ACT30 ES cells) replated on Matrigel.

Figure 8: Tube-cord formation of following replating of hemangioblasts derived from H1-GFP ES cells
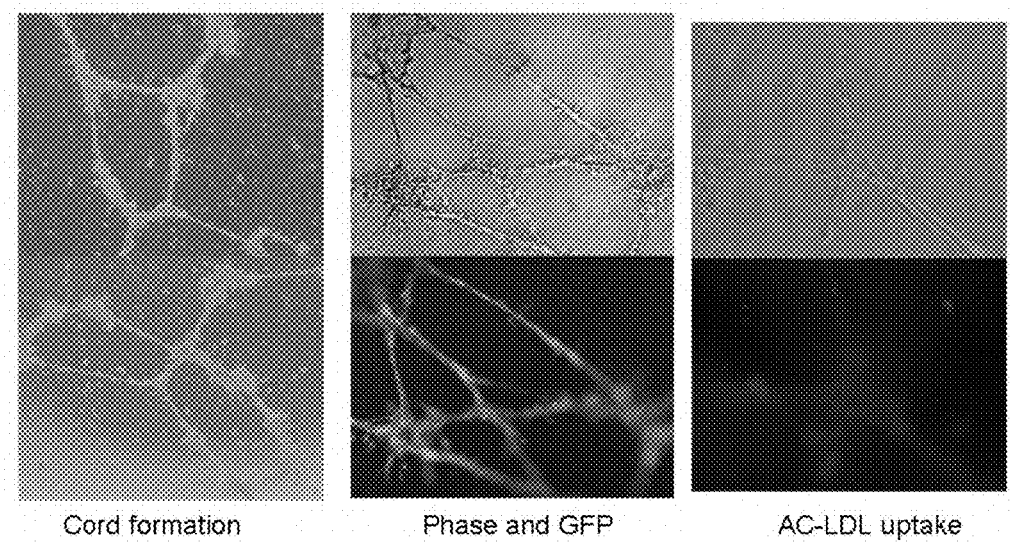
Cord formation　　　Phase and GFP　　　AC-LDL uptake
Endothelial cells derived from hemangioblast replating

Figure 9: Expression of von Willebrand factor (vWF) in replated hemangioblasts
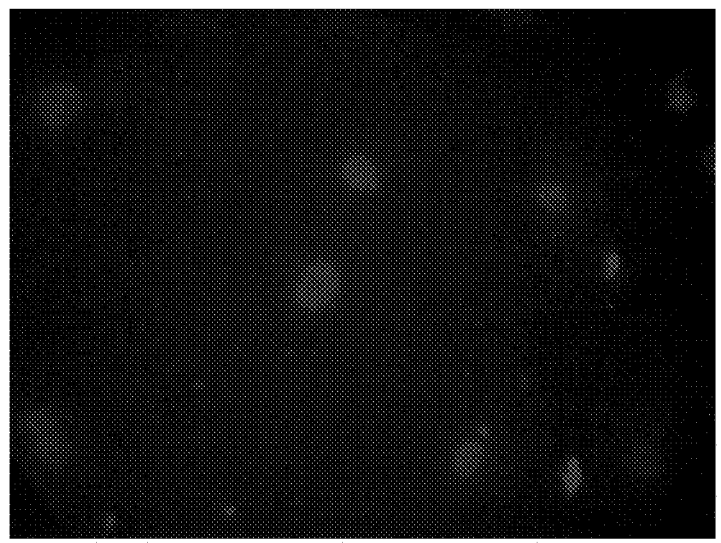
vWF expression (X40)

Figure 10: Formation of vessels in Matrigel plugs injected into SCID mice
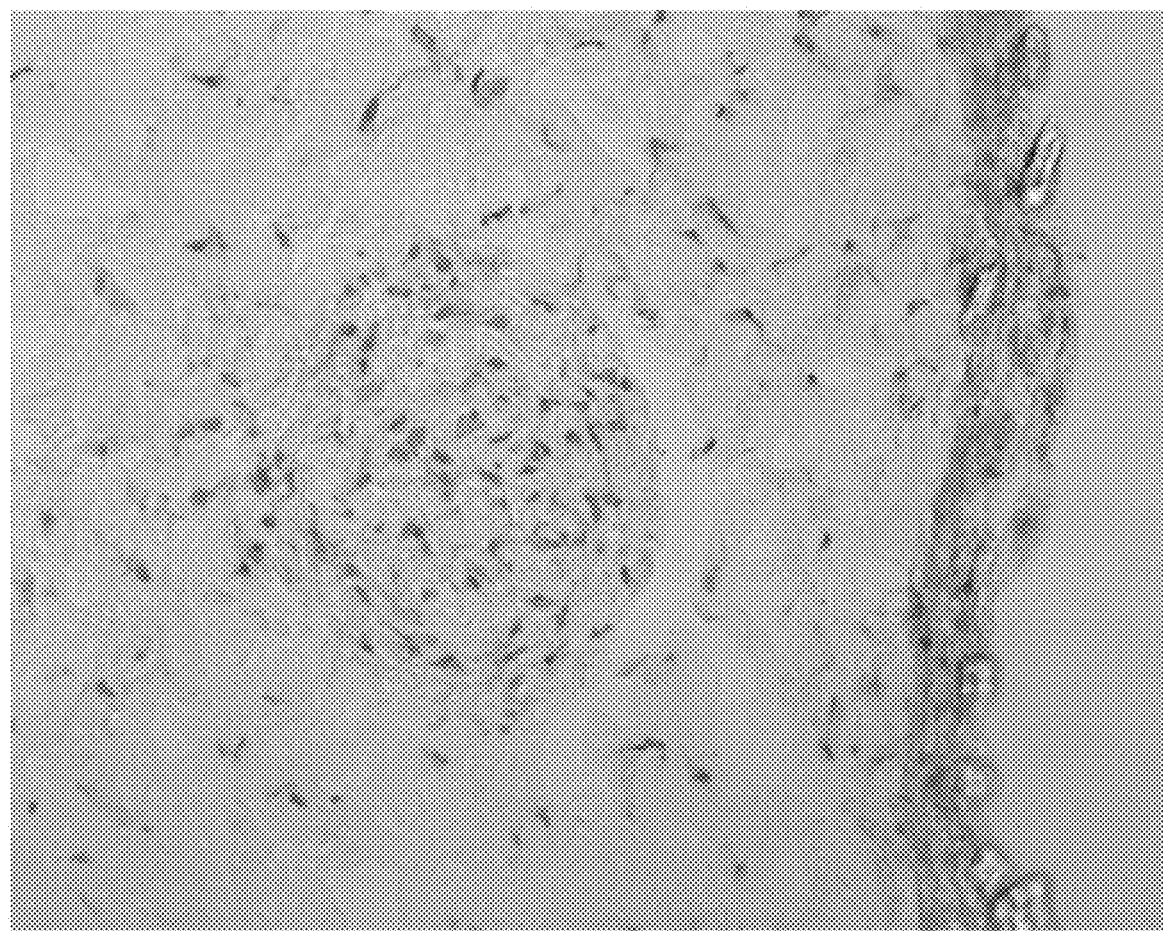

Figure 11: Vessels in Matrigel plugs stain positive for human specific nuclei antibody
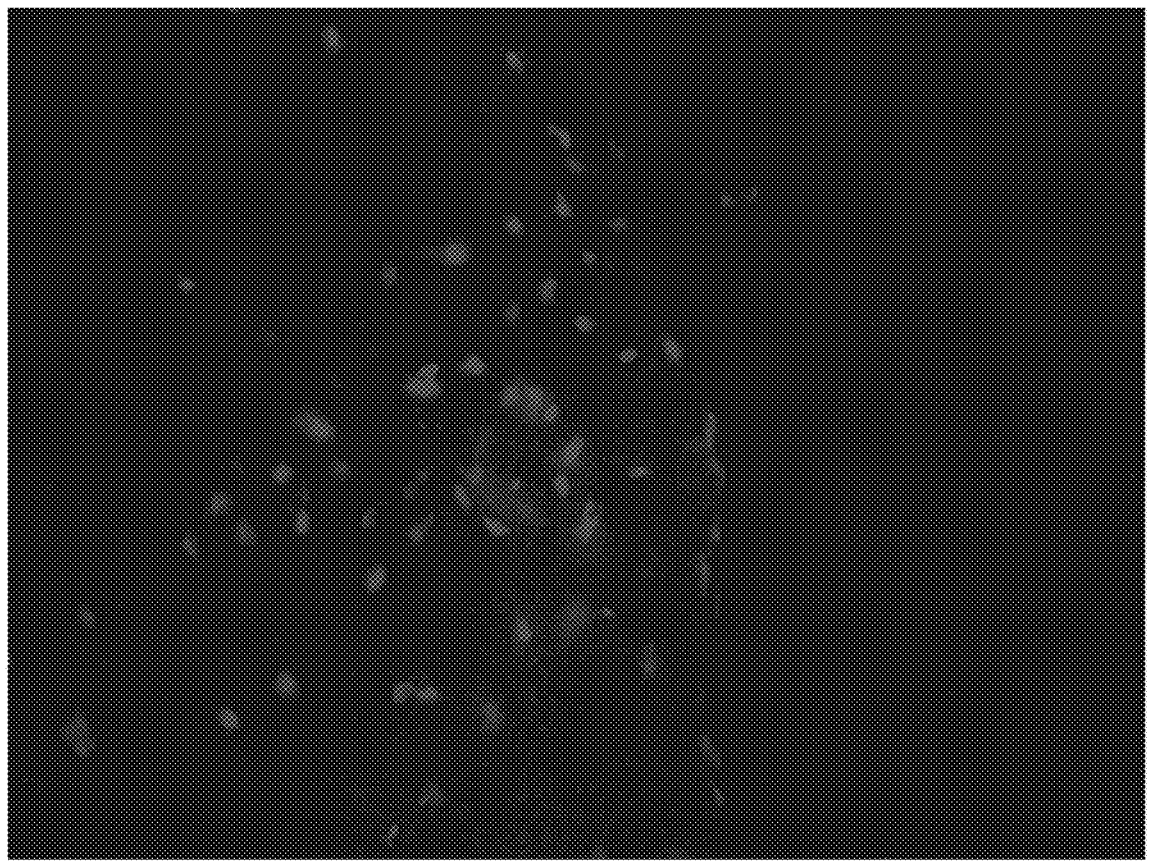

Figure 12: Homo sapiens homeobox B4 (HOXB4), mRNA (SEQ ID NO: 2)
NM_024015.4  GI:85376187

```
   1 GGAAAACGAG TCAGGGGTCG GAATAAATTT TAGTATATTT TGTGGGCAAT TCCCAGAAAT
  61 TAATGGCTAT GAGTTCTTTT TTGATCAACT CAAACTATGT CGACCCCAAG TTCCCTCCAT
 121 GCGAGGAATA TTCACAGAGC GATTACCTAC CCAGCGACCA CTCGCCCGGG TACTACGCCG
 181 GCGGCCAGAG CGAGAGAGC AGCTTCCAGC CGGAGGCGGG CTTCGGGCGG CGCGCGGCGT
 241 GCACCGTGCA GCGCTACGCG GCCTGCCGGG ACCCTGGGCC CCCGCCGCCT CCGCCACCAC
 301 CCCCGCCGCC CCCGCCACCG CCCGGTCTGT CCCCTCGGGC TCCTGCGCCG CCACCCGCCG
 361 GGGCCCTCCT CCCGGAGCCC GGCCAGCGCT GCGAGGCGGT CAGCAGCAGC CCCCGCCGC
 421 CTCCCTGCGC CCAGAACCCC CTGCACCCCA GCCCGTCCCA CTCCGCGTGC AAAGAGCCCG
 481 TCGTCTACCC CTGGATGCGC AAAGTTCACG TGAGCACGGT AAACCCCAAT TACGCCGGCG
 541 GGGAGCCCAA GCGCTCTCGG ACCGCCTACA CGCGCCAGCA GGTCTTGGAG CTGGAGAAGG
 601 AATTTCACTA CAACCGCTAC CTGACACGGC GCCGGAGGGT GGAGATCGCC CACGCGCTCT
 661 GCCTCTCCGA GCGCCAGATC AAGATCTGGT TCCAGAACCG GCGCATGAAG TGGAAAAAAG
 721 ACCACAAGTT GCCCAACACC AAGATCCGCT CGGGTGGTGC GGCAGGCTCA GCCGGAGGGC
 781 CCCCTGGCCG GCCCAATGGA GGCCCCGCG CGCTCTAGTG CCCCCGCACG CGGGAGCCAC
 841 GAACCTCGGG GTGGGGGTGG GCAGTGAGTG CAGGGGATGG GGTGGGGGA CAGGAGGGGG
 901 CCCTGGGGCC TGGGCCCCGG AAAAATCTAT CTGCCCTCCC CCACACTTTA TATACGAATA
 961 AACGCAGAAG AGGGGGAGGG GAAGCTTTAT TTATAGAAAT GACAATAGAG GGCCACGGGG
1021 AGGCCCCCCC AGAAGCAAGA TTCAAATCTC TTGCTTTCTT TCTTAAAAAA AAGAAAAAGA
1081 AAAAGCAAGA AGAAGGAAGA AAGAAAAAGA CAGAAAGAGA AATAGGAGGA GGCTGCAGCT
1141 CCTCGTTTTC AGCTTTGGCG AAGATGGATC CACGTTTCAT CTTTAATCAC GCCAGGTCCA
1201 GGCCCATCTG TCTTGTTTCC TCTGCCGAGG AGAAGACGGG CCTCGGTGGC GACCATTACC
1261 TCGACACCCG CTAACAAATG AGGCCCGGCT CGGCCGCCTC CGCCTCTGCT ACTGCCGCTG
1321 CTGGAAGACA GCCTGGATTT CCTTTCTTTG TCCCCCACTC CCGATACCCA GCGAAAGCAC
1381 CCTCTGACTG CCAGATAGTG CAGTGTTTTG GTCACGGTAA CACACACACA CTCTCCCTCA
1441 TCTTTCGTGC CCATTCACTG AGGGCCAGAA TGACTGCTCA CCCACTTCCA CCGTGGGGTT
1501 GGGGGTGGGC AACAGAGGAG GGGAGCAAGT AGGGAAGGGG GTGGCCTTGA CAACTCAGGA
1561 GTGAGCAGGA AAATTGAGTC CAAGGAAAAA GAGAGACTCA GAGACCCGGG AGGGCCTTCC
1621 TCTGAAAGGC CAAGCCAAGC CATGCTTGGC AGGGTGAGGG GCCAGTTGAG TTCTGGGAGC
1681 TGGGCACTAC TCTGCCAGTC CAGAGTTGTA CAGCAGAAGC CTCTCTCCTA GACTGAAAAT
1741 GAATGTGAAA CTAGGAAATA AAATGTGCCC CTCCCAGTCT GGGAGGAGGA TGTTGCAGAG
1801 CCCTCTCCCA TAGTTTATTA TGTTGCATCG TTTATTATTA TTATTGATAA TATTATTATT
1861 ACTATTTTTT TGTGTCATGT GAGTCCTCTC TCCTTTTCTC TTTCTGACAT TCCAAAACCA
1921 GGCCCCTTCC TACCTCTGGG GCTGCTTGAG TCTAGAACCC TTCGTATGTG TGAATATCTG
1981 TGTGCTGTAC AGAGTGACAA TAGAAATAAA TGTTTGGTTT CTTGTGACCA GCAAAAAAAA
2041 AA
```

Figure 13: Amino acid sequence of human HOXB4 (SEQ ID NO: 1)
NP_076920.1 GI:13273315

```
  1 mamssflins nyvdpkfppc eeysqsdylp sdhspgyyag gqrressfqp eagfgrraac
 61 tvqryaacrd pgpppppppp pppppppgls prapapppag allpepgqrc eavssspppp
121 pcaqnplhps pshsackepv vypwmrkvhv stvnpnyagg epkrsrtayt rqqvieleke
181 fhynryltrr rrveiahalc lserqikiwf qnrrmkwkkd hklpntkirs ggaagsaggp
241 pgrpnggpra l
```

163-221 = HOMEODOMAIN

Figure 14: Homo sapiens homeobox B4 (HOXB4), mRNA (SEQ ID NO: 4)
BC049204.1 GI: 29351567

```
   1 GGAAAACGAG TCAGGGGTCG GAATAAATTT TAGTATATTT TGTGGGCAAT TCCCAGAAAT
  61 TAATGGCTAT GAGTTCTTTT TTGATCAACT CAAACTATGT CGACCCCAAG TTCCCTCCAT
 121 GCGAGGAATA TTCACAGAGC GATTACCTAC CCAGCGACCA CTCGCCCGGG TACTACGCCG
 181 GCGGCCAGAG GCGAGAGAGC AGCTTCCAGC CGGAGGCGGG CTTCGGGCGG CGCGCGGCGT
 241 GCACCGTGCA GCGCTACGCG GCCTGCCGGG ACCCTGGGCC CCCGCCGCCT CCGCCACCAC
 301 CCCCGCCGCC CCCGCCACCG CCCGGTCTGT CCCCTCGGGC TCCTGCGCCG CCACCCGCCG
 361 GGGCCCTCCT CCCGGAGCCC GGCCAGCGCT GCGAGGCGGT CAGCAGCAGC CCCCGCCGC
 421 CTCCCTGCGC CCAGAACCCC CTGCACCCCA GCCCGTCCCA CTCCGCGTGC AAAGAGCCCG
 481 TCGTCTACCC CTGGATGCGC AAAGTTCACG TGAGCACGGT AAACCCCAAT TACGCCGGCG
 541 GGGAGCCCAA GCGCTCTCGG ACCGCCTACA CGCGCCAGCA GGTCTTGGAG CTGGAGAAGG
 601 AATTTCACTA CAACCGCTAC CTGACACGGC GCCGGAGGGT GGAGATCGCC CACGCGCTCT
 661 GCCTCTCCGA GCGCCAGATC AAGATCTGGT TCCAGAACCG GCGCATGAAG TGGAAAAAAG
 721 ACCACAAGTT GCCCAACACC AAGATCCGCT CGGGTGGTGC GGCAGGCTCA GCCGGAGGGC
 781 CCCCTGGCCG GCCCAATGGA GGCCCCGCG CGCTCTAGTG CCCCCGCACG CGGGAGCCAC
 841 GAACCTCGGG GTGGGGGTGG GCAGTGAGTG CAGGGGATGG GGTGGGGGA CAGGAGGGGG
 901 CCCTGGGGCC TGGGCCCCGG AAAAATCTAT CTGCCCTCCC CCACACTTTA TATACGAATA
 961 AACGCAGAAG AGGGGGAGGG GAAGCTTTAT TTATAGAAAT GACAATAGAG GGCCACGGGG
1021 AGGCCCCCCC AGAAGCAAGA TTCAAATCTC TTGCTTTCTT TCTTAAAAAA AAGAAAAAGA
1081 AAAAGCAAGA AGAAGGAAGA AGAAAAAGA CAGAAAGAGA AATAGGAGGA GGCTGCAGCT
1141 CCTCGTTTTC AGCTTTGGCG AAGATGGATC CACGTTTCAT CTTTAATCAC GCCAGGTCCA
1201 GGCCCATCTG TCTTGTTTCC TCTGCCGAGG AGAAGACGGG CCTCGGTGGC GACCATTACC
1261 TCGACACCCG CTAACAAATG AGGCCCGGCT CGGCCGCCTC CGCCTCTGCT ACTGCCGCTG
1321 CTGGAAGACA GCCTGGATTT CCTTTCTTTG TCCCCACTC CCGATACCCA GCGAAAGCAC
1381 CCTCTGACTG CCAGATAGTG CAGTGTTTTG GTCACGGTAA CACACACACA CTCTCCCTCA
1441 TCTTTCGTGC CCATTCACTG AGGGCCAGAA TGACTGCTCA CCCACTTCCA CCGTGGGGTT
1501 GGGGGTGGGC AACAGAGGAG GGGAGCAAGT AGGGAAGGGG GTGGCCTTGA CAACTCAGGA
1561 GTGAGCAGGG AAATTGAGTC CAAGGAAAAA GAGAGACTCA GAGACCCGGG AGGGCCTTCC
1621 TCTGAAAGGC CAAGCCAAGC CATGCTTGGC AGGGTGAGGG GCCAGTTGAG TTCTGGGAGC
1681 TGGGCACTAC TCTGCCAGTC CAGAGTTGTA CAGCAGAAGC CTCTCTCCTA GACTGAAAAT
1741 GAATGTGAAA CTAGGAAATA AAATGTGCCC CTCCCAGTCT GGGAGGAGGA TGTTGCAGAG
1801 CCCTCTCCCA TAGTTTATTA TGTTGCATCG TTTATTATTA TTATTGATAA TATTATTATT
1861 ACTATTTTTT TGTGTCATGT GAGTCCTCTC TCCTTTTCTC TTTCTGACAT TCCAAAACCA
1921 GGCCCCTTCC TACCTCTGGG GCTGCTTGAG TCTAGAACCC TTCGTATGTG TGAATATCTG
1981 TGTGCTGTAC AGAGTGACAA TAGAAATAAA TGTTTGGTTT CTTGTGAAAA AAAAAAAAA
```

Figure 15: Amino acid sequence of human HOXB4 (SEQ ID NO: 3)
AAH49204.1  GI:29351568

```
  1 mamssflins nyvdpkfppc eeysqsdylp sdhspgyyag gqrressfqp eagfgrraac
 61 tvqryaacrd pgpppppppp pppppppgls prapapppag allpepgqrc eavssspppp
121 pcaqnplhps pshsackepv vypwmrkvhv stvnpnyagg epkrsrtayt rqqvleleke
181 fhynryltrr rrveiahalc lserqikiwf qnrrmkwkkd hklpntkirs ggaagsaggp
241 pgrpnggpra l
```

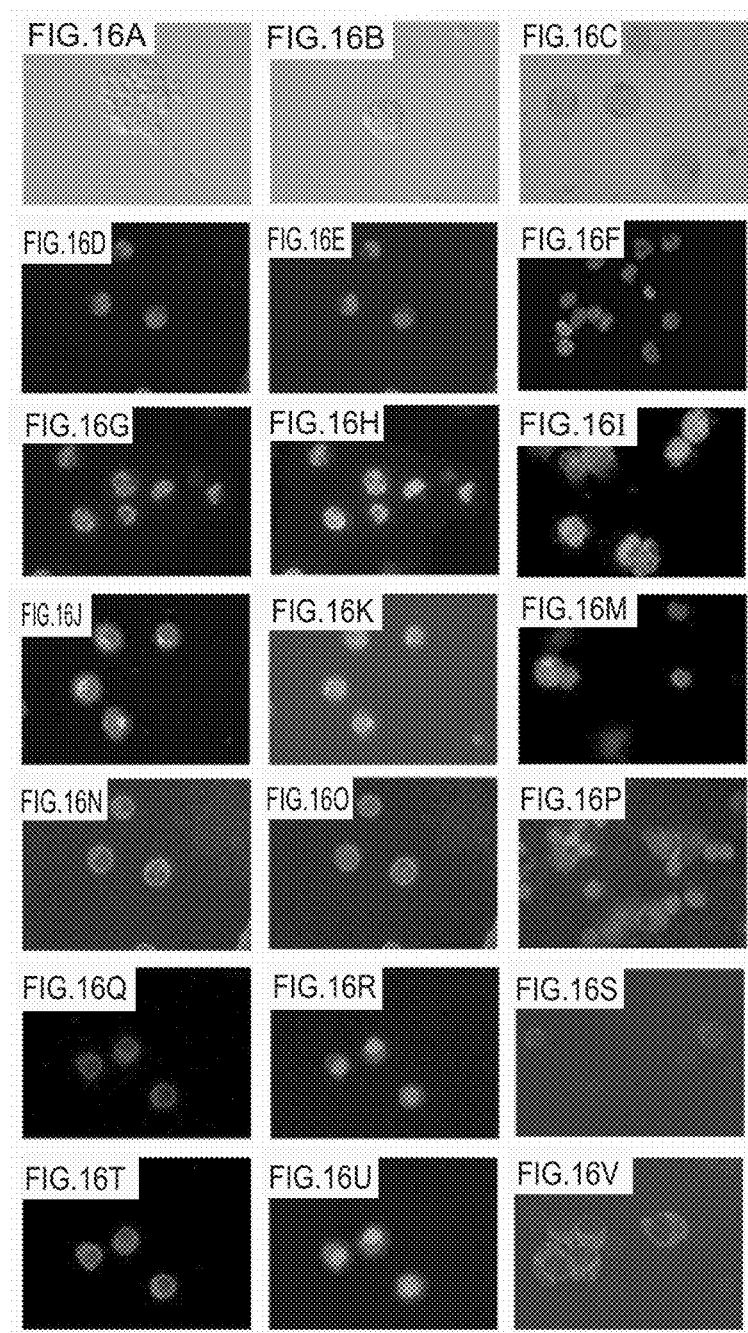

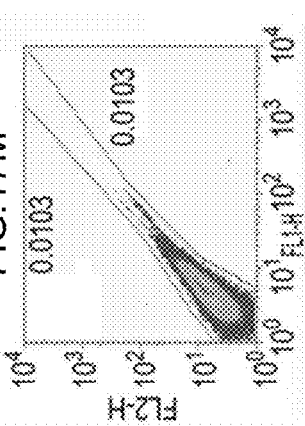
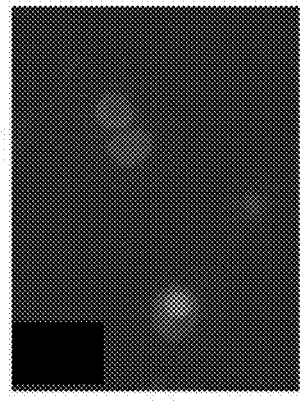
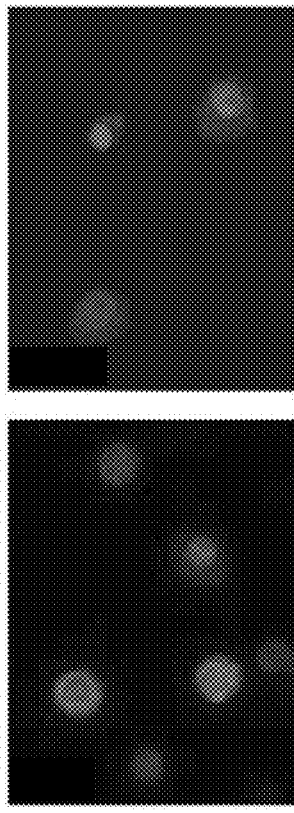
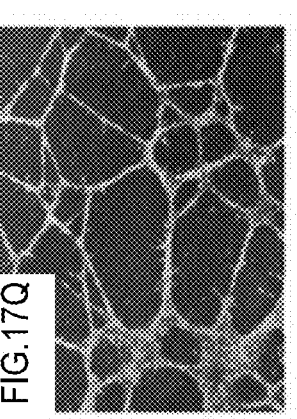
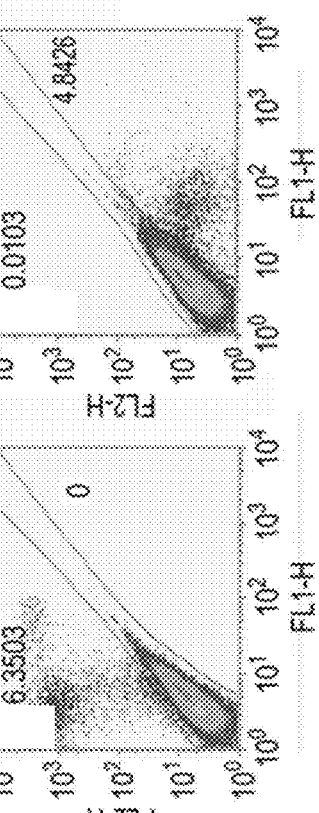
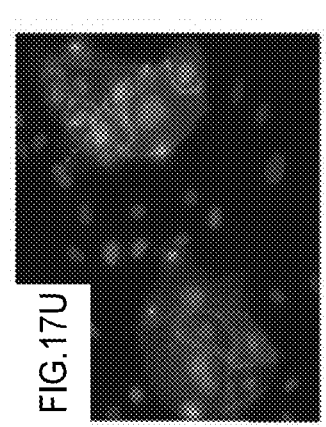
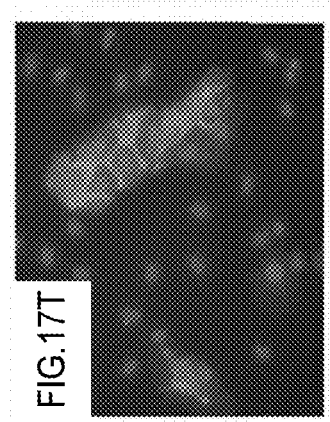
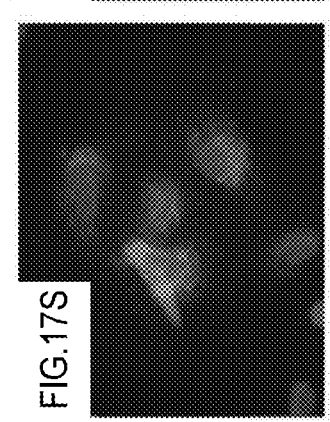
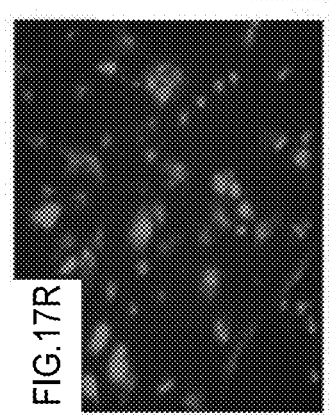

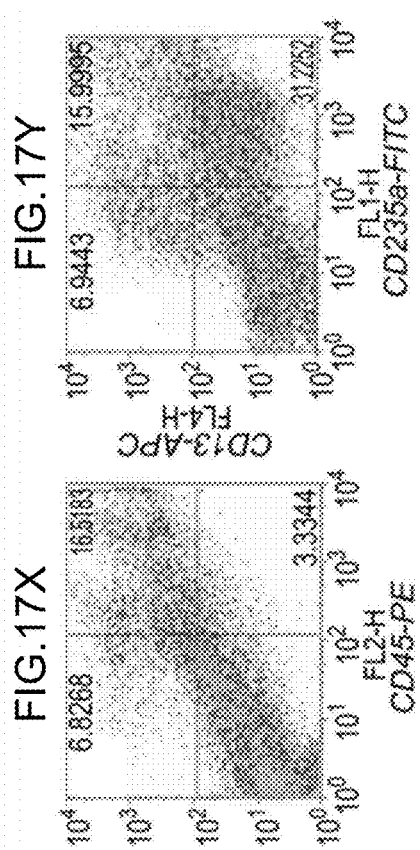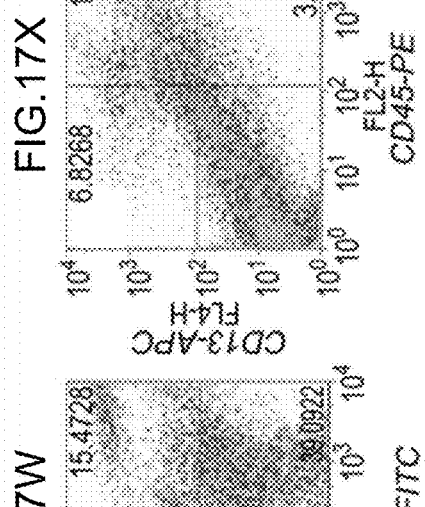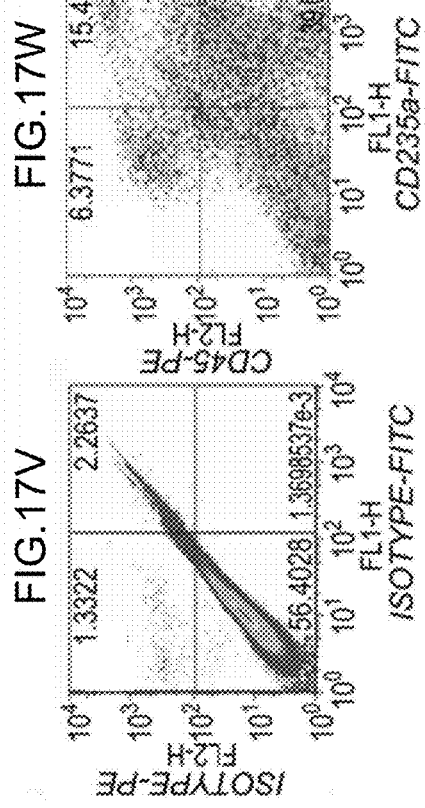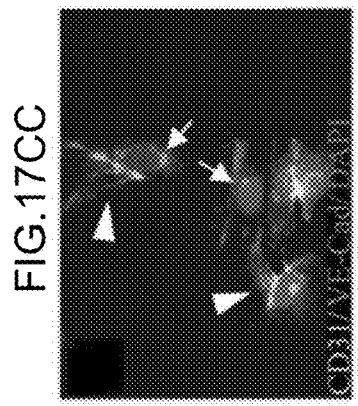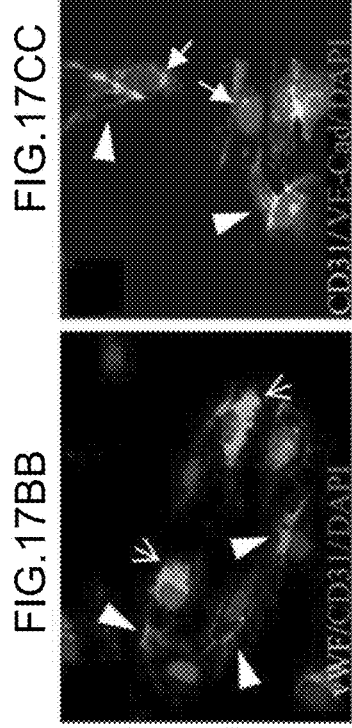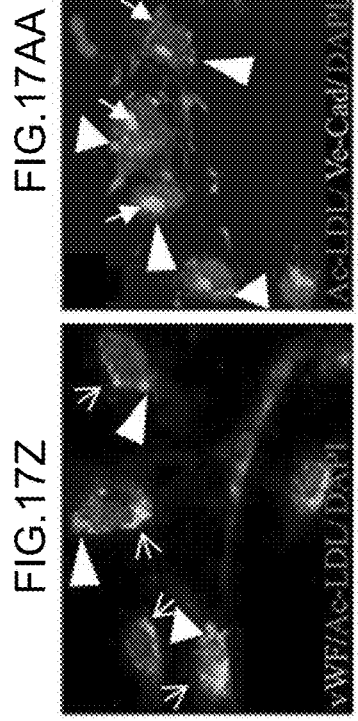

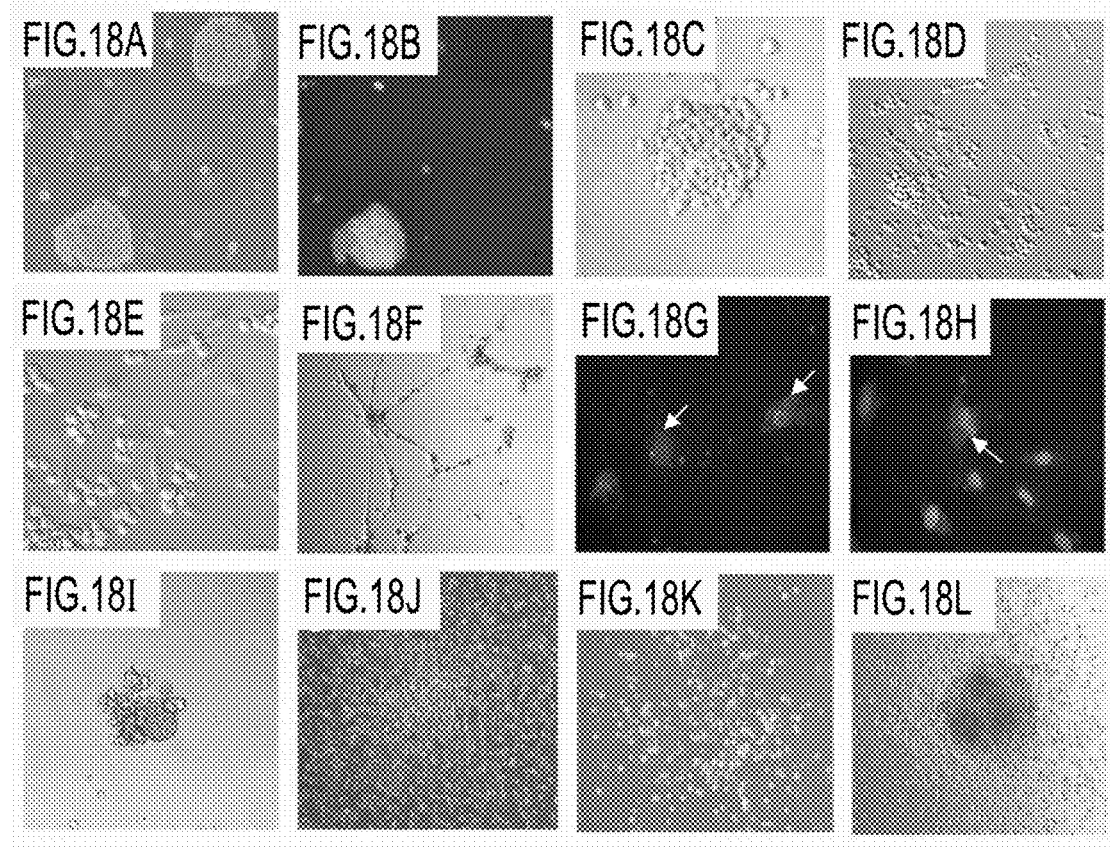
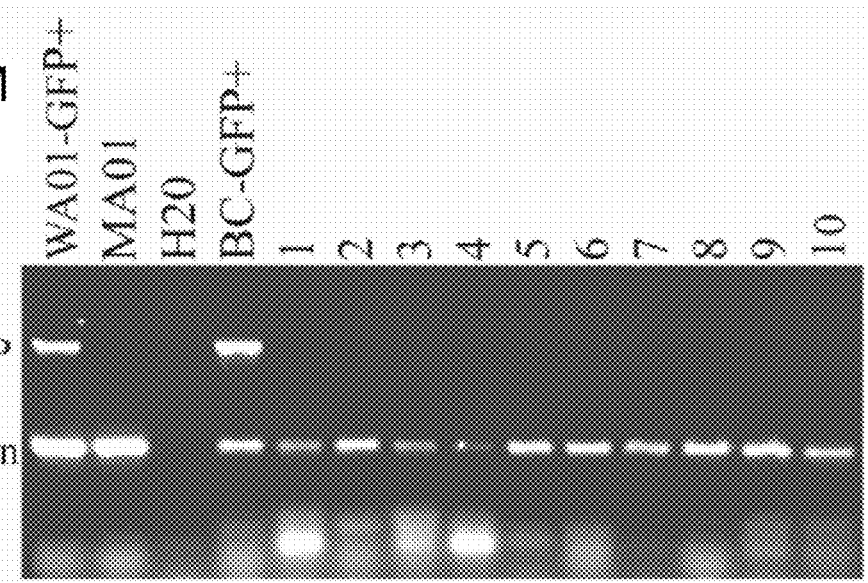
PCR analysis confirming clonogenicity: GFP negative colonies do not contain an inactive GFP gene

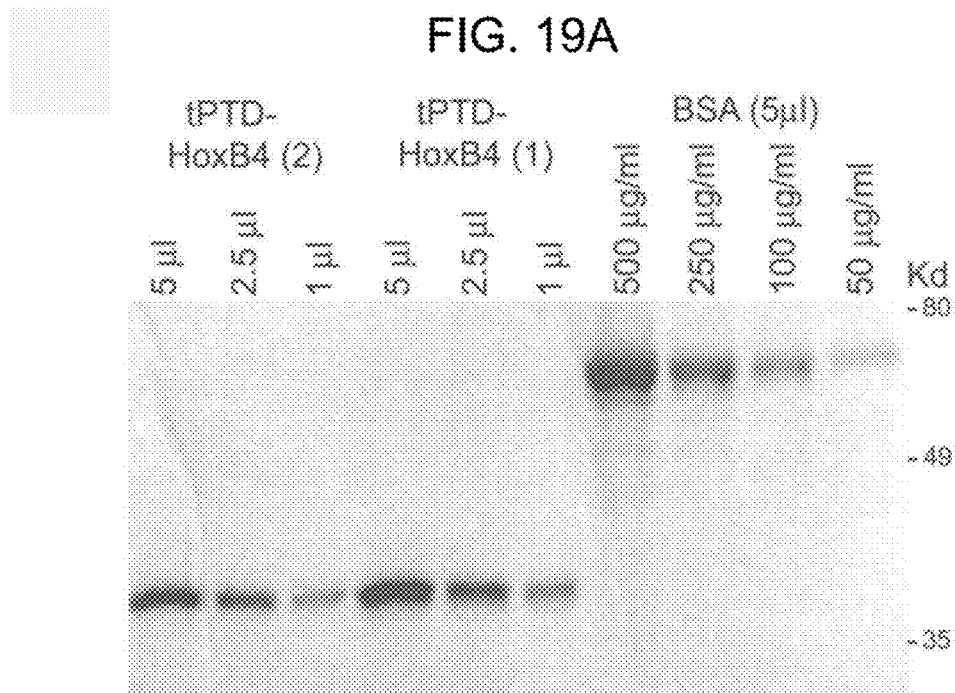
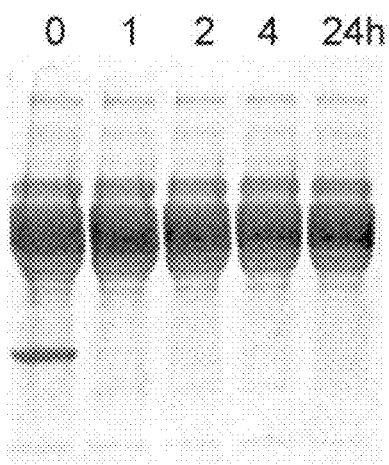
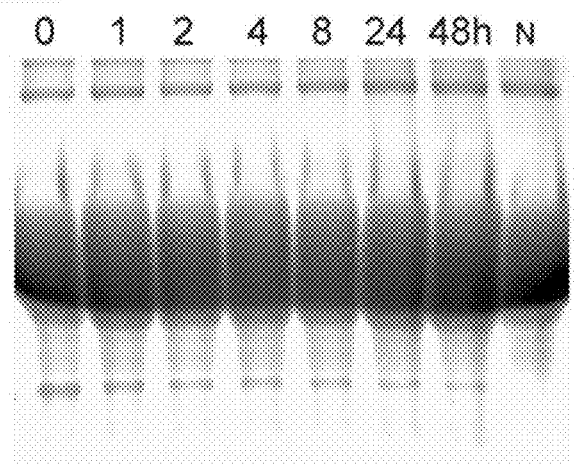

Bright regions indicate GFP+ cells

GFP + cells

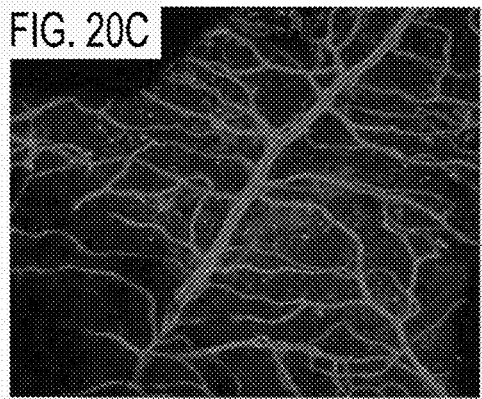
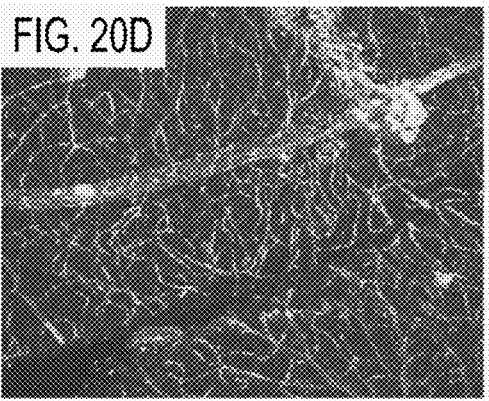
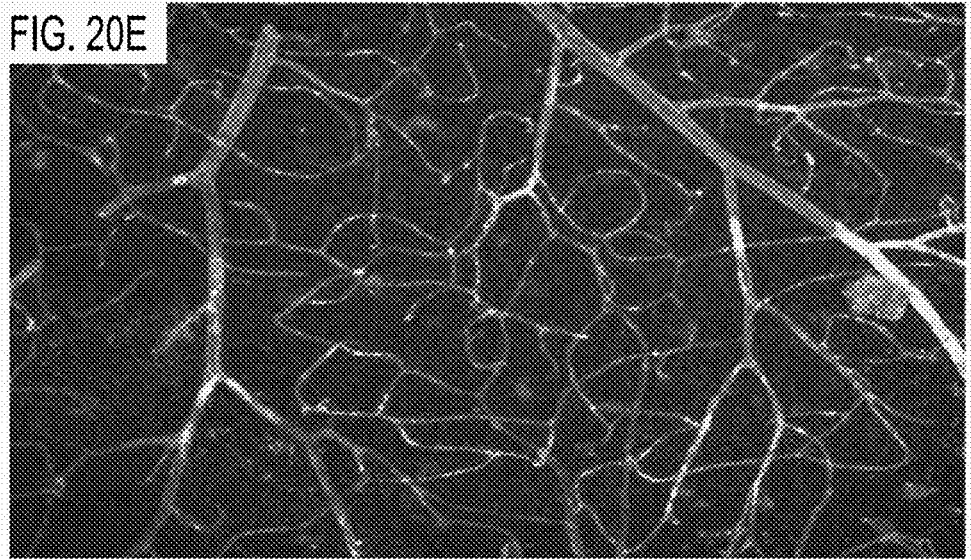

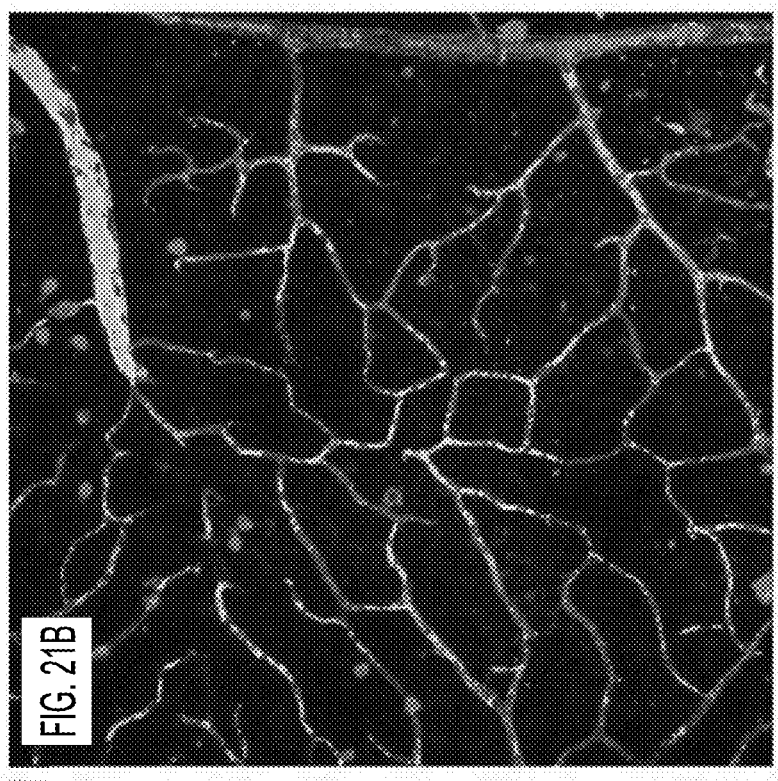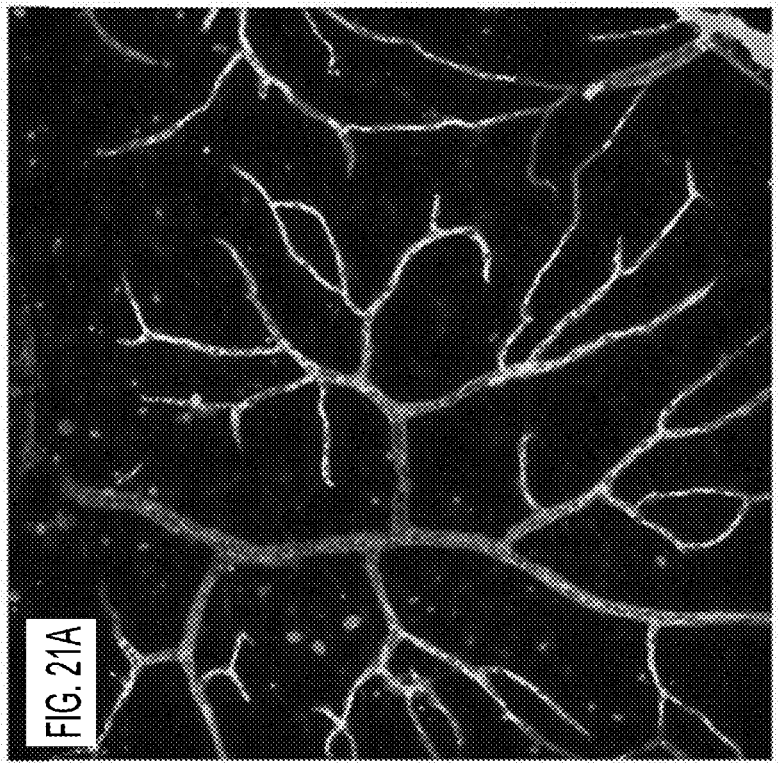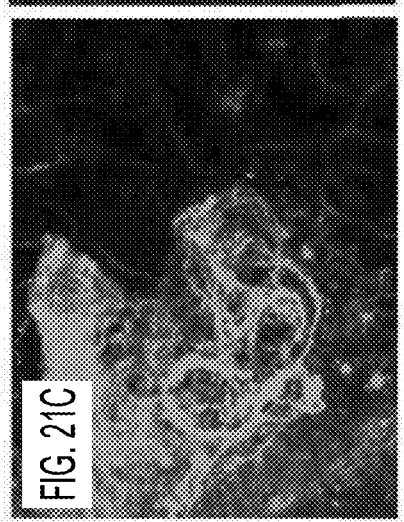

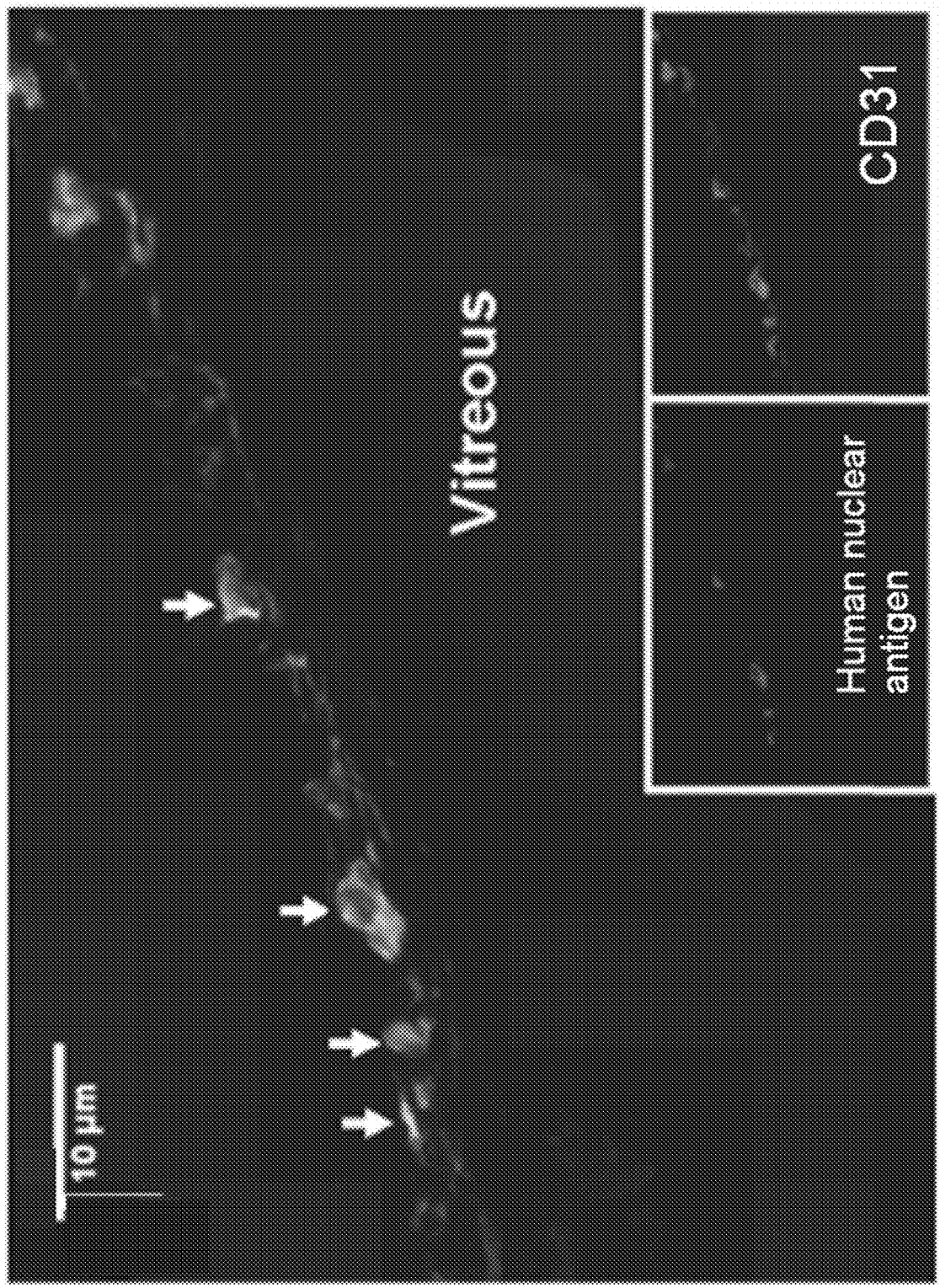

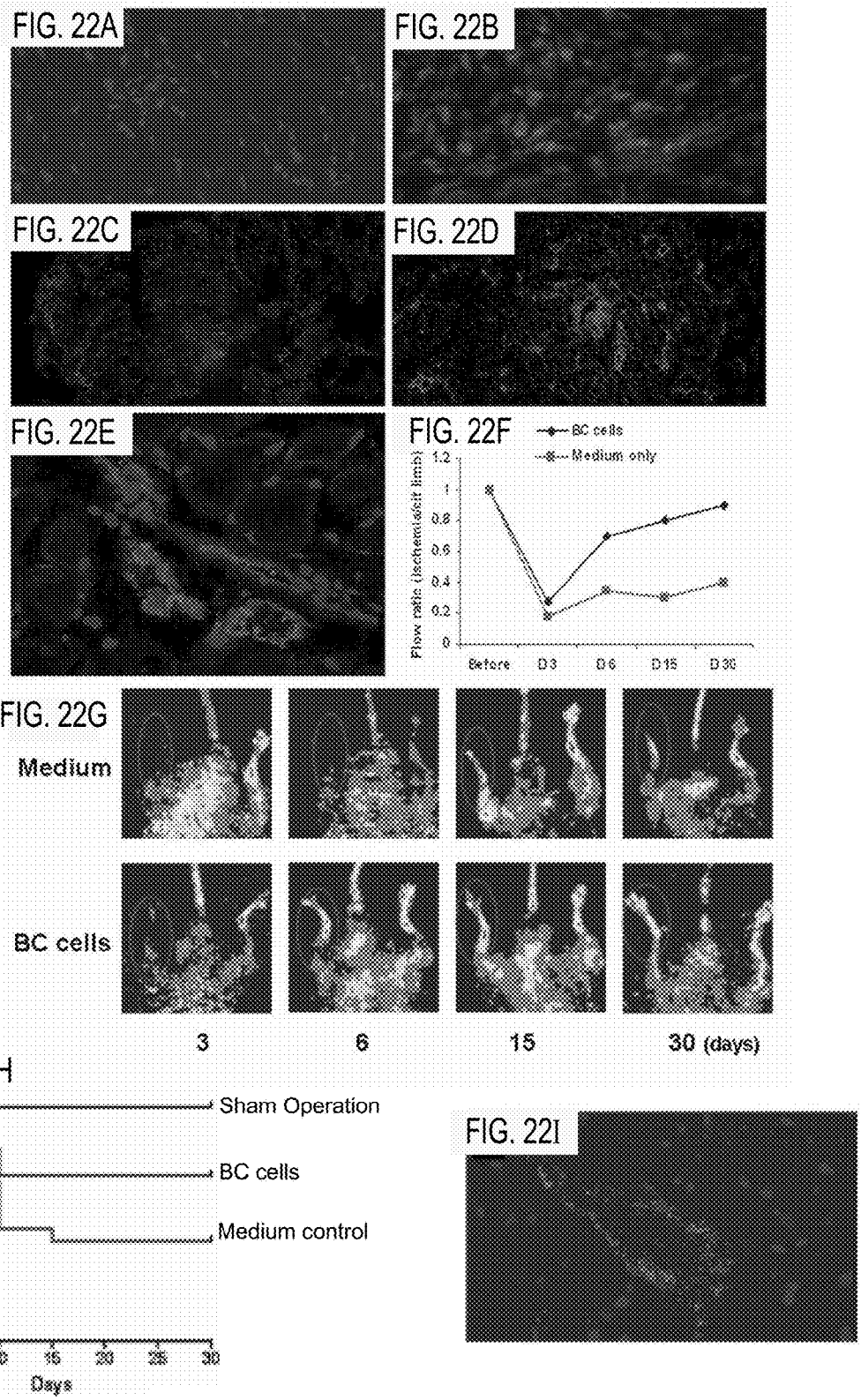

Figure 23: Transplanted hES-BC cells give rise to cardiomyocytes following myocardial infarction
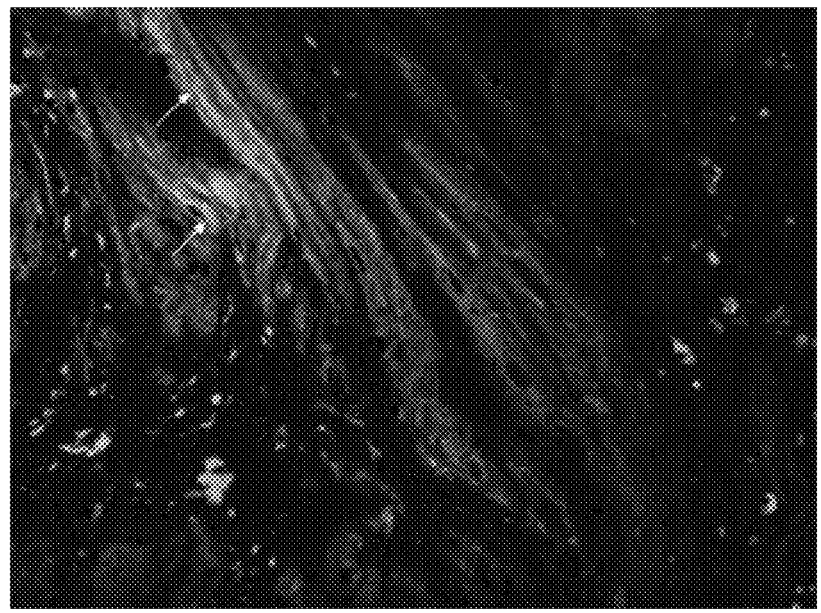

HEMANGIO-COLONY FORMING CELLS

CROSS-REFERENCE TO RELATED APPLICATIONS

This application claims the benefit of priority as a continuation of U.S. patent application Ser. No. 14/869,561, filed Sep. 29, 2015, now U.S. Pat. No. 9,938,500 issued Apr. 10, 2018, which is a continuation of U.S. patent application Ser. No. 13/190,988, filed Jul. 26, 2011, now abandoned, which is a continuation of U.S. patent application Ser. No. 11/787,262, filed Apr. 13, 2007, now U.S. Pat. No. 8,017,393 issued Sep. 13, 2011, which claims the benefit of priority under 35 U.S.C. § 119 of U.S. Provisional Application No. 60/792,224, filed Apr. 14, 2006, U.S. Provisional Application No. 60/801,993, filed May 19, 2006, U.S. Provisional Application No. 60/846,163, filed Sep. 20, 2006, U.S. Provisional Application No. 60/852,142, filed Oct. 16, 2006, U.S. Provisional Application No. 60/860,676, filed Nov. 22, 2006, and U.S. Provisional Application No. 60/918,832, filed Mar. 19, 2007. The entire contents of each of the foregoing applications are incorporated herein by reference.

FIELD OF THE INVENTION

The present invention generally relates to methods for generating and expanding human hemangio-colony forming cells. More particularly, the invention relates to a method of generating and expanding human hemangio-colony forming cells in vitro using a two-step process by first, culturing human embryo-derived stem cells in serum-free media in the presence of at least one growth factor in an amount sufficient to induce the differentiation of embryonic stem cells into embryoid bodies, and second, culturing the embryoid bodies in serum-free media in the presence of at least one growth factor in an amount sufficient to expand human hemangio-colony forming cells in the medium comprising embryoid bodies. The invention further relates to preparations of human hemangio-colony forming cells. The invention further relates to methods of differentiating human hemangio-colony forming units along a hematopoietic or endothelial lineage, as well as methods of preparing partially or fully differentiated cell types from hemangio-colony forming cells. Hemangio-colony forming cells, and cells differentiated therefrom, have a variety of uses in vitro and in vivo. The ability to generate expanded human hemangio-colony forming cells in such large quantities in vitro provides for the first time the potential to derive large numbers of human hemangio-colony forming derivative cell types, such as human hematopoietic stem cells, or endothelial cells, differentiated hematopoietic cells, such as red blood cells and platelets, that will be useful in various therapeutic applications. Furthermore, the expanded numbers of human hemangio-colony forming cells derived by the present invention may be utilized in novel therapeutic strategies in the treatment of hematopoietic and endothelial cell disorders or in blood banking.

BACKGROUND OF THE INVENTION

Hematopoietic stem cells (HSCs) are capable of self-renewal and are able to give rise to all blood cell lineages. These cells, which reside in the bone marrow, form the basis of the adult hematopoietic system. The transplantation of these cells represents the most common cell-based therapy applied today in the clinic.

HSC transplantation is used for the treatment of patients with acute or chronic leukemia, aplastic anemia and various immunodeficiency syndromes, as well as various non-hematological malignancies and auto-immune disorders. For patients with hematological malignancies, HSC transplantation may rescue patients from treatment-induced aplasia, which can occur following high-dose chemotherapy and/or radiotherapy.

Despite the widespread clinical utility of HSC transplantation, the three major sources of HSCs (human bone marrow, mobilized peripheral blood, and umbilical cord blood) are limited as two-thirds of the patients in need of somatic HSC transplantation lack well-matched donors. For example, for any given patient, there is only a 25% chance that a sibling is a human leukocyte antigen (HLA)-identical match.

HLAs are proteins on a cell's surface that help the immune system identify the cells as either self (belonging to the body) or non-self (foreign or from outside the body). The HLA proteins are encoded by clusters of genes that form a region located on human chromosome 6 known as the Major Histocompatibility Complex, or MHC, in recognition of the important role of the proteins encoded by the MHC loci in graft rejection. Accordingly, the HLA proteins are also referred to as MHC proteins. Although matching the MHC molecules of a transplant to those of the recipient significantly improves the success rate of clinical transplantation, it does not prevent rejection, even when the transplant is between HLA-identical siblings. Such rejection may be triggered by differences between the minor Histocompatibility antigens. These polymorphic antigens are usually "non-self" peptides bound to MHC molecules on the cells of the transplant tissue, and differences between minor Histocompatibility antigens will often cause the immune system of a transplant recipient to eventually reject a transplant, even where there is a match between the MHC antigens, unless immunosuppressive drugs are used.

There are three types each of class I and class II HLA. A person (typically a sibling) who has a class I and class II HLA match is called a related donor. Increased survival is associated with a match between recipient and donor class I HLA-A, HLA-B, HLA-C, and class II HLA-DRB1 and HLA-DQB1 (Morishima, et al., 2002 *Blood* (99):4200-6). For a patient who does not have a matched, related donor, a search through donor banks may provide a person with matching HLA types. However the number of people in need of a cell or tissue transplant, such as an HSC transplant, is far greater than the available supply of cells and tissues suitable for transplantation. Under these circumstances, it is not surprising that obtaining a good match between the MHC proteins of a recipient and those of the transplant is frequently impossible. Therefore, many transplant recipients must wait for an MHC-matched transplant to become available or accept a transplant that is not MHC-matched and endure higher doses of immunosuppressive drugs and still risk rejection. The ability to generate and manipulate HSCs, and/or to induce tolerance in recipients of transplants, therefore, will greatly benefit the treatment and management of human disease.

Based on work in the avian embryo, and subsequently in frogs and mammals, it has been demonstrated that the developmental programs of blood and endothelium are closely linked. For example, endothelial and hematopoietic cells emerge concurrently and in close proximity in yolk sac blood islands. The yolk sac blood islands derive from aggregates of mesodermal cells that colonize the yolk sac. The center of these aggregates gives rise to the embryonic hematopoietic cells whereas the peripheral population differentiates into endothelial cells which form the vasculature that surrounds the inner blood cells. These observations support the notion that endothelial and hematopoietic cells have a common precursor.

Additionally, in zebrafish and mouse embryos, both endothelial and hematopoietic lineages share the expression of certain genes, such as Flk1, Flt1, Tie1, Tie2, CD34, Sc1, and Runx1 (Fina et al. 1990 Blood (75): 2417-2426; Millauer et al. 1993 Cell (72): 835-846; Yamaguchi et al. 1993 Development (118): 489-498; Anagnostou et al. 1994 PNAS USA (91): 3974-3978; Kallianpur et al. 1994 Blood (83): 1200-12081; Young et al. 1995 Blood (85): 96-105, Asahara et al. 1997 Science (275): 964-967; Kabrun et al. 1997 Development (124): 2039-2048). Likewise certain gene mutations affect both endothelial and hematopoietic cell development (Shalaby et al. 1995 Nature (376): 62-66; Robb et al. 1995 PNAS USA (92): 7075-7079; Shivdasani et al. 1995 Nature (373): 432-434; Stainier et al. 1995 Development (121): 3141-3150; Bollerot et al. 2005 APMIS (113): 790-803). Further, the deletion of either Flk1 or Flt1, which are both receptors for vascular endothelial growth factor (VEGF), results in a disruption of hematopoietic and endothelial development in the mouse embryo.

The generation of mouse hemangioblasts from mouse embryonic stem cells in vitro has been reported in the literature (Choi et al. 1998 Development 125: 727-732). Further, human precursor cells capable of giving rise to both hematopoietic and endothelial cells have been derived from human ES cells (Wang et al 2004 Immunity (21): 31-41 and Wang et al. J Exp Med (201): 1603-1614), but only in small quantities, hundreds of cells at best. Moreover, no method or conditions exist for the expansion of the hemangioblast precursor cells in vitro.

Thus, there remains a need for methods for generating and expanding large numbers of human hemangioblasts as well as hemangioblast derivative cell types, i.e., hematopoietic and endothelial cells, and all solutions/mixtures containing such quantities of hemangioblasts or derivative cell types. Such methods would increase the availability of cells for transplantation as well as have utility in a variety of other therapeutic applications, such as in induction of immunological tolerance.

There is additionally a critical need for available blood for transfusion. The Red Cross and other suppliers of blood report a near constant shortage of blood. This is especially true for patients with unique blood types, patients who are Rh+, or following accidents or disasters resulting in mass casualties. Additionally, in times of war, the military has an acute need for available blood for use in the treatment of traumatic war-related injuries. The present invention provides differentiated hematopoietic cells for use in blood banking and transfusion. The cells and methods of the present invention will provide a safe and reliable advance beyond the traditional reliance on blood donations, and will help prevent critical shortages in available blood.

SUMMARY OF THE INVENTION

The present invention overcomes the problems described above by providing a method of generating and expanding human hemangioblasts or hemangio-colony forming cells in vitro. The ability to expand human hemangioblasts or hemangio-colony forming cells by the novel methods disclosed herein allows the production of cells that can be used in various therapeutic applications. Additionally, the present invention provides methods for generating human hemangioblast or hemangio-colony forming lineage cells (i.e., hematopoietic and endothelial cells) that may be used in therapeutic applications. The methods of the invention provide further utility in that they enable the generation of large numbers of human hemangioblasts or hemangio-colony forming cells as well as hematopoietic and endothelial cells, and cells differentiated therefrom, that may be used at commercial scale.

The present invention provides for a method for generating and expanding human hemangio-colony forming cells in vitro, said method comprising the steps of:

a) culturing a cell culture comprising human embryo-derived cells in serum-free media in the presence of at least one growth factor in an amount sufficient to induce the differentiation of said embryo-derived cells into embryoid bodies; and (b) adding at least one growth factor to said culture comprising embryoid bodies and continuing to culture said culture in serum-free media, wherein said growth factor is in an amount sufficient to expand human hemangio-colony forming cells in said embryoid bodies culture, wherein said stem cells, embryoid bodies and hemangio-colony forming cells are grown in serum-free media throughout steps (a) and (b) of said method.

This invention also provides a method for generating and expanding human hemangio-colony forming cells in vitro, said method comprising the steps of:

(a) culturing a cell culture comprising human embryo-derived cells in serum-free media in the presence of at least one growth factor in an amount sufficient to induce the differentiation of said embryo-derived cells into embryoid bodies;

(b) adding at least one growth factor to said culture comprising embryoid bodies and continuing to culture said culture in serum-free media, wherein said growth factor is in an amount sufficient to expand human hemangio-colony forming cells in said embryoid bodies culture, (c) said embryoid bodies are disaggregated into single cells;

(d) adding at least one growth factor to said culture comprising said single cells and continuing to culture said culture in serum-free media, wherein said growth factor is in an amount sufficient to expand human hemangio-colony forming cells in said culture comprising said single cells, wherein said stem cells, embryoid bodies and hemangio-colony forming cells are grown in serum-free media throughout steps (a)-(d) of said method.

In certain embodiments of the invention, the embryo-derived cell is an embryonic stem cell.

In certain embodiments of the methods for generating and expanding human hemangio-colony forming cells of this invention, the growth factor is a protein that comprises a homeobox protein, or a functional variant or an active fragment thereof. In certain embodiments, the homeobox protein is a protein that comprises HOXB4, or a functional variant or an active fragment thereof. It is contemplated that the HOXB4 could be mammalian HOXB4, including mouse and human HOXB4. The HOXB4 protein could be full length HOXB4 protein. In yet further embodiments, the HOXB4 comprises the amino acid sequence of SEQ ID NO: 1 or SEQ ID NO: 4.

In certain embodiments of the methods for generating and expanding human hemangio-colony forming cells of this invention, the growth factor that comprises HOXB4 is a fusion protein that comprises HOXB4 and a protein transduction domain (PTD). In yet further embodiments, the PTD and the HOXB4 are conjugated via a linker. In yet further embodiments, the PTD is TAT protein, a functional variant or an active fragment thereof (including a TAT polypeptide). In certain embodiments, the TAT protein comprises the amino acid sequence of SEQ ID NO: 14. In yet further embodiments, the PTD comprises one or more copies of a TAT polypeptide with the amino acid sequence of SEQ ID NO: 14. In certain embodiments, the PTD is SEQ ID NO: 15.

In certain embodiments of the methods for generating and expanding human hemangio-colony forming cells of this invention, the growth factor is selected from the group consisting of vascular endothelial growth factor (VEGF), bone morphogenic proteins (BMP), stem cell factor (SCF), Flt-3L (FL) thrombopoietin (TPO) and erythropoietin (EPO). In further embodiments, vascular endothelial growth factor (VEGF) or bone morphogenic protein (BMP), or both, are added to culturing step (a) within 0-48 hours of culturing the cell culture comprising the hES cells. In still other further embodiments, the stem cell factor (SCF), Flt-3L (FL) or thrombopoietin (TPO), or any combination thereof, are added to the cell culture comprising hES cells within 48-72 hours from the start of culturing step (a).

In certain embodiments of the methods for generating and expanding human hemangio-colony forming cells of this invention, a growth factor that comprises a HOXB4 protein, or a functional variant or active fragment (or domain) thereof, is added to the step(s) in which said protein is added multiple times, such as, for example, once a day or once every other day.

In certain embodiments of the methods for generating and expanding human hemangio-colony forming cells of this invention, the growth factor comprising a homeobox protein is added to step (b) within 48-72 hours from the start of step (a). In certain embodiments of the methods of this invention, the HOXB4 protein, or functional variants or active fragments thereof, is added to step (b) within 48-72 hours from the start of step (a).

In certain embodiments, the methods for generating and expanding human hemangio-colony forming cells of this invention further comprise the step of adding erythropoietin (EPO) to step (b). In certain embodiments, the method of this invention described in paragraph 0016 further comprises the step of adding erythropoietin (EPO) to steps (b) and (d).

In certain embodiments, the methods for generating and expanding human hemangio-colony forming cells of this invention further comprise the step(s) of purifying and/or isolating the human hemangio-colony forming cells. The hemangio-colony forming cells may be purified by using immunoaffinity column chromatography with an anti-CD71 antibody. The hemangio-colony forming cells may be isolated by size and/or by morphology.

In certain embodiments of the methods for generating and expanding human hemangio-colony forming cells of this invention, the cell culture comprising human embryo-derived stem cells are derived from a library of human embryonic stem cells, wherein said library of human embryonic stem cells comprises stem cells, each of which is hemizygous or homozygous for at least one MHC allele present in a human population, wherein each member of said library of stem cells is hemizygous or homozygous for a different set of MHC alleles relative to the remaining members of the library. In further embodiments, the library of human embryonic stem cells comprises stem cells that are hemizygous or homozygous for all MHC alleles present in a human population. These methods generate a library of human hemangio-colony forming cells, each of which is hemizygous or homozygous for at least one MHC allele present in a human population, wherein each member of said library of stem cells is hemizygous or homozygous for a different set of MHC alleles relative to the remaining members of the library. In further embodiments, these methods generate a library of human hemangio-colony forming cells that are hemizygous or homozygous for all MHC alleles present in a human population. Thus, this invention also provides a library of human hemangio-colony forming cells made by such methods. This library could be used as follows.

This invention provides a method to treat a human patient in need of treatment involving administering human hematopoietic stem cells or human endothelial cells to said patient, comprising the steps of:

(a) selecting said patient;

(b) identifying MHC proteins expressed on the surface of said patient's cells;

(c) providing a library of human hemangio-colony forming cells described in the preceding paragraph 0024;

(d) selecting the human hemangio-colony forming cells from the library that match said patient's MHC proteins on said patients' cells;

(e) differentiating said human hemangio-colony forming cells identified in step (d) into human hematopoietic stem cells, endothelial cells or both, depending on need;

(f) administering said human hematopoietic stem cells, endothelial cells or both from step (e) to said patient. This method could be performed in a regional center, such as a hospital or a medical center, or any other suitable facility.

In certain embodiments, the methods for generating and expanding human hemangio-colony forming cells of this invention further comprise the step of growing the human hemangio-colony forming cells under conditions suitable to induce the differentiation of said human hemangio-colony forming cells into human hematopoietic stem cells.

In certain embodiments, the methods for generating and expanding human hemangio-colony forming cells of this invention further comprise the step of growing said human hemangio-colony forming cells under conditions suitable to induce the differentiation of said human hemangio-colony forming cells into human endothelial cells. In further embodiments, the condition suitable to induce the differentiation of said human hemangio-colony forming cells into human endothelial cells comprises growing the human hemangio-colony forming cells on fibronectin-coated culture plates.

In certain embodiments of this invention, the methods for generating and expanding human hemangio-colony forming cells result in at least 10,000 human hemangio-colony forming cells, at least 50,000 human hemangio-colony forming cells, at least 100,000 human hemangio-colony forming cells, at least 500,000 human hemangio-colony forming cells, at least $1 \times 10^6$ human hemangio-colony forming cells, at least $2 \times 10^6$ human hemangio-colony forming cells, at least $3 \times 10^6$ human hemangio-colony forming cells or at least $4 \times 10^6$ human hemangio-colony forming cells. These methods result in cell solutions that may comprise between 10,000 to 4 million human hemangio-colony forming cells.

Thus, this invention also provides a solution of human hemangio-colony forming cells (which could be grown in serum-free media) comprising at least 10,000 human hemangio-colony forming cells, at least 50,000 human hemangio-colony forming cells, at least 100,000 human hemangio-colony forming cells, at least 500,000 human hemangio-colony forming cells, at least $1 \times 10^6$ human hemangio-colony forming cells, at least $2 \times 10^6$ human hemangio-colony forming cells, at least $3 \times 10^6$ human hemangio-colony forming cells or at least $4 \times 10^6$ human hemangio-colony forming cells. These solutions could be injectable to a subject. These solutions could be suitable for freezing. These solutions could be serum-free. The human hemangio-colony forming cells in these solutions are capable of differentiating into at least hematopoietic and endothelial cells but have greater developmental potential to differentiate into other cell types. This invention also provides a use of these solutions for the manufacture of a medicament to treat a disease that could be treated by the administration of hemangio-colony forming cells, hematopoietic cells or endothelial cells.

This invention also provides a method of producing a solution of human hemangio-colony forming cells suitable for injection into a patient comprising the steps of isolating the solution of cells described in the preceding paragraph and placing the cells into a solution suitable for injection into a patient. This invention also provides a method of producing a solution of human hemangio-colony forming cells suitable for freezing comprising the steps of isolating the solution of cells described in the preceding paragraph and placing the cells into a solution suitable for freezing.

This invention also provides a method for administering human hematopoietic stem cells to a patient in need thereof, comprising the steps of:
 (a) selecting a patient in need thereof;
 (b) supplying human hemangio-colony forming cells generated and expanded by a method of this invention;
 (c) differentiating said human hemangio-colony forming cells into human hematopoietic stem cells; and
 (d) administering some of all of said human hematopoietic stem cells to said patient.

This invention also provides a method for administering human hematopoietic stem cells to a patient in need thereof, comprising the steps of:
 (a) selecting the patient in need thereof;
 (b) supplying human hemangio-colony forming cells in an amount of at least 10,000 cells;
 (c) differentiating said human hemangio-colony forming cells into human hematopoietic stem cells; and
 (d) administering some or all of said human hematopoietic stem cells to said patient.

This invention also provides a method for administering human endothelial cells into a patient in need thereof, comprising the steps of:
 (a) selecting a patient in need thereof;
 (b) supplying human hemangio-colony forming cells generated and expanded by a method of this invention;
 (c) differentiating said human hemangio-colony forming cells into human endothelial cells; and
 (d) administering some or all of said human endothelial cells to said patient.

This invention also provides a method for administering human endothelial cells into a patient in need thereof, comprising the steps of:
 (a) selecting a patient in need thereof;
 (b) supplying human hemangio-colony forming cells in an amount of at least 10,000 cells;
 (c) differentiating said human hemangio-colony forming cells into human endothelial cells; and
 (d) administering some or all of said human endothelial cells to said patient.

In certain embodiments, the human hemangio-colony forming cells are in an amount between 10,000 to 4 million cells.

This invention also provides a method for treating an endothelial cell disorder in a patient in need thereof, comprising the steps of:
 (a) selecting a patient in need thereof;
 (b) supplying human hemangio-colony forming cells generated and expanded by a method described above;
 (c) differentiating said human hemangio-colony forming cells into human endothelial cells; and
 (d) administering some or all of said human endothelial cells to said patient.

This invention also provides a method for treating an endothelial cell disorder in a patient in need thereof, comprising the steps of:
 (a) selecting a patient in need thereof;
 (b) supplying human hemangio-colony forming cells in an amount of at least 10,000 cells;
 (c) differentiating said human hemangio-colony forming cells into human endothelial cells; and
 (d) administering some or all of said human endothelial cells to said patient.

In certain embodiments, the human hemangio-colony forming cells are in an amount between 10,000 to 4 million cells.

The endothelial cell disorder to be treated by these methods includes myocardium infarction, stroke, atherosclerosis and ischemia. The ischemia could occur in the brain, limbs, heart, lungs, skin and eye.

This invention provides a method for producing human hematopoietic stem cells in vitro, comprising the steps of:
 (a) supplying human hemangio-colony forming cells generated and expanded by a method of this invention; and
 (b) growing said human hemangio-colony forming cells under conditions suitable to induce the differentiation of said human hemangio-colony forming cells into human hematopoietic stem cells.

This invention also provides a method for producing human endothelial cells in vitro, comprising the steps of:
 (a) supplying human hemangio-colony forming cells generated and expanded by a method of this invention; and
 (b) growing said human hemangio-colony forming cells under conditions suitable to induce the differentiation of said human hemangio-colony forming cells into human endothelial cells.

This invention also provides a method for expanding hemangio-colony forming cells comprising growing mammalian hemangio-colony forming cells in serum-free media in the presence of a protein that comprises a homeobox protein (such as HOXB4) or a functional equivalent or an active fragment thereof in an amount sufficient to support the proliferation of said hemangioblast cells. The hemangio-colony forming cells to be expanded could be enriched, purified, or isolated from cord blood, peripheral blood, or bone marrow. The hemangio-colony forming cells could be human hemangio-colony forming cells. This method could result in solutions comprising hemangio-colony forming cells of between 10,000 to $4 \times 10^6$ hemangio-colony forming cells, or more. The HOXB4 protein used for this method could be any that are suitable for use for the methods for generating and expanding human hemangio-colony forming cells of this invention.

The present invention also provides for methods of inducing immunological tolerance using the human hemangio-colony forming cells generated and expanded or expanded according to the methods of this invention. The tolerizing human hemangio-colony forming cells are chosen to share histocompatibility markers with an allograft, and may be administered to a human recipient before or concurrently with the allograft or cell treatment that regenerates a cellular function needed by the patient. The resulting immune tolerance subsequently decreases the risk of acute or chronic rejection of the allograft or cell treatment.

The large numbers of hemangio-colony forming cells generated by the methods disclosed herein enable tolerance protocols in which toxic pre-conditioning treatments may be eliminated. The donor human hemangio-colony forming cells may be administered to a human recipient prior to implantation of a graft or implantation of an organ, tissue, or cells that are matched with respect to the donor hemangio-colony forming cells. The human hemangio-colony forming cells and graft may be obtained from the same donor. The graft may be derived from differentiated donor human hemangio-colony forming cells. The human hemangio-colony forming cells and graft may alternatively be obtained from different donors wherein the donors are matched. The human hemangio-colony forming cells may be administered to human recipients to induce tolerance in recipients in need thereof.

In certain embodiments, the present invention relates to a method of inducing tolerance in a human recipient to a donor allograft, wherein the method comprises the steps of (a) administering to the recipient an agent that inhibits T cell co-stimulation (b) introducing into the recipient human hemangio-colony forming cells that are generated and expanded, or expanded, according to the methods described herein, and (c) implanting the allograft into the recipient. The human hemangio-colony forming cells (donor cells) promote acceptance of the allograft by the recipient. In certain embodiments, an agent that inhibits T cell costimulation is an agent that inhibits or blocks the CD40 ligand-CD40 costimulatory interaction. The method may further comprise administering an agent that inhibits the CD28-B7 interaction. The method may or may not comprise thymic irradiation and/or T cell depletion or inactivation. The aforementioned method may also produce mixed chimerism in the absence of hematopoietic space created by whole body irradiation.

The invention also provides for a method of promoting tolerance in a human recipient to a donor allograft, wherein the method comprises the steps of (a) creating thymic space in said recipient; (b) depleting or inactivating donor-reactive T cells in said recipient; (c) introducing donor human hemangio-colony forming cells of said donor or that are matched to said donor into said recipient; and (d) implanting said allograft into said recipient, wherein the donor hemangio-colony forming cells induce tolerance to the allograft. In certain embodiments, the method does not comprise hematopoietic space-creating irradiation. The method may comprise creating thymic space by administering to the recipient at least one treatment selected from among thymic irradiation (which can be fractionated), steroids, corticosteroids, brequinar, or an immune suppressant or drug.

The invention also provides methods for generating cells suitable for use in blood transfusion. For example, the invention provides methods for generating red blood cells that can be used in transfusion. As such, the present invention provides a solution to help alleviate the chronic shortage of blood available for donation.

In certain embodiments, the present invention provides a method for producing differentiated hematopoietic cells from human hemangio-colony forming cells in vitro, said method comprising the steps of:
(a) providing human hemangio-colony forming cells; and
(b) differentiating said hemangio-colony forming cells into differentiated hematopoietic cells.

In certain embodiments, the present invention provides a method for performing blood transfusions using hematopoietic cells differentiated in vitro from human hemangio-colony forming cells, said method comprising the steps of:
(a) providing human hemangio-colony forming cells;
(b) differentiating said hemangio-colony forming cells into differentiated hematopoietic cells; and
(c) performing blood transfusions with said differentiated hematopoietic cells.

In certain embodiments, said hemangio-colony forming cells are recovered from frozen cultures.

In certain embodiments, the present invention provides a method for performing blood transfusions using hematopoietic cells differentiated in vitro from human hemangio-colony forming cells, said method comprising the steps of:
(a) culturing a cell culture comprising human embryo-derived cells in the presence of at least one growth factor in an amount sufficient to induce the differentiation of said embryo-derived cells into embryoid bodies;
(b) adding at least one growth factor to said culture comprising embryoid bodies, wherein said growth factor is in an amount sufficient to expand human hemangio-colony forming cells in said embryoid bodies culture;
(c) differentiating said hemangio-colony forming cells into differentiated hematopoietic cells; and
(d) performing blood transfusions with said differentiated hematopoietic cells.

In certain embodiments, said embryo-derived cells, embryoid bodies and hemangio-colony forming cells are grown in serum-free media throughout step (a) of said method.

In certain embodiments, the embryo-derived cell is an embryonic stem cell.

In certain embodiments, the present invention provides a method for performing blood transfusions using hematopoietic cells differentiated in vitro from human hemangio-colony forming cells, said method comprising the steps of:
(a) culturing a cell culture comprising human embryo-derived cells in the presence of at least one growth factor in an amount sufficient to induce the differentiation of said embryo-derived cells into embryoid bodies;
(b) adding at least one growth factor to said culture comprising embryoid bodies, wherein said growth factor is in an amount sufficient to expand human hemangio-colony forming cells in said embryoid bodies culture;
(c) differentiating said hemangio-colony forming cells into differentiated hematopoietic cells; and
(d) performing blood transfusions with said differentiated hematopoietic cells.

In certain embodiments, said stem cells, embryoid bodies and hemangio-colony forming cells are grown in serum-free media throughout steps (a) and (b) of said method.

In certain embodiments of the invention, the embryo-derived cell is an embryonic stem cell.

In certain embodiments, said hemangio-colony forming cells are recovered from frozen cultures.

In certain embodiments, the present invention provides a method for performing blood transfusions using hematopoietic cells differentiated in vitro from human hemangio-colony forming cells, said method comprising the steps of:
(a) culturing a cell culture comprising human embryo-derived cells in the presence of at least one growth factor in an amount sufficient to induce the differentiation of said embryo-derived cells into embryoid bodies;
(b) adding at least one growth factor to said culture comprising embryoid bodies, wherein said growth factor is in an amount sufficient to expand human hemangio-colony forming cells in said embryoid bodies culture;
(c) disaggregating said embryoid bodies into single cells;

(d) adding at least one growth factor to said culture comprising said single cells, wherein said growth factor is in an amount sufficient to expand human hemangio-colony forming cells in said culture comprising said single cells;

(e) differentiating said hemangio-colony forming cells into differentiated hematopoietic cells; and (f) performing blood transfusions with said differentiated hematopoietic cells.

In certain embodiments, said stem cells, embryoid bodies and hemangio-colony forming cells are grown in serum-free media throughout steps (a)-(d) of said method.

In certain embodiments of the invention, the embryo-derived cell is an embryonic stem cell.

In certain embodiments, the growth factor is a protein that comprises a homeobox protein, or a functional variant or an active fragment thereof. In certain embodiments, the homeobox protein comprises a HOXB4 protein, or a functional variant or an active variant thereof.

In certain embodiments, the differentiated hematopoietic cells are produced as a single cell type. In certain embodiments, the single cell type is selected from: red blood cells, platelets, or phagocytes. In certain embodiments, the phagocyte is selected from: granulocytes: neutrophils, basophils, eosinophils, lymphocytes or monocytes. In certain embodiments, wherein the red blood cells express hemoglobin F. In certain embodiments, the single cell types are mixed to approximately equal the proportion of differentiated cell types that is found in blood, wherein the proportion of differentiated cell types that is found in blood is 96% red blood cells, 1% platelets, and 3% phagocytes.

In certain embodiments, multiple differentiated hematopoietic cell types are produced in the same step. In certain embodiments, the multiple differentiated hematopoietic cell types are selected from: red blood cells, platelets, or phagocytes. In certain embodiments, the phagocyte is selected from: granulocytes: neutrophils, basophils, eosinophils, lymphocytes or monocytes. In certain embodiments, the red blood cells express hemoglobin F. In certain embodiments, the multiple differentiated hematopoietic cell types are produced in a proportion approximately equal to the proportion of differentiated hematopoietic cell types found in blood, wherein the proportion of differentiated cell types that is found in blood is 96% red blood cells, 1% platelets, and 3% phagocytes.

In certain embodiments, plasma is added to the differentiated hematopoietic cells before transfusion.

In certain embodiments, the hemangio-colony forming cells are matched to a patient to ensure that differentiated hematopoietic cells of the patient's own blood type are produced. In certain embodiments, the hemangio-colony forming cells are negative for antigenic factors A, B, Rh, or any combination thereof. In certain embodiments, the differentiated hematopoietic cells are red blood cells, and wherein a step of differentiating the red blood cells includes erythropoietin (EPO).

The invention also provides a human hemangio-colony forming cell, which cell can differentiate to produce at least hematopoietic or endothelial cell types, wherein the human hemangio-colony forming cell is loosely adherent to other human hemangio-colony forming cells.

In certain embodiments, the invention provides a human hemangio-colony forming cell, which cell can differentiate to produce at least hematopoietic and endothelial cell types, wherein the human hemangio-colony forming cell is loosely adherent to other human hemangio-colony forming cells.

In certain embodiments, the invention provides a human hemangio-colony forming cell, which cell can differentiate to produce at least hematopoietic and endothelial cell types, wherein the human hemangio-colony forming cell is loosely adherent to other human hemangio-colony forming cells, and wherein the human hemangio-colony forming cell does not express CD34 protein.

In certain embodiments, the invention provides a human hemangio-colony forming cell, which cell can differentiate to produce at least hematopoietic and endothelial cell types, wherein the human hemangio-colony forming cell does not express any of the following proteins: CD34, CD31, KDR, and CD133.

In certain embodiments, the invention provides a cell culture comprising human hemangio-colony forming cells, which cells can differentiate to produce at least hematopoietic or endothelial cell types, wherein the hemangio-colony forming cells are loosely adherent to each other.

In certain embodiments, the invention provides a cell culture comprising human hemangio-colony forming cells, which cells can differentiate to produce at least hematopoietic and endothelial cell types, wherein the hemangio-colony forming cells are loosely adherent to each other.

In certain embodiments, the invention provides a cell culture comprising a substantially purified population of human hemangio-colony forming cells, which cells can differentiate to produce at least hematopoietic and endothelial cell types, wherein the hemangio-colony forming cells are loosely adherent to each other, and wherein the hemangio-colony forming cells do not express CD34 protein.

In certain embodiments, the invention provides a cell culture comprising human hemangio-colony forming cells differentiated from embryo-derived cells, wherein the hemangio-colony forming cells are loosely adherent to each other.

In certain embodiments, the cell culture comprises at least $1 \times 10^6$ human hemangio-colony forming cells. In certain embodiments, the cell culture comprises at least $5 \times 10^6$ human hemangio-colony forming cells.

In certain embodiments, the embryo-derived cell is an embryonic stem cell line. In certain embodiments, the embryo-derived cell is selected from an embryo, a blastomere, a blastocyst, or an inner cell mass.

In certain embodiments, the invention provides a pharmaceutical preparation comprising human hemangio-colony forming cells, which cells can differentiate to produce at least hematopoietic or endothelial cell types, wherein the hemangio-colony forming cells are loosely adherent to each other.

In certain embodiments, the invention provides a pharmaceutical preparation comprising human hemangio-colony forming cells, which cells can differentiate to produce at least hematopoietic and endothelial cell types, wherein the hemangio-colony forming cells are loosely adherent to each other.

In certain embodiments, the invention provides a pharmaceutical preparation comprising human hemangio-colony forming cells, which cells can differentiate to produce at least hematopoietic and endothelial cell types, wherein the hemangio-colony forming cells do not express any of the following proteins: CD34, CD31, KDR, and CD133.

In certain embodiments, the pharmaceutical preparation comprises at least $1 \times 10^6$ human hemangio-colony forming cells. In certain embodiments, the preparation comprises at least $5 \times 10^6$ human hemangio-colony forming cells.

In certain embodiments, the pharmaceutical preparation comprising hemangio-colony forming cells are differentiated from embryo-derived cells. In certain embodiments, the embryo-derived cell is an embryonic stem cell. In certain embodiments, the embryo-derived cell is selected from an embryo, a blastomere, a blastocyst, or an inner cell mass.

In certain embodiments, the invention provides a cryopreserved preparation of the hemangio-colony forming cells described in any of the preceding paragraphs.

In certain embodiments, the invention provides a cryopreserved preparation of at least $1 \times 10^6$ human hemangio-colony forming cells, wherein the hemangio-colony forming cells do not express any of the following proteins: CD34, CD31, KDR, and CD133.

In certain embodiments, the cryopreserved preparation comprises at least $5 \times 10^6$ human hemangio-colony forming cells.

In certain embodiments, the cryopreserved preparation comprising human hemangio-colony forming cells do not express CD34 protein. In certain embodiments, the cryopreserved preparation comprising human hemangio-colony forming cells do not express CD34, CD31, CD133, and KDR proteins. In certain embodiments, the cryopreserved preparation comprising human hemangio-colony forming cells express LMO2 and GATA2 proteins.

In certain embodiments, the invention provides a culture comprising a hematopoietic cell differentiated from the hemangio-colony forming cells as described above.

In certain embodiments, the invention provides a culture comprising an endothelial cell differentiated from the hemangio-colony forming cells as described above.

In certain embodiments, the invention provides a culture comprising a smooth muscle cell differentiated from the hemangio-colony forming cells as described above.

In certain embodiments, the invention provides a culture comprising a cardiomyocyte differentiated from the hemangio-colony forming cells as described above.

In certain embodiments, the invention provides for the use of the human hemangio-colony forming cells as described above in the manufacture of a medicament to treat a condition in a patient in need thereof.

In certain embodiments, the invention provides the use of the cell culture as described above in the manufacture of a medicament to treat a condition in a patient in need thereof.

In certain embodiments, the invention provides the use of the pharmaceutical preparation as described above in the manufacture of a medicament to treat a condition in a patient in need thereof.

The invention contemplates combinations of any of the foregoing aspects and embodiments of the invention.

BRIEF DESCRIPTION OF THE DRAWINGS

FIG. 1 illustrates the hematopoietic CFUs derived from hemangioblasts generated from H1-GFP ES cells.

FIG. 2 illustrates the cell morphology of the erythroid colony forming units (CFU-E) cultured in serum-free (Stemline) culture media.

FIG. 3 illustrates the cell morphology of the multipotent colony forming units (CFU-GEMM/Mix) cultured in serum-free (Stemline) culture media.

FIG. 4 illustrates the cell morphology of the multipotent colony forming units (CFU-GEMM/Mix) cultured in serum-free (Stemline) culture media.

FIG. 5 illustrates the cell morphology of the granulocyte colony forming units (CFU-G) and macrophage colony forming units (CFU-M) cultured in serum-free (Stemline) culture media.

FIG. 6 illustrates the cell morphology of the granulocyte/macrophage colony forming units (CFU-GM) and megakaryotcye macrophage colony forming units (CFU-Mk) cultured in serum-free (Stemline) culture media.

FIG. 8 illustrates the tube-cord structure of hemangioblasts generated from H1-GFP ES cells that were cultured on fibronectin-coated plates in EGM-2 media and then on Matrigel, as described in Example 2. FIG. 8 also illustrates the uptake of Ac-LDL by the cells when incubated with Alexa fluor labeled Ac-LDL, as described in Example 2. The middle top and right top panels show phase contrast pictures.

FIG. 9 illustrates the expression of von Willebrand factor (vWF) (light gray staining) in hemangioblasts generated from H1-GFP ES cells that were cultured on fibronectin-coated plates in EGM-2 media, as described in Example 2.

FIG. 10 illustrates the formation of vessels in cross-sections of haematoxylin and eosin (H&E)-stained Matrigel plugs that were injected into SCID mice, as described in Example 4.

FIG. 11 illustrates that the vessels from the cross-sections of Matrigel plugs are cells derived from human hemangioblasts, as indicated by the positive staining for human specific nuclei antibody (light gray staining), as described in Example 4.

FIG. 12 illustrates the mRNA sequence of human HOXB4 (Accession No. NM_024015.4; GI: 85376187) (SEQ ID NO: 2).

FIG. 13 illustrates the amino acid sequence of human HOXB4 (Accession No. NP_076920.1; GI: 13273315) (SEQ ID NO: 1).

FIG. 14 illustrates the mRNA sequence of human HOXB4 (Accession No. BC049204.1; GI: 29351567) (SEQ ID NO: 4).

FIG. 15 illustrates the amino acid sequence of human HOXB4 (Accession No. AAH49204.1; GI: 29351568) (SEQ ID NO: 3).

FIGS. 16a-16v illustrate the phenotypic characterization of hemangioblasts (BL-CFC) derived from human ES cells: 16a hemangioblast colony or blast colony (BL-CFC or BC, ×400); 16b Secondary EBs (×400); 16c Blast cells (hES-BC cells) with Wright-Giemsa staining (×1000); 16d-16f: GATA-1 staining; 16d blast cells stained with GATA-1 (×600) and 16e GATA-1 and DAPI; 16f BM cells stained with GATA-1 and DAPI (×400). 16g-16i: LMO2 staining; 16g blast cells stained with LMO2 (×600) and 16h LMO2 and DAPI (×600); 16i K562 cells stained with LMO2 and DAPI (×1000); 16j-16m: CD71 staining (bright or light gray); 16j blast cells stained with CD71 (×600) and 16k CD71 and DAPI (×600); 16m BM cells stained with CD71 and DAPI (×1000); 16n-16p: CXCR-4 staining (bright or light gray); 16n blast cells stained with CXCR-4 (×600) and 16o CXCR- and DAPI (×600); 16p BM cells stained with CXCR-4 and DAPI (×600); 16q-16s Epo-receptor staining (medium gray); 16q blast cells stained with Epo-receptor (×600) and 16r Epo-receptor and DAPI (×600); 16s BM cells stained with Epo-receptor and DAPI (×600); 16t-16v Tpo-receptor staining (medium gray); 16t blast cells stained with Tpo-receptor (×600) and 16u Tpo-receptor and DAPI (×600); 16v BM cells stained with Tpo-receptor and DAPI (×1000), as described in Examples 1 and 2. Note: hES-BC (hemangioblast) cells in panels 16d and 16n were double stained with GATA-1 and CXCR-4 antibodies, but presented separately; hES-BC (hemangioblast) cells in panels 16q and 16t were also double stained with Epo-receptor and Tpo-receptor antibodies and presented separately.

FIGS. 18a-18m show the clonogenicity of blast colonies derived from hES cells. 18a-18c: Clonogenicity of blast colonies. 18a and 18b, two blast colonies developed in a mixture of WA01-GFP and MA01 EBs, which demonstrated the clonal origin of the blast colonies; 18a phase image (×100); 18b GFP image (×100); 18c blast colony developed from a single cell (×400). 18d and 18e: Expansion of single blast colony in liquid culture, both hematopoietic and endothelial lineages were observed (×200). 18d, ×200 18e, ×400; 18f-18h: Endothelial cells derived from a single BC: 18f Capillary tube-like structures formed on Matrigel after plating adherent cells derived from a single BC (×100); 18g Ac-LDL uptake (arrows) by endothelial cells derived from a single BC, nuclei were stained with DAPI (×400); 18h Expression of vWF (arrows) in a single BC-derived endothelial cells, nuclei were stained with DAPI (×400). 18i-18m: Hematopoietic CFUs derived from a single BC: 18i CFU-erythroid (×100); 18j CFU-granulocyte (×100); 18k CFU-macrophage (×100); and 18l CFU-multilineage (mix, ×100). 18m The gel shows the results of a PCR analysis of GFP sequences in GFP+ and GFP− hES-BCs (hemangioblast) derived from plating mixtures of WA01-GFP+ and MA01-GFP− cells. Lanes: WA01-GFP+, parental WA01/GFP+ hES cells; MA01-GFP−, parental MA01 hES cells; H₂O, water negative control; BC-GFP+, GFP positive BC picked up from cell-mixing plating; 1-10, GFP negative BCs picked up from cell-mixing plating. A myogenin gene was used for a PCR reaction control. See Example 2.

FIGS. 19a-19c provide a characterization of a tPTD-HOXB4 fusion protein. 19a 6×His-fused tPTD-HOXB4 recombinant protein was expressed in E. coli and purified by nickel ProBand resins. Two batches (designated as (1) and (2)) of desalted tPTD-HOXB4 protein was examined for its purity and concentration by SDS-PAGE gel. 19b tPTD-HOXB4 protein is unstable in medium with 5% FBS but 19c retains its integrity in serum free medium with live ES cells (N=stemline II medium only; h=hours).

FIGS. 20a-20f illustrate the robust repair of ischemic retinal vasculature after systematic injection with hES-derived hemangioblasts. Retinal ischemia was induced by 2 h of hydrostatic pressure on the anterior chamber of mouse eyes. Seven days later fluorescently labeled (GFP+) hemangioblasts were injected either intravitreally or intravenously. One day later the animals were euthanized. Eyes were enucleated, dissected, and the retinas were mounted flat and imaged by laser scanning confocal microscopy or sectioned for imaging. 20a a merge from a typical control (uninjured) eye showing typical retinal vascular anatomy with no background green fluorescence; separate GFP+(bottom inset) and GFP− (top inset) channels are also shown; 20b a merge from the treated eye of the same animal showing fluorescently labeled (GFP+) hemangioblast-derived cells (bright areas of the vasculature) incorporated into the ischemic vasculature; separate green (GFP+ hemangioblasts, bottom inset) and unlabeled cells (top inset) are also shown), as described in Example 5; 20c a merge from uninjured control (no GFP (bright or light gray) fluorescence), 20d and 20e are merges from the ischemic eyes 2 days 20d and 7 days 20e after systemic hemangioblast administration (GFP+ cells appear as bright or light gray). (20f, ×600, confocal), fluorescent immunocytochemistry colocalizes hemangioblast (hES-BC) cell-derived endothelial cells to existing injured vasculature in cross sections of mouse eyes that underwent I/R injury; a high magnification view of a vascular lumen in the ganglion cell layer adjacent to the inner limiting membrane shows the lumen surrounded by endothelial cells (arrowhead, CD31) and also by mature endothelial cell(s) derived from hemangioblast (hES-BC) cells (arrow, human nuclear antigen). Inset upper and middle panels are the separate human nuclear antigen and CD31 channels that were used to make the composite image. Lower panel is a lower magnification of the same region, with the box showing the area depicted in all panels. V=vitreous; IPL=inner plexiform layer; RPE=retinal pigment epithelial cell layer; Ch=choroid. See Example 5.

FIGS. 21a-21f show the incorporation of hemangioblasts, or blast cells or hES-BC cells, into the retinal vasculature of diabetic rats. 21a and 21b show merged retinal vasculature images from diabetic rats 2 days after intravitreal hemangioblast administration, showing extensive hemangioblast incorporation (bright or light gray areas) into both large and small vessels; 21c, a merge from a control (non-diabetic) rat 2 days after hemangioblast administration, showing that hemangioblasts (or hemangioblast-derived cells) did not incorporate into vasculature and formed a sheet that lay on top of the retina (light gray layer). (21d, ×100), a section from a non-diabetic control rat 2 days after intravitreal blast cell injection, which is negative for human nuclear antigen staining, but is clearly positive for endothelium (CD31, arrows). (21e, ×100) and (21f, −×600, confocal) are rat eye sections from diabetic rats 2 days after intravitreal hemangioblast injection, and stained with CD31 and human nuclear antigen antibodies, which clearly show colocalized staining with CD31 and human nuclear antigen in cells lining vessel lumens in the ganglion cell layer of the retina, immediately posterior to the internal limiting membrane that separates the neural retina from the vitreous (arrows pointing to bright areas). See Example 6.

FIGS. 22a-22i show endothelial differentiation in ischemic hind limb muscle and infarcted heart after injection of hemangioblasts. 22a, 22b, 22h and 22i: Differentiation of hemangioblasts or hES-BC cells in infarcted hearts. (22a (200×)), infarcted myocardium section from control mouse immunostained with human specific vWF antibody, showing no stain of human vWF; (22b, 200×) and (22i, ×600 confocal), infracted myocardium section 4 weeks after injection of hemangioblasts, immunostained with human specific vWF antibody (light gray or bright areas in 22b and 22i); 22h the survival curves of mice treated with sham operation, medium control, and hemangioblasts. 22c-22g: Differentiation of hemangioblasts in ishemic hind limb muscles. 22c, 50×), a hind limb muscle section from control mouse immunostained with human specific vWF antibody, showing no stain of human vWF; (22d, 50×) and (22e, 600×, confocal), ischemic hind limb muscle sections 4 weeks after injection of hemangioblasts, immunostained with human specific vWF antibody (light gray); 22f restoration of blood flow to surgically induced ischemic limbs. Hind limb blood flow monitored serially for 3-30 days after ligation in mouse receiving $6 \times 10^5$ hemangioblasts and in mouse with medium only. Blood flow is calculated as the ratio of flow in the ischemic limb to that in the non-ischemic limb; 22g, laser Doppler blood flow images. Images of controls (medium) and ischemic animals injected with BC cells (n=6 for each group). See Examples 7 and 8.

FIG. 23 shows immunostaining of GFP (the lightest or brightest areas) and cTnI (medium gray) on heart tissue sections from myocardial infarcted (MI) mice (magnification 200×). See Example 8. The arrows indicate double positive staining cells derived from injected hemangioblast (hES-BC) cells.

DETAILED DESCRIPTION OF THE INVENTION

Figure 7A:
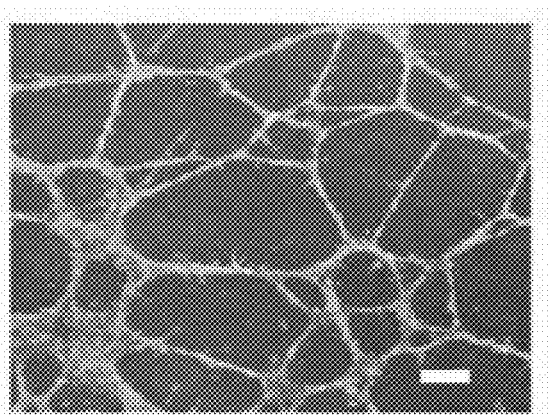
FIGS. 7a-7b illustrate formation of tube-cord structures following the replating of hemangioblasts derived from 7a H9 ES cells and 7b ACT30 ES cells on Matrigel-based medium.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

All publications, patents, patent publications and applications and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

In order to further define the invention, the following terms and definitions are provided herein.

The term "human embryonic stem cells" (hES cells) is used herein as it is used in the art. This term includes cells derived from the inner cell mass of human blastocysts or morulae that may be serially passaged as cell lines. The hES cells may be derived from fertilization of an egg cell with sperm or DNA, nuclear transfer, parthenogenesis, or by means to generate hES cells with homozygosity in the HLA region. Human ES cells are also cells derived from a zygote, blastomeres, or blastocyst-staged mammalian embryo produced by the fusion of a sperm and egg cell, nuclear transfer, parthenogenesis, or the reprogramming of chromatin and subsequent incorporation of the reprogrammed chromatin into a plasma membrane to produce a cell. Human embryonic stem cells of the present invention may include, but are not limited to, ACT-4, No. 3, H1, H7, H9, H14 and ACT30 embryonic stem cells.

The term "protein transduction domain" ("PTD") refers to any amino acid sequence that translocates across a cell membrane into cells or confers or increases the rate of, for example, another molecule (such as, for example, a protein domain) to which the PTD is attached, to translocate across a cell membrane into cells. The protein transduction domain may be a domain or sequence that occurs naturally as part of a larger protein (e.g., a PTD of a viral protein such as HIV TAT) or may be a synthetic or artificial amino acid sequence.

Overview

This invention provides a method for generating and expanding human hemangio-colony forming cells from human embryo-derived cells, preparations and compositions comprising human hemangio-colony forming cells, methods of producing various cell types partially or terminally differentiated from hemangio-colony forming cells, methods of using hemangio-colony forming cells therapeutically, and methods of therapeutically using various cell types partially or terminally differentiated from hemangio-colony forming cells.

The terms "hemangioblast" and "hemangio-colony forming cells" will be used interchangeably throughout this application. These cells can be described based on numerous structural and functional properties including, but not limited to, expression (RNA or protein) or lack of expression (RNA or protein) of one or more markers. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

This invention also provides a method for expanding mammalian hemangio-colony forming cells obtained from any source, including ES cells, blastocysts or blastomeres, cord blood from placenta or umbilical tissue, peripheral blood, bone marrow, or other tissue or by any other means known in the art. Human hemangio-colony forming cells can also be generated from human embryo-derived cells. Human embryo-derived cells may be a substantially homogeneous population of cells, a heterogeneous populations of cells, or all or a portion of an embryonic tissue. As an example of embryo-derived cells that can be used in the methods of the present invention, human hemangio-colony forming cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

In certain embodiments, hemangioblasts can be further differentiated to hematopoietic cells including, but not limited to, platelets and red blood cells. Such cells may be used in transfusions. The ability to generate large numbers of cells for transfusion will alleviate the chronic shortage of blood experienced in blood banks and hospitals across the country. In certain embodiments, the methods of the invention allow for the production of universal cells for transfusion. Specifically, red blood cells that are type O and Rh− can be readily generated and will serve as a universal blood source for transfusion.

The methods of this invention allow for the in vitro expansion of hemangioblasts to large quantities useful for a variety of commercial and clinical applications. Expansion of hemangioblasts in vitro refers to the proliferation of hemangioblasts. While the methods of the invention enable the expansion of human hemangioblast cells to reach commercially useful quantities, the present invention also relates to large numbers of hemangioblast cells and to cell preparations comprising large numbers of human hemangioblast cells (for example, at least 10,000, 100,000, or 500,000 cells). In certain embodiments, the cell preparations comprise at least $1 \times 10^6$ cells. In other embodiments, the cell preparations comprise at least $2 \times 10^6$ human hemangioblast cells and in further embodiments at least $3 \times 10^6$ human hemangioblast cells. In still other embodiments, the cell preparations comprise at least $4 \times 10^6$ human hemangioblast cells.

The present invention relates to a solution, a preparation, and a composition comprising between 10,000 to 4 million or more mammalian (such as human) hemangioblast cells. The number of hemangioblast cells in such a solution, a preparation, and a composition may be any number between the range of 10,000 to 4 million, or more. This number could be, for example, 20,000, 50,000, 100,000, 500,000, 1 million, etc.

Similarly, the invention relates to preparations of human hemangioblast progeny cells (e.g., human hematopoietic cells including human hematopoietic stem cells, and endothelial cells). The invention further relates to methods of producing, storing, and distributing hemangioblast cells and/or hemangioblast lineage cells.

The invention also provides methods and solutions suitable for transfusion into human or animal patients. In particular embodiments, the invention provides methods of making red blood cells and/or platelets, and/or other hematopoietic cell types for transfusion. In certain embodiments, the invention is suitable for use in blood banks and hospitals to provide blood for transfusion following trauma, or in the treatment of a blood-related disease or disorder. In certain embodiments, the invention provides red blood cells that are universal donor cells. In certain embodiments, the red blood cells are functional and express hemoglobin F prior to transfusion.

The invention also provides for human hemangio-colony forming cells, cell cultures comprising a substantially purified population of human hemangio-colony forming cells, pharmaceutical preparations comprising human hemangio-colony forming cells and cryopreserved preparations of the hemangio-colony forming cells. In certain embodiments, the invention provides for the use of the human hemangio-colony forming cells in the manufacture of a medicament to treat a condition in a patient in need thereof. Alternatively, the invention provides the use of the cell cultures in the manufacture of a medicament to treat a condition in a patient in need thereof. The invention also provides the use of the pharmaceutical preparations in the manufacture of a medicament to treat a condition in a patient in need thereof.

The hemangio-colony forming cells can be identified and characterized based on their structural properties. Specifically, and in certain embodiments, these cells are unique in that they are only loosely adherent to each other (loosely adherent to other hemangio-colony forming cells). Because these cells are only loosely adherent to each other, cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination of mechanical and enzymatic dissociation, is sufficient to disaggregate the cultures or colonies without substantially impairing the viability of the cells. In other words, mechanical dissociation does not require so much force as to cause substantial cell injury or death when compared to that observed subsequent to enzymatic dissociation of cell aggregates.

Furthermore, hemangio-colony forming cells can be identified or characterized based on the expression or lack of expression (as assessed at the level of the gene or the level of the protein) of one or more markers. For example, in certain embodiments, hemangio-colony forming cells can be identified or characterized based on lack of expression of one or more (e.g., the cells can be characterized based on lack of expression of at least one, at least two, at least three or at least four of the following markers) of the following cell surface markers: CD34, KDR, CD133, or CD31. Additionally or alternatively, hemangio-colony forming cells can be identified or characterized based on expression of GATA2 and/or LMO2. Additionally or alternatively, hemangio-colony forming cells can be identified or characterized based on expression or lack of expression (as assessed at the level of the gene or the level of the protein) of one or more markers analyzed in Table 2.

Hemangio-colony forming cells of the present invention can be identified or characterized based on one or any combination of these structural or functional characteristics. Note that although these cells can be derived from any of a number of sources, for example, embryonic tissue, prenatal tissue, or perinatal tissue, the term "hemangio-colony forming cells" applies to cells, regardless of source, that are capable of differentiating to give rise to at least hematopoietic cell types and/or endothelial cell types and that have one or more of the foregoing structural or functional properties.

In Vitro Differentiation of Human Embryonic Stem Cells to Obtain Embryoid Bodies and Hemangioblasts The present invention provides a method for generating and expanding human hemangioblasts derived from human embryonic stem cells, or from human blastocysts or blastomeres. The hemangioblasts so produced may be purified and/or isolated.

Human hemangio-colony forming cells can also be generated from human embryo-derived cells. Human embryo-derived cells may be a substantially homogeneous population of cells, a heterogeneous populations of cells, or all or a portion of an embryonic tissue. As an example of embryo-derived cells that can be used in the methods of the present invention, human hemangio-colony forming cells can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

Additionally or alternatively, hemangio-colony forming cells can be generated from other embryo-derived cells. For example, hemangio-colony forming cells can be generated (without necessarily going through a step of embryonic stem cell derivation) from or using plated embryos, ICMs, blastocysts, trophoblast/trophectoderm cells, one or more blastomeres, trophoblast stem cells, embryonic germ cells, or other portions of a pre-implantation-stage embryo or embryo-like structure, regardless of whether produced by fertilization, somatic cell nuclear transfer (SCNT), parthenogenesis, androgenesis, or other sexual or asexual means. Similarly, hemangio-colony forming cells can be generated using cells or cell lines partially differentiated from embryo-derived cells. For example, if a human embryonic stem cell line is used to produce cells that are more developmentally primitive than hemangio-colony forming cells, in terms of development potential and plasticity, such embryo-derived cells could then be used to generate hemangio-colony forming cells.

Additionally or alternatively, hemangio-colony forming cells can be generated from other pre-natal or peri-natal sources including, without limitation, umbilical cord, umbilical cord blood, amniotic fluid, amniotic stem cells, and placenta.

It is noted that when hemangio-colony forming cells are generated from human embryonic tissue a step of embryoid body formation may be needed. However, given that embryoid body formation serves, at least in part, to help recapitulate the three dimensional interaction of the germ layers that occurs during early development, such a step is not necessarily required when the embryo-derived cells already have a structure or organization that serves substantially the same purpose as embryoid body formation. By way of example, when hemangio-colony forming cells are generated from plated blastocysts, a level of three dimensional organization already exists amongst the cells in the blastocyst. As such, a step of embryoid body formation is not necessarily required to provide intercellular signals, inductive cues, or three dimensional architecture.

The methods and uses of the present invention can be used to generate hemangio-colony forming cells from embryo-derived cells. In certain embodiments, the embryo-derived cells are embryonic stem cells. In certain other embodiments, the embryo-derived cells are plated embryos, ICMs, blastocysts, trophoblast/trophectoderm cells, one or more blastomeres, trophoblast stem cells, or other portions of an early pre-implantation embryo. For any of the foregoing, the embryo-derived cells may be from embryos produced by fertilization, somatic cell nuclear transfer (SCNT), parthenogenesis, androgenesis, or other sexual or asexual means.

Throughout this application, when a method is described by referring specifically to generating hemangio-colony forming cells from embryonic stem cells, the invention similarly contemplates generating hemangio-colony forming cells from or using other embryonic-derived cells, and using the generated cells for any of the same therapeutic applications.

In certain aspects of the invention, the human embryonic stem cells may be the starting material of this method. The embryonic stem cells may be cultured in any way known in the art, such as in the presence or absence of feeder cells.

Embryonic stem cells may form embryoid bodies ("EBs") in suspension in medium containing serum (Wang et al. 2005 J Exp Med (201):1603-1614; Wang et al. 2004 Immunity (21): 31-41; Chadwick et al. 2003 Blood (102): 906-915). The addition of serum, however, presents certain challenges, including variability in experiments, cost, the potential for infectious agents, and limited supply. Further, for clinical and certain commercial applications, use of serum necessitates additional U.S. and international regulatory compliance issues that govern biological products.

The present invention provides methods of generating and expanding human hemangioblasts from embryonic stem cells in which no serum is used. The serum-free conditions are more conducive to scale-up production under good manufacturing process (GMP) guidelines than are conditions which require serum. Furthermore, serum-free conditions extend the half-life of certain factors added to the medium (for example, the half-life of proteins including growth factors, cytokines, and HOXB4 in media is increased when no serum is present). In certain embodiments, serum-free media is used throughout the method of this invention for generating and expanding human hemangioblasts.

In the first step of this method for generating and expanding human hemangioblast cells, human stem cells are grown in serum-free media and are induced to differentiate into embryoid bodies. To induce embryoid body formation, embryonic stem cells may be pelleted and resuspended in serum-free medium (e.g., in Stemline I or II media (Sigma™)) supplemented with one or more morphogenic factors and cytokines and then plated on low attachment (e.g., ultra-low attachment) culture dishes. Morphogenic factors and cytokines may include, but are not limited to, bone morphogenic proteins (e.g., BMP2, BMP-4, BMP-7, but not BMP-3) and VEGF, SCF and FL. Bone morphogenic proteins and VEGF may be used alone or in combination with other factors. The morphogenic factors and cytokines may be added to the media from 0-48 hours of cell culture. Following incubation under these conditions, incubation in the presence of early hematopoietic expansion cytokines, including, but not limited to, thrombopoietin (TPO), Flt-3 ligand, and stem cell factor (SCF), allows the plated ES cells to form EBs. In addition to TPO, Flt-3 ligand, and SCF, VEGF, BMP-4, and HoxB4 may also be added to the media. In one embodiment, human ES cells are first grown in the presence of BMP-4 and VEGF$_{165}$ (e.g., 25-100 ng/ml), followed by growing in the presence of BMP-4, VEGF$_{165}$, SCF, TPO, and FLT3 ligand (e.g., 10-50 ng/ml) and HoxB4 (e.g., 1.5-5 µg/ml of a triple protein transduction domain-HoxB4 fusion protein as disclosed herein). The additional factors may be added 48-72 hours after plating.

In this method of the present invention, human hemangioblast cells are isolated from early embryoid bodies ("EBs"). Isolating hemangioblast cells from early EBs supports the expansion of the cells in vitro. For human cells, hemangioblast cells may be obtained from EBs grown for less than 10 days. In certain embodiments of the present invention, hemangioblast cells arise in human EBs grown for 2-6 days. According to one embodiment, hemangioblast cells are identified and may be isolated from human EBs grown for 4-6 days. In other embodiments, human EBs are grown for 2-5 days before hemangioblast cells are isolated. In certain embodiments, human EBs are grown for 3-4.5 days before hemangioblast cells are isolated.

In certain embodiments, early EBs are washed and dissociated (e.g., by Trypsin/EDTA or collagenase B). A select number of cells (e.g., 2-5×10$^5$ cells) are then mixed with serum-free methylcellulose medium optimized for hemangioblast cell growth (e.g., BL-CFU medium, for example Stem Cell Technologies Catalogue H4436, or hemangioblast cell expansion medium (HGM), or any medium containing 1.0% methylcellulose in MDM, 1-2% Bovine serum albumin, 0.1 mM 2-mercaptoethanol, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF) ("rh" stands for "recombinant human"). This medium may be supplemented with early stage cytokines (including, but not limited to, EPO, TPO, SCF, FL, FLt-3, VEGF, BMPs such as BMP2, BMP4 and BMP7, but not BMP3) and HOXB4 (or another homeobox protein). In certain embodiments, erythropoietin (EPO) is added to the media. In further embodiments, EPO, SCF, VEGF, BMP-4 and HoxB4 are added to the media. In additional embodiments, the cells are grown in the presence of EPO, TPO and FL. In certain embodiments where H9 is the starting human ES cell line, EPO, TPO and FL are added to the media. In addition to EPO, TPO and FL, media for cells derived from H9 or other ES cells may further comprise VEGF, BMP-4, and HoxB4.

The cells so obtained by this method (the cells may be in BL-CFU medium), which include hemangioblast cells, are plated onto ultra-low attachment culture dishes and incubated in a CO$_2$ incubator to grow hemangioblast colonies. Some cells may be able to form secondary EBs. Following approximately 3-6 days, and in some instances 3-4.5 days, hemangioblast colonies are observed. Hemangioblast colonies may be distinguished from other cells such as secondary EBs by their distinctive grape-like morphology and/or by their small size. In addition, hemangioblasts may be identified by the expression of certain markers (e.g., the expression of both early hematopoietic and endothelial cell markers) as well as their ability to differentiate into at least both hematopoietic and endothelial cells (see below, Deriving hemangioblast lineage cells). For example, while hemangioblasts lack certain features characteristic of mature endothelial or hematopoietic cells, these cells may be identified by the presence of certain markers (such as, for example, CD71+) and the absence of other markers (for example, CD34−). Hemangioblasts may also express GATA-1 and GATA-2 proteins, CXCR-4, and TPO and EPO receptors. In addition, hemangioblasts may be characterized by the absence or low expression of other markers (e.g., CD31, CD34, KDR, or other adhesion molecules). Further, hemangioblasts may be characterized by the expression of certain genes, e.g., genes associated with hemangioblasts and early primitive erythroblast development, such as, for example, SCL, LMO2, FLT-1, embryonic fetal globin genes, NF-E2, GATA-1, EKLF, ICAM-4, glycophoriuns, and EPO receptor).

Accordingly, hemangioblasts may be isolated by size (being smaller than the other cells) or purified with an anti-CD71+ antibody, such as by immunoaffinity column chromatography.

The hemangioblast cells may be isolated by size and/or morphology by the following procedure. After 6 to 7 days of growth, the cell mixture contains EBs, which are round and represent a clump of multiple cells, and hemangioblasts, which are grape-like, smaller than the EBs, and are single cells. Accordingly, hemangioblasts may be isolated based on their morphology and size. The hemangioblast cells may be manually picked, for example, when observing the cell mixture under a microscope. The cells may subsequently grow into colonies, each colony having between 100-150 cells.

Human hemangioblast colonies derived as described above may be picked and replated onto methylcellulose CFU-medium to form hematopoietic CFUs. In certain embodiments, CFU-medium comprises StemCell Technologies H4436. In further embodiments, hemangioblasts are plated in Stemline II media supplemented with cytokines and other factors. For example, individual BL-CFC colonies may be handpicked and transferred to a fibronectin-coated plate containing Stemline II with recombinant human SCF (e.g, ng/ml), TPO (e.g., 20 ng/ml), FL (e.g., 20 ng/ml), IL-3 (e.g., 20 ng/ml) VEGF (e.g., 20 ng/ml), G-CSF (e.g., 20n ng/ml), BMP-4 (e.g., 15 ng/ml), IL-6 (e.g., 10 ng/ml), IGF-1 (e.g, 10 ng/ml), endothelial cell growth supplement (ECGS, e.g., 100 µg/ml), Epo (e.g., 3 U/ml). Following one week of growth in vitro, non-adherent hematopoietic cells may be removed by gentle pipetting and used directly for hematopoietic CFU assay. Following removal of the non-adherent cells, the adherent populations may be grown for one more week in EGM-2 endothelial cell medium (Cambrex™), and then examined for the expression of vWF.

Expansion of Hemangioblasts In Vitro

Certain aspects of the invention relate to the in vitro expansion of hemangioblasts. In certain embodiments, hemangioblasts expanded by the methods of the invention are obtained from early embryoid bodies derived from human embryonic stem cells as described above.

In addition to deriving hemangioblasts from human embryonic stem cells (hES cells), hemangioblasts to be expanded may also be isolated from other mammalian sources, such as mammalian embryos (Ogawa et al. 2001 Int Rev Immunol (20):21-44, US patent publication no. 2004/0052771), cord blood from placenta and umbilical tissues (Pelosi, et al. 2002 Blood (100): 3203-3208; Cogle et al. 2004 Blood (103):133-5), peripheral blood and bone marrow (Pelosi et al. 2002 Hematopoiesis (100): 3203-3208). In certain embodiments, non-human hemangioblasts to be expanded may be generated from non-human (such as mouse and non-human primates) embryonic stem cells. In certain embodiments, hemangioblasts are obtained from umbilical cord blood (UCB) or bone marrow by methods such as, for example, magnetic bead positive selection or purification techniques (e.g. MACS column). Cells may be selected based on their CD71+ status and may be confirmed as CD34−. Further, the isolated hemangioblasts may be tested for their potential to give rise to both hematopoietic and endothelial cell lineages. In certain embodiments, hemangioblasts isolated or purified and optionally enriched from embryos, cord blood, peripheral blood, bone marrow, or other tissue, are more than 95% pure.

Bone marrow-derived cells may be obtained from any stage of development of the donor individual, including prenatal (e.g., embryonic or fetal), infant (e.g., from birth to approximately three years of age in humans), child (e.g., from about three years of age to about 13 years of age in humans), adolescent (e.g., from about 13 years of age to about 18 years of age in humans), young adult (e.g., from about 18 years of age to about 35 years of age in humans), adult (from about 35 years of age to about 55 years of age in humans) or elderly (e.g. from about 55 years and beyond of age in humans).

Human bone marrow may be harvested by scraping from the split sternum of a patient undergoing surgery, for example. Bone marrow may then be preserved in tissue clumps of 0.1 to 1 mm$^3$ in volume and then grown on a mouse embryonic feeder layer (e.g., a mitomycin C-treated or irradiated feeder layer). The bone marrow cells will attach to the plates and over a period of 1-2 weeks of culture, hemangioblast cells may be identified based on morphological features and/or cell markers and isolated (see US patent publication no. 2004/0052771). The cells may then be subsequently grown and expanded in serum-free conditions according to the methods disclosed herein.

In addition, bone marrow cells and cells from blood or other tissue may be fractionated to obtain hemangioblasts cells. Methods of fractionation are well known in the art, and generally involve both positive selection (i.e., retention of cells based on a particular property) and negative selection (i.e., elimination of cells based on a particular property). Methods for fractionation and enrichment of bone marrow-derived cells are best characterized for human and mouse cells.

There are a variety of methods known in the art for fractionating and enriching bone marrow-derived or other cells. Positive selection methods such as enriching for cells expressing CD71 may be used. And negative selection methods which remove or reduce cells expressing CD3, CD10, CD11b, CD14, CD16, CD15, CD16, CD19, CD20, CD32, CD45, CD45R/B220 or Ly6G may also be used alone or in combination with positive selection techniques. In the case of bone marrow cells, when the donor bone marrow-derived cells are not autologous, negative selection may be performed on the cell preparation to reduce or eliminate differentiated T cells.

Generally, methods used for selection/enrichment of bone marrow-derived, blood, or other cells will utilize immunoaffinity technology, although density centrifugation methods are also useful. Immunoaffinity technology may take a variety of forms, as is well known in the art, but generally utilizes an antibody or antibody derivative in combination with some type of segregation technology. The segregation technology generally results in physical segregation of cells bound by the antibody and cells not bound by the antibody, although in some instances the segregation technology which kills the cells bound by the antibody may be used for negative selection.

Any suitable immunoaffinity technology may be utilized for selection/enrichment of hemangioblasts from bone marrow-derived, blood, or other cells, including fluorescence-activated cell sorting (FACS), panning, immunomagnetic separation, immunoaffinity chromatography, antibody-mediated complement fixation, immunotoxin, density gradient segregation, and the like. After processing in the immunoaffinity process, the desired cells (the cells bound by the immunoaffinity reagent in the case of positive selection, and cells not bound by the immunoaffinity reagent in the case of negative selection) are collected and may be subjected to further rounds of immunoaffinity selection/enrichment.

Immunoaffinity selection/enrichment is typically carried out by incubating a preparation of cells comprising bone marrow-derived cells with an antibody or antibody-derived affinity reagent (e.g., an antibody specific for a given surface marker), then utilizing the bound affinity reagent to select either for or against the cells to which the antibody is bound. The selection process generally involves a physical separation, such as can be accomplished by directing droplets containing single cells into different containers depending on the presence or absence of bound affinity reagent (FACS), by utilizing an antibody bound (directly or indirectly) to a solid phase substrate (panning, immunoaffinity chromatography), or by utilizing a magnetic field to collect the cells which are bound to magnetic particles via the affinity reagent (immunomagnetic separation). Alternatively, undesirable cells may be eliminated from the bone marrow-derived cell preparation using an affinity reagent which directs a cytotoxic insult to the cells bound by the affinity reagent. The cytotoxic insult may be activated by the affinity reagent (e.g., complement fixation), or may be localized to the target cells by the affinity reagent (e.g., immunotoxin, such as ricin B chain).

Although the methods described above refer to enrichment of cells from a preparation of bone marrow-derived or blood cells, one skilled in the art will recognize that similar positive and negative selection techniques may be applied to cell preparations from other tissues.

Certain aspects of the invention relate to the in vitro expansion of hemangioblasts. In certain embodiments, hemangioblasts expanded by the methods of the invention are obtained from early embryoid bodies derived from human embryonic stem cells as described above. In other embodiments, the hemangioblasts are isolated or enriched from human tissue (e.g., placenta or cord blood, peripheral blood, bone marrow, etc.)

In certain embodiments, the hemangioblasts are expanded in the presence of a homeodomain protein (also referred to herein as a homeobox protein). In further embodiments, the hemangioblasts are expanded in the presence of HOXB4. In certain embodiments, HOXB4 is added to the hemangioblast cells throughout the method for expanding hemangioblast cells.

HOXB4 is a homeodomain transcription factor (also called HOX2F, HOX2, HOX-2.6, and in the rat HOXA5) that is expressed in vivo in the stem cell fraction of the bone marrow and that is subsequently down-regulated during differentiation. Expression of the HOXB4 gene is associated with the maintenance of primitive stem cell phenotypes (Sauvageau et al. 1995 *Genes Dev* 9: 1753-1765; Buske et al. 2002 *Blood* 100: 862-868; Thorsteinsdottir et al. 1999 *Blood* 94: 2605-2612; Antonchuk et al. 2001 *Exp Hematol* 29: 1125-1134).

HOXB4 used in the methods of the present invention to generate and expand hemangioblasts, includes, but is not limited to, full length HOXB4 (e.g., HOXB4 polypeptides specified by public accession numbers GI: 13273315, GI: 29351568, as well as any functional variants and active fragments thereof. The wildtype HOXB4 protein may be encoded by the amino acid sequence of SEQ ID NO: 1, SEQ ID NO: 3 or any other alternative allelic forms of such protein. Such sequences may be accessed via publicly available databases, such as Genbank. Further, HOXB4 may be ectopically expressed within the cell or may be provided in the media. HOXB4 expressed ectopically may be operably linked to an inducible promoter. HOXB4 provided in the media may be excreted by another cell type (e.g, a feeder layer) or added directly to the media.

The present invention also relates to fusion proteins comprising HOXB4 (including fusion proteins comprising full length HOXB4, or HOXB4 functional variants or active fragments of HOXB4). In addition to HOXB4, this fusion protein may also comprise any additional proteins, protein domains or peptides. In certain embodiments, HOXB4 may be joined to a protein transduction domain (PTD) to allow translocation of the protein from the medium into the cells and subsequently into nuclear compartments. Fusion proteins may or may not comprise one or more linker sequences located in between the protein domains.

Functional variants of HOXB4 include mutants of HOXB4 and alleleic variants, and active fragments thereof. Functional variants of HOXB4 include any HOXB4 polypeptides and active fragments thereof, that are capable of expanding hemangioblasts according to the methods of the present invention. HOXB4 functional variants also include HOXB4 polypeptides that exhibit greater transcriptional activity compared to the native HOXB4 protein. HOXB4 variants include proteins with one or more amino acid substitution, addition, and/or deletion in relation to a wild-type HOXB4. HOXB4 variants also include, but are not limited to, polypeptides that are at least 75% similar to the sequence provided in SEQ ID NO: 1 or SEQ ID NO:3. Accordingly, HOXB4 variants include polypeptides that are 80%, 85%, 90%, 95%, and 99% similar to the amino acid sequence provided in SEQ ID NO: 1 or SEQ ID NO:3.

HOXB4 variants also include polypeptides encoded by nucleic acid sequences that are at least 80% identical to a nucleic acid sequence encoding its complement (e.g., the wildtype HOXB4 protein may be encoded by nucleic acid sequences of SEQ ID NO: 2 (GI: 85376187) or SEQ ID NO: 4 (GI: 29351567)). Thus, HOXB4 variants include HOXB4 polypeptides that are encoded by nucleic acid sequences that are 85%, 90%, 95%, and 99% identical to the sequence provided in SEQ ID NO: 2 or SEQ ID NO: 4 or complement thereto.

Nucleic acid sequences encoding HOXB4 also include, but are not limited to, any nucleic acid sequence that hybridizes under stringent conditions to a nucleic acid sequence of SEQ ID NO: 2 or 4, complement thereto, or fragment thereof. Similarly, nucleic acids which differ from the nucleic acids as set forth in SEQ ID NO: 2 or 4 due to degeneracy in the genetic code are also within the scope of the invention. HOXB4 variant polypeptides also include splice variants or other naturally occurring HOXB4 proteins or nucleic acid sequences.

Active fragments of HOXB4 include, but are not limited to, any fragment of full length HOXB4 polypeptide that is capable of maintaining hemangioblasts according to the methods of the present invention. Accordingly, in one embodiment, a HOXB4 protein of the present invention is a HOXB4 protein that lacks part of the N-terminus, such as, for example, the N-terminal 31, 32, or 33 amino acids of full length HOXB4.

Any of the HOXB4 proteins may be fused with additional proteins or protein domains. For example, HOXB4 may be joined to a protein transduction domain (PTD).

Protein transduction domains, covalently or non-covalently linked to HOXB4, allow the translocation of HOXB4 across the cell membranes so the protein may ultimately reach the nuclear compartments of the cells.

PTDs that may be fused with a HOXB4 protein include the PTD of the HIV transactivating protein (TAT) (Tat 47-57) (Schwarze and Dowdy 2000 *Trends Pharmacol. Sci.* 21: 45-48; Krosl et al. 2003 *Nature Medicine* (9): 1428-1432). For the HIV TAT protein, the amino acid sequence conferring membrane translocation activity corresponds to residues 47-57 (YGRKKRRQRRR, SEQ ID NO: 5) (Ho et al., 2001, *Cancer Research* 61: 473-477; Vives et al., 1997, *J. Biol. Chem.* 272: 16010-16017). This sequence alone can confer protein translocation activity. The TAT PTD may also be the nine amino acids peptide sequence RKKRRQRRR (SEQ ID NO: 6) (Park et al. *Mol Cells* 2002 (30):202-8). The TAT PTD sequences may be any of the peptide sequences disclosed in Ho et al., 2001, *Cancer Research* 61: 473-477 (the disclosure of which is hereby incorporated by reference herein), including YARKARRQARR (SEQ ID NO: 7), YARAAARQARA (SEQ ID NO: 8), YARAARRAARR (SEQ ID NO: 9) and RARAARRAARA (SEQ ID NO: 10).

Other proteins that contain PTDs that may be fused to HOXB4 proteins of the present invention include the herpes simplex virus 1 (HSV-1) DNA-binding protein VP22 and the *Drosophila* Antennapedia (Antp) homeotic transcription factor (Schwarze et al. 2000 *Trends Cell Biol*. (10): 290-295). For Antp, amino acids 43-58 (RQIKIWFQNRRMKWKK, SEQ ID NO: 11) represent the protein transduction domain, and for HSV VP22 the PTD is represented by the residues DAATATRGRSAASRPTER-PRAPARSASRPRRPVE (SEQ ID NO: 12). Alternatively, HeptaARG (RRRRRRR, SEQ ID NO: 13) or artificial peptides that confer transduction activity may be used as a PTD of the present invention.

In additional embodiments, the PTD may be a PTD peptide that is duplicated or multimerized. In certain embodiments, the PTD is one or more of the TAT PTD peptide YARAAARQARA (SEQ ID NO: 14). In certain embodiments, the PTD is a multimer consisting of three of the TAT PTD peptide YARAAARQARA (SEQ ID NO: 15). A HOXB4 protein that is fused or linked to a multimeric PTD, such as, for example, a triplicated synthetic protein transduction domain (tPTD), may exhibit reduced lability and increased stability in cells. Such a HOXB4 construct may also be stable in serum-free medium and in the presence of hES cells.

Techniques for making fusion genes encoding fusion proteins are well known in the art. Essentially, the joining of various DNA fragments coding for different polypeptide sequences is performed in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

In certain embodiments, a fusion gene coding for a purification leader sequence, such as a poly-(His) sequence, may be linked to the N-terminus of the desired portion of the HOXB4 polypeptide or HOXB4-fusion protein, allowing the fusion protein be purified by affinity chromatography using a $Ni^{2+}$ metal resin. The purification leader sequence can then be subsequently removed by treatment with enterokinase to provide the purified HOXB4 polypeptide (e.g., see Hochuli et al., (1987) *J. Chromatography* 411:177; and Janknecht et al., *PNAS USA* 88:8972).

In certain embodiments, a HOXB4 protein or functional variant or active domain of it, is linked to the C-terminus or the N-terminus of a second protein or protein domain (e.g., a PTD) with or without an intervening linker sequence. The exact length and sequence of the linker and its orientation relative to the linked sequences may vary. The linker may comprise, for example, 2, 10, 20, 30, or more amino acids and may be selected based on desired properties such as solubility, length, steric separation, etc. In particular embodiments, the linker may comprise a functional sequence useful for the purification, detection, or modification, for example, of the fusion protein. In certain embodiments, the linker comprises a polypeptide of two or more glycines.

The protein domains and/or the linker by which the domains are fused may be modified to alter the effectiveness, stability and/or functional characteristics of HOXB4.

In certain embodiments, HOXB4 is ectopically expressed within the hemangioblast cell or is provided in the media.

HOXB4 expressed ectopically may be operably linked to a regulatory sequence. Regulatory sequences are art-recognized and are selected to direct expression of the HOXB4 polypeptide.

HOXB4 provided in the media may be excreted by another cell type. The other cell type may be a feeder layer, such as a mouse stromal cell layer transduced to express excretable HOXB4. For example, HOXB4 may be fused to or engineered to comprise a signal peptide, or a hydrophobic sequence that facilitates export and secretion of the protein. Alternatively, HOXB4, such as a fusion protein covalently or non-covalently linked to a PTD, may be added directly to the media. Additionally, HOXB4 may be borne on a viral vector, such as a retroviral vector or an adenoviral vector. Such a vector could transduce either the hemangioblasts or other cells in their culture.

Depending on the HOXB4 protein used, in particular embodiments HOXB4 is added to the media at selected times during the expansion of the hemangioblasts. Because the hemangioblasts are expanded in serum-free medium, HOXB4 is relatively stable. Accordingly, in certain embodiments, a HOXB4 protein or fusion protein is added every day to the human hemangioblasts. In other embodiments, a HOXB4 protein or fusion protein is added every other day, and in still other embodiments, a HOXB4 protein or fusion protein is added every 2 days. In one embodiment, a HOXB4 fusion protein, HOXB4-PTD, is added every 2 days to the media.

In certain embodiments, the hemangioblasts can be expanded in the presence of any other growth factors or proteins that are present in an amount sufficient to expand such cells.

Hemangioblasts obtained from any source, including human or non-human ES cells, bone marrow, placenta or umbilical cord blood, peripheral blood, or other tissue may be expanded according to the methods described above. Accordingly, in certain embodiments, a select number of purified hemangioblasts or enriched cells are mixed with serum-free methylcellulose medium optimized for hemangioblast growth (e.g., BL-CFU medium, see Example 1 and 2). This medium may be supplemented with early stage cytokines (including, but not limited to, EPO, TPO, FL, VGF, BMPs like BMP2, BMP4 and BMP7, but not BMP3) and HOXB4. In certain embodiments, erythropoietin (EPO) is added to the media. In certain embodiments, EPO, TPO and FL are added to the media. The cells are then plated onto ultra-low attachment culture dishes and grown in a $CO_2$ incubator. As mentioned above, hemangioblast colonies exhibit a distinctive grape-like morphology and are comparatively smaller than other cells and may consequently be distinguished from other cell types. The hemangioblasts may also be tested for markers as well as for their ability to differentiate further into either hematopoietic or endothelial cell lineages. The hemangioblasts are subsequently isolated and expanded in vitro. Media that may be used for expansion includes serum-free methylcellulose medium optimized for hemangioblasts growth (e.g., BL-CFU) supplemented with early stage cytokines and HOXB4. Early stage cytokines include, but are not limited to, EPO, TPO, FL, VEGF, BMPs like BMP2, BMP4 and BMP7, but not BMP3. In certain embodiments, erythropoietin (EPO) is added to the medium. In further embodiments, EPO, TPO and FL are added to the medium.

Accordingly, a medium for expanding hemangioblasts may comprise VEGF, SCF, EPO, BMP-4, and HoxB4; in certain embodiments the medium may further comprise TPO and FL. For example, single cells prepared from EBs cultured for approximately 3.5 days, were collected and dissociated by 0.05% trypsin-0.53 mM EDTA (Invitrogen) for 2-5 min, and a single cell suspension was prepared by passing through 22G needle 3-5 times. Cells were collected by centrifugation at 1,000 rpm for 5 min. Cell pellets were resuspended in 50-200 μl of Stemline I media. To expand hemangioblasts, single cell suspension derived from differentiation of 2 to 5×105 hES cells were mixed with 2 ml hemangioblast expansion media (HGM) containing 1.0% methylcellulose in Isocve's MDM, 1-2% Bovine serum albumin, 0.1 mM 2-mercaptoethanol, 10 μg/ml rh-Insulin, 200 μg/ml iron saturated human transferrin, 20 ng/ml rh-GM-CSF, 20 ng/ml rh-IL-3, 20 ng/ml rh-IL-6, 20 ng/ml rh-G-CSF, 3 to 6 units/ml rh-Epo, 50 ng/ml rh-SCF, 50 ng/ml rh-VEGF and 50 ng/ml rh-BMP-4, and 1.5 μg/ml of tPTD-HoxB4, with/without 50 ng/ml of Tpo and FL. The cell mixtures were plated on ultra-low dishes and incubated at 37° C. in 5% CO2 for 4-6 days.

In certain situations it may be desirable to obtain hemangioblasts from a patient or patient relative and expand said hemangioblasts in vitro. Such situations include, for example, a patient scheduled to begin chemotherapy or radiation therapy, or other situations wherein an autologous HSC transplantation (using the patient's own stem cells) may be used. Thus, the present invention provides methods of treating patients in need of cell-based therapy (for example, patients in need of hematopoietic reconstitution or treatment, or blood vessel growth or treatment of vascular injuries including ischemia, see below) using the expanded hemangioblasts or hemangioblast lineage cells of the invention, wherein the hemangioblasts are obtained from the bone marrow, blood, or other tissue of the patient or a patient relative. Accordingly, in certain embodiments, methods of treating a patient in need of hemangioblasts (or hemangioblast lineage cells) may comprise a step of isolating hemangioblasts from the patient or a patient relative. Hemangioblasts isolated from the patient or patient relative may be expanded in vitro according to the methods of the present invention and subsequently administered to the patient. Alternatively the expanded hemangioblasts may be grown further to give rise to hematopoietic cells or endothelial cells before patient treatment.

It is also possible to obtain human ES cells from such a patient by any method known in the art, such as somatic cell nuclear transfer. Hemangioblasts of that patient may then be generated and expanded from his own ES cells using a method of this invention. Those hemangioblasts or lineage derivatives thereof may be administered to that patient or to his relatives.

Using the methods of the present invention, human hemangioblasts are expanded to reach commercially large quantities which can be subsequently used in various therapeutic and clinical applications. Furthermore, the hemangioblasts obtained by the methods disclosed herein may be differentiated further to give rise to either hematopoietic or endothelial cell lineages for use in clinical applications.

The hemangioblasts obtained from the method of this invention for generating and expanding human hemangioblasts from human ES cells have the potential to differentiate into at least endothelial cells or hematopoietic cells (i.e., they are at least bi-potential). Other hemangioblasts may be bi-potential as well. Yet other hemangioblasts may be able to differentiate into cells other than hematopoietic and endothelial cells, i.e., they are multi- or pluri-potential).

Engineering MHC Genes in Human Embryonic Stem Cells to Obtain Reduced-Complexity Hemangioblasts The human embryonic stem cells used as the starting point for the method of generating and expanding human hemangioblast cells of this invention may also be derived from a library of human embryonic stem cells, each of which is hemizygous or homozygous for at least one MHC allele present in a human population. In certain embodiments, each member of said library of stem cells is hemizygous or homozygous for a different set of MHC alleles relative to the remaining members of the library. In certain embodiments, the library of stem cells is hemizygous or homozygous for all MHC alleles that are present in a human population. In the context of this invention, stem cells that are homozygous for one or more histocompatibility antigen genes include cells that are nullizygous for one or more (and in some embodiments, all) such genes. Nullizygous for a genetic locus means that the gene is null at that locus, i.e., both alleles of that gene are deleted or inactivated. Stem cells that are nullizygous for all MHC genes may be produced by standard methods known in the art, such as, for example, gene targeting and/or loss of heterozygocity (LOH). See, for example, United States patent publications US 20040091936, US 20030217374 and US 20030232430, and U.S. provisional application No. 60/729,173, the disclosures of all of which are hereby incorporated by reference herein.

Accordingly, the present invention relates to methods of obtaining hemangioblasts, including a library of hemangioblasts, with reduced MHC complexity. Hemangioblasts and hemangioblast lineage cells with reduced MHC complexity will increase the supply of available cells for therapeutic applications as it will eliminate the difficulties associated with patient matching. Such cells may be derived from stem cells that are engineered to be hemizygous or homozygous for genes of the MHC complex.

A human ES cell may comprise modifications to one of the alleles of sister chromosomes in the cell's MHC complex. A variety of methods for generating gene modifications, such as gene targeting, may be used to modify the genes in the MHC complex. Further, the modified alleles of the MHC complex in the cells may be subsequently engineered to be homozygous so that identical alleles are present on sister chromosomes. Methods such as loss of heterozygosity (LOH) may be utilized to engineer cells to have homozygous alleles in the MHC complex. For example, one or more genes in a set of MHC genes from a parental allele can be targeted to generate hemizygous cells. The other set of MHC genes can be removed by gene targeting or LOH to make a null line. This null line can be used further as the embryonic cell line in which to drop arrays of the HLA genes, or individual genes, to make a hemizygous or homozygous bank with an otherwise uniform genetic background.

In one aspect, a library of ES cell lines, wherein each member of the library is homozygous for at least one HLA gene, is used to derive hemangioblasts according to the methods of the present invention. In another aspect, the invention provides a library of hemangioblasts (and/or hemangioblast lineage cells), wherein several lines of ES cells are selected and differentiated into hemangioblasts. These hemangioblasts and/or hemangioblast lineage cells may be used for a patient in need of a cell-based therapy.

Accordingly, certain embodiments of this invention pertain to a method of administering human hemangioblasts, hematopoietic stem cells, or human endothelial cells that have been derived from reduced-complexity embryonic stem cells to a patient in need thereof. In certain embodiments, this method comprises the steps of: (a) identifying a patient that needs treatment involving administering human hemangioblasts, hematopoietic stem cells, or human endothelial cells to him or her; (b) identifying MHC proteins expressed on the surface of the patient's cells; (c) providing a library of human hemangioblasts of reduced MHC complexity made by the method for generating and expanding human hemangioblast cells in vitro of the present invention; (d) selecting the human hemangioblast cells from the library that match this patient's MHC proteins on his or her cells; (e) optionally differentiating the human hemangioblast cells identified in step (d) into human hematopoietic stem cells, endothelial cells or both, or cells that are further differentiated in either or both of these two lineages, depending on need; (f) administering any of the cells from step (d) and/or (e) to said patient. This method may be performed in a regional center, such as, for example, a hospital, a clinic, a physician's office, and other health care facilities. Further, the hemangioblasts selected as a match for the patient, if stored in small cell numbers, may be expanded prior to patient treatment.

Human Hemangio-Colony Forming Cells/Hemangioblasts

In certain aspects, the present invention provides human hemangio-colony forming cells. These cells are a unique, primitive cell type with a variety of therapeutic and other uses. Furthermore, this cell type provides an important tool for studying development of at least the hematopoietic and/or endothelial lineages. As such, the invention contemplates various preparations (including pharmaceutical preparations) and compositions comprising human hemangio-colony forming cells, as well as preparations (including pharmaceutical preparations) and compositions comprising one or more cell types partially or terminally differentiated from hemangio-colony forming cells.

The terms "hemangioblast" and "hemangio-colony forming cells" will be used interchangeably throughout this application. These cells can be described based on numerous structural and functional properties including, but not limited to, expression (RNA or protein) or lack of expression (RNA or protein) of one or more markers. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

Furthermore, hemangio-colony forming cells can be identified and characterized based on their structural properties. Specifically, and in certain embodiments, these cells are unique in that they are only loosely adherent to each other (loosely adherent to other hemangio-colony forming cells). Because these cells are only loosely adherent to each other, cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination of mechanical and enzymatic dissociation, is sufficient to disaggregate the cultures or colonies without substantially impairing the viability of the cells. In other words, mechanical dissociation does not require so much force as to cause substantial cell injury or death when compared to that observed subsequent to enzymatic dissociation of cell aggregates.

Furthermore, hemangio-colony forming cells can be identified or characterized based on the expression or lack of expression (as assessed at the level of the gene or the level of the protein) of one or more markers. For example, in certain embodiments, hemangio-colony forming cells can be identified or characterized based on lack of expression of one or more (e.g., the cells can be characterized based on lack of expression of at least one, at least two, at least three or at least four of the following markers) of the following cell surface markers: CD34, KDR, CD133, or CD31. Additionally or alternatively, hemangio-colony forming cells can be identified or characterized based on expression of GATA2 and/or LMO2. Additionally or alternatively, hemangio-colony forming cells can be identified or characterized based on expression or lack of expression (as assessed at the level of the gene or the level of the protein) of one or more markers analyzed in Table 2.

Hemangio-colony forming cells of the present invention can be identified or characterized based on one or any combination of these structural or functional characteristics. Note that although these cells can be derived from any of a number of sources, for example, embryonic tissue, prenatal tissue, or perinatal tissue, the term "hemangio-colony forming cells" applies to cells, regardless of source, that are capable of differentiating to give rise to at least hematopoietic cell types and/or endothelial cell types and that have one or more of the foregoing structural or functional properties.

To illustrate, human hemangio-colony forming cells of the present invention have at least one of the following structural characteristics: (a) can differentiate to give rise to at least hematopoietic cell types or endothelial cell types; (b) can differentiate to give rise to at least hematopoietic cell types and endothelial cell types; (c) are loosely adherent to each other (to other human hemangio-colony forming cells; (d) do not express CD34 protein; (e) do not express CD31 protein; (f) do not express KDR protein; (g) do not express CD133 protein; (h) express GATA2 protein; (i) express LMO2 protein. In certain embodiments, human hemangio-colony forming cells have at least two, at least three, at least four, at least five, at least six, at least seven, at least eight, or at least nine of the structural or functional characteristics detailed herein.

The invention provides for human hemangio-colony forming cells. Such cells can differentiate to produce at least hematopoietic and/or endothelial cell types. In certain embodiments, the cells are characterized as being loosely adherent to other human hemangio-colony forming cells. Alternatively or additionally, these cells may also be described based on expression or lack of expression of certain markers. For example, these cells may also be described based on lack of expression of at least one of the following proteins: CD34, KDR, CD133, and CD31.

As detailed above, one of the interesting properties of human hemangio-colony forming cells is that they are loosely adherent to each other. Because these cells are only loosely adherent to each other, cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

This property is not only useful in describing the cells and distinguishing them phenotypically from other cell types, but it also has significant therapeutic implications. For example, relatively large numbers (greater than $1 \times 10^6$ or even greater than $1 \times 10^7$ or even greater than $1 \times 10^8$) of the hemangio-colony forming cells can be injected into humans or other animals with substantially less risk of causing clots or emboli, or otherwise lodging in the lung. This is a significant advance in cellular therapy. The ability to safely administer relatively large numbers of cells makes cellular therapy practical and possible for the effective treatment of an increasing number of diseases and conditions.

The term "loosely adherent" is described qualitatively above and refers to behavior of the human hemangio-colony forming cells with respect to each other. Cultures or colonies of hemangio-colony forming cells can be dissociated to single cells using only mechanical dissociation techniques and without the need for enzymatic dissociation techniques. The cells are sufficiently loosely adherent to each other that mechanical dissociation alone, rather than enzymatic dissociation or a combination thereof, is sufficient to disaggregate the cultures or colonies without substantially impairing the viability of the cells. In other words, mechanical dissociation does not require so much force as to cause substantial cell injury or death.

The term can also be described more quantitatively. For example and in certain embodiments, the term "loosely adherent" is used to refer to cultures or colonies of hemangio-colony forming cells wherein at least 50% of the cells in the culture can be dissociated to single cells using only mechanical dissociation techniques and without the need for enzymatic dissociation techniques. In other embodiments, the term refers to cultures in which at least 60%, 65%, 70%, or 75% of the cells in the culture can be dissociated to single cells using only mechanical dissociation techniques and without the need for enzymatic dissociation techniques. In still other embodiments, the term refers to cultures in which at least 80%, 85%, 90%, 95%, 96%, 97%, 98%, 99%, or even 100% of the cells in the culture can be dissociated to single cells using only mechanical dissociation techniques and without the need for enzymatic dissociation techniques.

The ability to dissociate the hemangio-colony forming cells using only mechanical dissociation techniques and without the need for enzymatic dissociation techniques can be further quantitated based on the health and viability of the cells following mechanical dissociation. In other words, if dissociation without enzymatic techniques requires so much mechanical force that a significant number of the cells are damaged or killed, the cells are not loosely adherent, as defined herein. For example and in certain embodiments, the term "loosely adherent" refers to cultures of cells that can be dissociated to single cells using only mechanical dissociation techniques and without the need for enzymatic dissociation techniques, without substantially impairing the health or viability or the cells in comparison to that observed when the same cells are dissociated using enzymatic dissociation techniques. For example, the health or viability of the cells is decreased by less than 15%, 10%, 9%, 8%, 7%, 6%, 5%, 4%, 3%, 2%, or even less than 1% in comparison to that observed when a culture of the same cells are dissociated using enzymatic dissociation techniques.

Exemplary enzymatic dissociation techniques include, but are not limited to, treatment with trypsin, collagenase, or other enzymes that disrupt cell-cell or cell-matrix interactions. Exemplary mechanical dissociation techniques include, but are not limited to, one or more passages through a pipette.

Human hemangio-colony forming cells according to the present invention are defined structurally and functionally. Such cells can be generated from any of a number of sources including from embryonic tissue, prenatal tissue, perinatal tissue, and even from adult tissue. By way of example, human hemangio-colony forming cells can be generated from human embryonic stem cells, other embryo-derived cells (blastocysts, blastomeres, ICMs, embryos, trophoblasts/trophectoderm cells, trophoblast stem cells, primordial germ cells, embryonic germ cells, etc.), amniotic fluid, amniotic stem cells, placenta, placental stem cells, and umbilical cord.

The invention provides human hemangio-colony forming cells, compositions comprising human hemangio-colony forming cells, and preparations (including pharmaceutical preparations) comprising human hemangio-colony forming cells. Certain features of these aspects of the invention are described in detail below. The invention contemplates combinations of any of the following aspects and embodiments of the invention.

In one aspect, the invention provides a human hemangio-colony forming cell. The cell can differentiate to produce at least hematopoietic and/or endothelial cell types. In certain embodiments, the cell is loosely adherent to other human hemangio-colony forming cells. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell expresses or does not express one or more (e.g., at least one, two, three, four, five, six, seven, eight, nine, ten, etc.) of the markers provided in Table 2. In certain other embodiments, the cell has an expression profile as depicted in Table 2.

In another aspect, the invention provides a human hemangio-colony forming cell. The cell, which cell can differentiate to produce at least hematopoietic and/or endothelial cell types, and the cell does not express any of the following proteins: CD34, CD31, KDR, and CD133. In certain embodiments, the cell is loosely adherent to other human hemangio-colony forming cells. In other embodiments, the cell does express GATA2 and/or LMO2 protein. In certain other embodiments, the cell expresses or does not express one or more (e.g., at least one, two, three, four, five, six, seven, eight, nine, ten, etc) of the markers provided in Table 2. In certain other embodiments, the cell has an expression profile as depicted in Table 2.

In another aspect, the invention provides a cell culture comprising a substantially purified population of human hemangio-colony forming cells. The cells can differentiate to produce at least hematopoietic and endothelial cell types, and the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell expresses or does not express one or more (one, two, three, four, five, six, seven, eight, nine, ten, etc) of the markers provided in Table 2. In certain other embodiments, the cell has an expression profile as depicted in Table 2.

In another aspect, the invention provides a cell culture comprising human hemangio-colony forming cells differentiated from embryonic tissue. In certain embodiments, the hemangio-colony forming cells are loosely adherent to each other. In certain embodiments, the cells can differentiate to produce at least hematopoietic and/or endothelial cell types, and the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell expresses or does not express one or more (one, two, three, four, five, six, seven, eight, nine, ten, etc) of the markers provided in Table 2. In certain other embodiments, the cell has an expression profile as depicted in Table 2.

In another aspect, the invention provides a cell culture comprising human hemangio-colony forming cells, which cells can differentiate to produce at least hematopoietic and/or endothelial cell types. In certain embodiments, the cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell expresses or does not express one or more (one, two, three, four, five, six, seven, eight, nine, ten, etc) of the markers provided in Table 2. In certain other embodiments, the cell has an expression profile as depicted in Table 2.

In another aspect, the invention provides a pharmaceutical preparation comprising human hemangio-colony forming cells, which cells can differentiate to produce at least hematopoietic and/or endothelial cell types. In certain embodiments, the hemangio-colony forming cells are loosely adherent to each other. In certain embodiments, the cell does not express CD34 protein. In certain other embodiments, the cell does not express one or more of (e.g., the cell does not express at least one, at least two, at least three, or at least four of the following proteins) the following proteins: CD34, CD31, CD133, KDR. In certain other embodiments, the cell does express GATA2 and/or LMO2 protein. In certain other embodiments, the cell expresses or does not express one or more (one, two, three, four, five, six, seven, eight, nine, ten, etc) of the markers provided in Table 2. In certain other embodiments, the cell has an expression profile as depicted in Table 2. The pharmaceutical preparation can be preparing using any pharmaceutically acceptable carrier or excipient.

In another aspect, the invention provides a pharmaceutical preparation comprising human hemangio-colony forming cells, wherein the hemangio-colony forming cells do not express any of the following proteins: CD34, CD31, KDR, and CD133. In certain embodiments, the hemangio-colony forming cells can differentiate to produce at least hematopoietic and/or endothelial cell types. In certain embodiments, the hemangio-colony forming cells are loosely adherent to each other. In certain other embodiments, the cell does express GATA2 and/or LMO2 protein. In certain other embodiments, the cell expresses or does not express one or more (one, two, three, four, five, six, seven, eight, nine, ten, etc) of the markers provided in Table 2. In certain other embodiments, the cell has an expression profile as depicted in Table 2. The pharmaceutical preparation can be preparing using any pharmaceutically acceptable carrier or excipient.

In certain embodiments of any of the foregoing, the composition or pharmaceutical preparation comprises at least $1\times10^5$ human hemangio-colony forming cells. In certain other embodiment, of any of the foregoing, the composition or pharmaceutical preparation comprises at least $1\times10^6$, at least $5\times10^6$, at least $1\times10^7$, or greater than $1\times10^7$ human hemangio-colony forming cells.

Additional cells, compositions, and preparations include cells partially or terminally differentiated from human hemangio-colony forming cells. For example, the invention contemplates compositions and preparations comprising one or more hematopoietic and/or endothelial cell type differentiated from a hemangio-colony forming cell. Exemplary hematopoietic cell types include hematopoietic stem cells, platelets, RBCs, lymphocytes, megakaryocytes, and the like. By way of further examples, the invention contemplates compositions and preparations comprising one or more other cell type, such as one or more partially or terminally differentiated mesodermal cell type, differentiated from hemangio-colony forming cells.

In certain embodiments of any of the foregoing, the invention provides a cryopreserved preparation of human hemangio-colony cells or cells partially or terminally differentiated therefrom.

In certain embodiments of any of the foregoing, the invention provides for the therapeutic use of human hemangio-colony forming cells, or compositions or preparations of human hemangio-colony forming cells. Such cells and preparations can be used in the treatment of any of the conditions or diseases detailed throughout the specification, as well as in the blood banking industry. Furthermore, cells differentiated from human hemangio-colony forming cells, or compositions or preparations of human hemangio-colony forming cells, can be used therapeutically in the treatment of any of the conditions or diseases detailed throughout the specification, as well as in the blood banking industry.

The human hemangio-colony forming cells of the invention are can be used therapeutically. Additionally or alternatively, human hemangio-colony forming cells can be used to study development of endothelial and hematopoietic lineages or in screening assays to identify factors that can be used, for example, to (i) maintain human hemangio-colony forming cells or (ii) to promote differentiation of human hemangio-colony forming cells to one or more partially or terminally differentiated cell types. Furthermore, human hemangio-colony forming cells can be used to generate one or more partially or terminally differentiated cell types for in vitro or in vivo use.

The human hemangio-colony forming cells of the invention can be used in any of the methods or application described in the present application including, but not limited to, in the treatment of any of the diseases or conditions described herein.

Cell Preparations Comprising Hemangioblasts Expanded In Vitro

In certain embodiments of the present invention, mammalian (including human) hemangioblasts are expanded to reach commercial quantities and are used in various therapeutic and clinical applications. In particular embodiments, hemangioblasts are expanded to reach cell numbers on the order of 10,000 to 4 million (or more). These cell numbers may be reached within 3-4 days of starting the initial preparations. Accordingly, the present invention relates to preparations comprising large numbers of hemangioblasts, said preparations comprising at least 10,000, 50,000, 100,000, 500,000, a million, 2 million, 3 million or 4 million cells.

This invention also provides for a solution, a composition, and a preparation comprising large numbers of hemangioblasts, said solution, said composition, and said preparation comprising at least 10,000, 50,000, 100,000, 500,000, a million, 2 million, 3 million or 4 million cells. The hemangioblasts could be human.

Other aspects of the present invention relate to differentiating the hemangioblasts obtained by the methods disclosed herein into either hematopoietic or endothelial cell lineages, or both, that are subsequently used in clinical applications. Thus, the present invention also relates to cell preparations comprising large numbers of hematopoietic or endothelial cells. The invention also relates to differentiating the hemangioblasts obtained by the methods disclosed herein into other cell lineages, other than hematopoietic and endothelial cells. Thus, the present invention also relates to cell preparations comprising large numbers of other hemangioblast-derived cells.

Compositions and preparations comprising large numbers (e.g, thousands or millions) of hemangioblasts may be obtained by expanding hemangioblasts that are obtained as described above. Accordingly, the invention pertains to compositions and preparations comprising large numbers of hemangioblasts achieved by expanding ES cells (such as human ES cells) or hemangioblasts obtained from cord blood, peripheral blood or bone marrow. Further, as the methods of expansion may be applied to hemangioblasts of mouse, rat, bovine, or non-human primate origin, for example, the present invention also relates to compositions and preparations comprising large numbers of hemangioblasts of other species in addition to human. The hemangioblasts to be expanded by the methods of this invention may be bi-potential, i.e., can differentiate into either endothelial cells or hematopoietic stem cells. In certain embodiments, the human hemangioblasts generated and expanded from human ES cells are bi-potential. Hemangio-colony forming cells are capable of differentiating to give rise to at least hematopoietic cell types or endothelial cell types. Hemangio-colony forming cells are preferably bi-potential and capable of differentiating to give rise to at least hematopoietic cell types and endothelial cell types. As such, hemangio-colony forming cells of the present invention are at least uni-potential, and preferably bi-potential. Additionally however, hemangio-colony forming cells may have a greater degree of developmental potential and can, in certain embodiments, differentiate to give rise to cell types of other lineages. In certain embodiments, the hemangio-colony forming cells are capable of differentiating to give rise to other mesodermal derivatives such as cardiac cells (for example, cardiomyocytes) and/or smooth muscle cells.

Mammalian Hemangioblast Cell Markers

As described above, the hemangio-colony forming cells lack certain features characteristic of mature endothelial or hematopoietic cells. These hemangio-colony forming cells or hemangioblasts, however, may be identified by various markers such as, for example, CD71+, GATA-1 and GATA-2 proteins, CXCR-4, and TPO and EPO receptors. In additional embodiments, the hemangioblasts express LMO-2. Hemangioblasts may additionally be characterized by the absence or low expression of other markers. Accordingly, hemangioblasts may be CD34−, CD31−, and KDR−. In further embodiments, the hemangioblasts may be CD34−, CD31−, KDR−, and CD133−.

Accordingly, in certain embodiments, the hemangioblasts generated and expanded by the methods of present invention are characterized by the presence or absence of any one or more of the markers listed in Table 2. For example, the hemangioblasts may test negative for expression of any one or more of the markers listed in Table 2 that is denoted as "−" under "BL-CFC". Accordingly, in some embodiments, the hemangioblasts may be negative for CD34 expression. The cells may additionally or alternatively be negative for CD31, CD133, and/or KDR expression. In further embodiments, the hemangioblasts may express any of the markers denoted in Table 2 with "+". For example, the cells may express one or more of the markers LMO-2 and GATA-2. Expression of a marker may be assessed by any method, such as, for example, immunohistochemistry or immunoblotting to test for protein expression, or mRNA analysis to test for expression at the RNA level.

Deriving Hemangioblast Lineage Cells

The methods and cell preparations of the present invention also relate to hemangioblast derivative cells. Human hemangioblasts generated and expanded by this invention and mammalian hemangioblasts expanded by the methods of the invention may be differentiated in vitro to obtain hematopoietic cells (including hematopoietic stem cells (HSCs)) or endothelial cells, as well as cells that are further differentiated in these two lineages. These cells may subsequently be used in the therapeutic and commercial applications described below.

In certain embodiments, hematopoietic cells are derived by growing the hemangioblasts in serum-free BL-CFU for 3-10 days. In other embodiments, single-cell suspensions of hES-derived BL-CFC cells are grown for 10-14 days. Maintaining serum-free conditions is optimal insofar as serum-free conditions facilitate scale-up production and compliance with regulatory guidelines as well as reduce cost. Hemangioblasts of the present invention may also be grown in serum-free Hem-culture (Bhatia et al. 1997 *J Exp Med* (186): 619-624), which sustains human hematopoietic stem cells and comprises BSA (e.g, 1% BSA), insulin (e.g., 5 μg/ml human insulin), transferrin media or transferrin (e.g., 100 μg/ml human transferrin), L-glutamine, beta-mercaptoethanol (e.g., $10^{-4}$ M), and growth factors. The growth factors may comprise SCF (e.g., 300 ng/ml), granulocytic-colony-stimulating factor (G-CSF) (e.g., 50 ng/ml), Flt-3 (e.g., 300 ng/ml), IL-3 (e.g., 10 ng/ml), and IL-6 (e.g., 10 ng/ml). Other factors useful for obtaining hematopoietic cells from hemangioblasts include thrombopoietin (TPO) and VEGF (see, for example, Wang et al. 2005 *Ann NY Acad Sci* (1044): 29-40) and BMP-4. The hemangioblasts may also be grown in serum-free methylcellulose medium supplemented with a multilineage hematopoietic growth factor cocktail. Thus, the hemangioblasts may be grown in methylcellulose in Iscove modified Dulbecco medium (IMDM) comprising BSA, saturated human transferrin, human LDL, supplemented with early acting growth factors (e.g, c-kit ligand, flt3 ligand), multilineage growth factors (e.g., IL-3, granulocyte macrophage-CSF (GM-CSF)), and unilineage growth factors (e.g., G-CSF, M-CSF, EPO, TPO)), VEGF, and bFGF. Alternatively, the hemangioblasts may be grown in medium comprising unilineage growth factors to support the growth of one type of hematopoietic cell (e.g, red blood cells, macrophages, or granulocytes).

In one embodiment, hemangioblast colonies are resuspended in Stemline I media. Cells are then mixed with 1 ml of serum-free hematopoietic CFU media (H4436, Stem Cell Technologies) plus 1.5 μg/ml of tPTD-HoxB4 and 0.5% EX-CYTE (Serologicals Proteins Inc.™). The cell mixtures are then plated on cell culture untreated plates and incubated at 37° C. for 10-14 days. Hematopoietic CFUs arising following 10-14 days after initial plating may be characterized morphologically, such as by staining with Wright-Giemsa dye.

Hematopoietic cells may also be derived from the hemangioblast using other conditions known in the art (e.g., in media comprising IMDM, 30% fetal calf serum (FCS), 1% bovine serum albumin (BSA), $10^{-4}$ M beta-mercaptoethanol, and 2 mM L-glutamine). Further, in other embodiments basic fibroblast growth factor may be used to promote both BL-CFC frequency within EBs and promote hematopoietic differentiation (Faloon et al. 2000 *Development* (127): 1931-1941). In yet other embodiments, the growth factor hemangiopoietin (HAPO) is used to promote growth and hematopoietic differentiation of the hemangioblasts (Liu et al. 2004 *Blood* (103): 4449-4456). The differentiation into hematopoietic cells may be assessed by CD45 status (CD45+) and the CFU assay, for example.

To form hematopoietic cells, human hemangioblasts may be grown for 3-10 days, or optionally for longer periods of time (e.g., 10-14 days) in CFU-medium. Human hemangioblasts of the present invention are able to form CFUs comprising granulocytes, erythrocytes, macrophages, and megakaryocytes (CFU-GEMM/mix) as well as colony forming units containing only one of the latter cell types (e.g., CFU-G, CFU-E, CFU-M, and CFU-GM). In certain embodiments, single-cell suspensions of hES-derived BL-CFC cells are grown for 10-14 days to derive hematopoietic cells such as, for example, erythroid, myeloid, macrophage, and multilineage hematopoietic cells.

Other aspects of the invention relate to endothelial cells derived from the human hemangioblasts obtained and expanded or mammalian hemangioblasts expanded by the methods described herein. The hemangioblasts may be grown in conditions favorable to endothelial maturation.

In certain embodiments of the present invention, to obtain endothelial cells, hemangioblasts are first plated onto a fibronectin-coated surface and following 3-5 days (or in other embodiments 3-7 days), are replated onto a thick layer of Matrigel to support differentiation into endothelial cells. These conditions maintain the serum-free conditions established during hemangioblast development. Alternatively, hemangioblasts may be grown in media known to support differentiation into endothelial cells. Such conditions include, for example, Endo-culture comprising 20% fetal bovine serum (FBS), 50 ng/ml endothelial cell growth supplement (i.e., pituitary extracts), 10 IU/ml heparin, and 5 ng/ml human VEGF-$A_{165}$ (Terramani et al. 2000 *In Vitro Cell Dev Biol Anim* (36): 125-132). Other conditions known in the art include medium supplemented with 25% FCS/horse serum, and in some embodiments heparin (e.g., 10 U/ml), insulin like growth factor (IGF1) (e.g, 2 ng), and EC growth supplement (ECGS, e.g., 100 μg). The growth factors VEGF and EGF may also be used in combination with HAPO to support endothelial differentiation (Liu et al. 2004). The hemangioblasts may also be seeded onto dishes coated with collagen and fibronectin, for example, to promote differentiation into endothelial cells. Cells may be analyzed for von Willebrand factor (vWF) and endothelial nitric oxide synthase (eNOS) and the ability to form an endothelial network in vitro.

Accordingly, to form endothelial cells, hemangioblast colonies derived by the methods described above are picked and replated onto fibronectin-coated culture plates optimized for the first step towards endothelial differentiation. The cells may be plated in EGM-2 or EGM-2MV complete media (Cambrex™). Following 3 to 5 days, and in alternative embodiments 3 to 7 days, the cells are re-plated on a surface that supports endothelial differentiation, such as on a layer of Matrigel. Following 16-24 hours of incubation, the formation of branched tube-cords (see FIG. 8, for example) suggests typical endothelial cell behavior. Endothelial-specific assays such as LDL-uptake may also be used to confirm that these cells are of endothelial nature.

In other aspects of the invention, human hemangioblasts generated and expanded by this invention and mammalian hemangioblasts expanded by the methods of the invention may be differentiated in vitro to obtain other cells, as well as cells that are further differentiated from these cell lineages. Such additional cell lineages may be derived from the hemangioblasts generated and expanded by this invention and mammalian hemangioblasts expanded by the methods of the invention because the hemangioblast cells may have an even greater degree of developmental potential beyond differentiating into hematopoietic and endothelial cells.

Clinical and Commercial Embodiments of Human Hemangioblasts and Hemangioblast Lineage Cells Cell-Based Therapies While human hemangioblast cells have the potential to differentiate in vivo into either hematopoietic or endothelial cells, they can be used in cell-based treatments in which either of these two cell types are needed or would improve treatment. Further, a patient may be treated with any therapy or treatment comprising hemangioblast lineage cells (i.e., hematopoietic cells and/or endothelial cells). The following section describes methods of using the human hemangioblasts of this invention generated and expanded by the methods of this invention, or expanded by the methods of this invention.

In certain embodiments of the present invention, treatments to increase or treat hematopoietic cells and treatments for increasing blood vessel growth and/or facilitating blood vessel repair are contemplated. Accordingly, in certain aspects, the present invention relates to methods and compositions for treating a patient in need of hematopoietic cells or blood vessel growth or repair. The hemangioblasts may be injected into the blood vessel of a subject or be administered to the blood vessel of a subject through operation. The patient or the subject may be human.

In certain embodiments of the present invention, human hemangioblast cells are used in transplantation, where HSC transplantation would otherwise be used. Such transplantation may be used, for example, in hematopoietic reconstitution for the treatment of patients with acute or chronic leukemia, aplastic anemia and various immunodeficiency syndromes, as well as various non-hematological malignancies and auto-immune disorders, and to rescue patients from treatment-induced aplasia following high-dose chemotherapy and/or radiotherapy. Such transplantation may be achieved in vivo or ex vivo (such as in bone marrow transplant).

In other embodiments of the invention, human hemangioblast cells are used to treat patients in need of hematopoietic reconstitution or hematopoietic treatment. Such patients in include, for example, patients with thalassemias, sickle cell anemia, aplastic anemia (also called hypoplastic anemia), cytopenia, marrow hypoplasia, platelet deficiency, hematopoietic malignancies such as leukemias, paroxysmal nocturnal hemoglobinuria (PNH), and ADA (e.g., deaminase (ADA)-deficient severe combined immunodeficiency (SCID)).

Particular embodiments of the present invention therefore relate to methods of treating a patient in need of hematopoietic reconstitution or hematopoietic treatment using the hemangioblasts of the invention. Accordingly, the invention relates to methods of treating a patient in need of hematopoetic reconstitution or treatment comprising selecting a patient in need thereof, generating and expanding or expanding human hemangioblasts according to the methods of the present invention, and administering the human hemangioblasts into the patient. Alternatively, the method may comprise differentiating the generated and expanded or expanded human hemangioblasts into human hematopoietic cells and subsequently administering the hematopoietic cells to the patient.

Alternative embodiments include methods in which human hemangioblasts are produced on a large scale and stored prior to the selection of a patient in need thereof. Thus, other embodiments of the invention relate to methods of treating a patient in need of hematopoietic reconstitution or treatment comprising selecting a patient in need thereof, placing an order for human hemangioblasts already isolated and expanded according to the methods described above, and administering said human hemangioblasts to the patient. Likewise, the method may comprise differentiating said human hemangioblasts into human hematopoietic cells and administering said hematopoietic cells to the patient. In additional embodiments, hemangioblasts hemizygous or homozygous for at least one MHC allele are grown, optionally grown to commercial quantities, and optionally stored by a business entity. When a patient presents a need for such cells or hemangioblast lineage cells, a clinician or hospital will place an order with the business for such cells.

Because the human hemangioblast cells of the invention will proliferate and differentiate into endothelial cells under an angiogenic microenvironment, the human hemangioblast cells may be used in a therapeutic manner to provide new blood vessels or to induce repair of damaged blood vessels at a site of injury in a patient. Thus in certain aspects, the present invention relates to methods of promoting new blood vessel growth or repairing injured vasculature. The human hemangioblasts of the present invention may be used to treat endothelial injury, such as myocardium infarction, stroke and ischemic brain, ischemic limbs and skin wounds including ischemic limbs and wounds that occur in diabetic animals or patients, and ischemic reperfusion injury in the retina. Other ischemic conditions that may be treated with the hemangioblasts of the present invention include renal ischemia, pulmonary ischemia, and ischemic cardiomyopathy. Hemangioblasts may also be used to help repair injured blood vessels following balloon angioplasty or deployment of an endovascular stent. Hemangioblasts may additionally be used in tissue grafting, surgery and following radiation injury. Further, the hemangioblasts may be used to treat and/or prevent progression of atherosclerosis as well as to repair endothelial cell damage that occurs in systemic sclerosis and Raynaud's phenomenon (RP) (Blann et al. 1993 *J Rheumatol.* (20):1325-30).

Accordingly, the invention provides various methods involved in providing blood vessel growth or repair to a patient in need thereof. In one embodiment, the invention provides for a method for inducing formation of new blood vessels in an ischemic tissue in a patient in need thereof, comprising administering to said patient an effective amount of the purified preparation of human hemangioblast cells described above to induce new blood vessel formation in said ischemic tissue. Thus certain aspects of the present invention provide a method of enhancing blood vessel formation in a patient in need thereof, comprising selecting the patient in need thereof, isolating human hemangioblast cells as described above, and administering the hemangioblast cells to the patient. In yet another aspect, the present invention provides a method for treating an injured blood vessel in a patient in need thereof, comprising selecting the patient in need thereof, expanding or generating and expanding human hemangioblast cells as described above, and administering the hemangioblast cells to the patient. In addition to the aforementioned embodiments, the hemangioblasts may be produced on a large scale and stored prior to the selection of patient in need of hemangioblasts. In further embodiments, hemangioblasts hemizygous or homozygous for at least one MHC allele are grown, optionally grown to commercial quantities, and optionally stored before a patient is selected for hemangioblast treatment. Any of the aformentioned hemangioblasts or hemangioblast cell preparations may be administered directly into the circulation (intravenously). In certain embodiments (e.g., where vascular repair is necessary in the eye, such as in the treatment of ischemia/reperfusion injury to the retina), the hemangioblast cells or hemangioblast cell preparations may be administered by intra-vitreous injection.

Administration of the solutions or preparations of hemangioblasts or derivative cells thereof may be accomplished by any route and may be determined on a case by case basis. Also, an effective amount to be administered of these solutions or preparations of hemangioblasts or derivative cells thereof is an amount that is therapeutically effective and may be determined on a case by case basis.

In further aspects, hemangioblast lineage cells are used in therapeutic applications, including in the treatment of the indications described above, for example. Accordingly, hemangioblasts generated and expanded or expanded by the methods described herein are differentiated in vitro first to obtain hematopoetic and/or endothelial cells, and then to obtain cells that are further differentiated in these two lineages. These cells may be subsequently administered to a subject or patient to treat hematopoetic conditions or for hematopoietic reconstitution, or for the treatment of ischemia or vascular injury, for example.

HSCs derived from the human hemangioblasts obtained by the methods disclosed herein are grown further to expand the HSCs and/or to derive other hematopoietic lineage cell types. Certain aspects of the present invention relate to the use of HSCs derived from the hemangioblasts in transplantation. In additional embodiments, differentiated hematopoietic cells (such as, for example, granulocytes, erythrocytes, myeloid cells, megakaryocytes, platelets, macrophages, mast cells and neutrophils (Wiles and Keller 1991 Development (111): 259)) are used in various treatments such as transfusion therapy or for the treatment of infections. Accordingly, other embodiments of the present invention relate to methods of treating a patient in need of hematopoetic reconstitution or treatment using the HSCs or hematopoetic lineage cells derived from hemangioblasts of the invention.

In certain aspects, therefore, the present invention relates to methods of treating a patient in need of hematopoetic cells or treatment comprising selecting a patient in need thereof, expanding or isolating and expanding human hemangioblasts according to the methods of the present invention, differentiating said hemangioblast cells into hematopoetic stem cells and/or mature hematopoetic cells, and administering the hematopoietic cells to the patient.

In other aspects of the invention, the hemangioblasts are grown to give rise to endothelial cells according to the methods disclosed herein. The endothelial may subsequently be used to provide new blood vessels or to induce repair of damaged blood vessels at a site of injury in a patient. Thus in certain aspects, the present invention relates to methods of promoting new blood vessel growth or repairing injured vasculature in which endothelial cells derived from hemangioblasts are used as a therapy. The endothelial cells may be used to treat endothelial injury, such as myocardium infarction and pulmonary ischemia, stroke and ischemic brain, ischemic limbs and skin wounds including ischemic limbs and wounds that occur in diabetic animals or patients, ischemic reperfusion injury in the retina, renal ischemia. The endothelial cells may also be used to help repair injured blood vessels following balloon angioplasty or deployment of an endovascular stent as well as in grafting, surgery and following radiation injury. Further, the endothelial cells may be used to treat and/or prevent progression of atherosclerosis as well as to repair endothelial cell damage that occurs in systemic sclerosis and Raynaud's phenomenon.

The endothelial cell may be further differentiated and those cells, as appropriate, may be used in treating one or more of the "endothelial cell" disease or conditions, such as those listed in the preceding paragraph.

Accordingly, certain aspects of the invention relate to methods of treating a patient with endothelial or vascular injury or in need of blood vessel growth or repair comprising selecting a patient in need thereof, expanding or isolating and expanding human hemangioblasts according to the methods of the present invention, differentiating said hemangioblast cells into endothelial cells, and administering the endothelial cells to the patient.

Blood Banking

Another aspect of the present invention provides methods of producing hematopoietic cells suitable for transfusion. Although such cells and methods have numerous uses, a particularly important use would be in improving the availability of blood for transfusions. In certain preferred embodiments, the invention provides red blood cells differentiated from hemangioblasts/hemangio-colony forming units. Such differentiated red blood cells could be used for transfusions.

Further aspects of the invention relate to methods of generating differentiated hematopoietic cells from hemangioblasts/hemangio-colony forming units for use in blood transfusions for those in need thereof. In certain embodiments, differentiated hematopoietic cells are transfused to treat trauma, blood loss during surgery, blood diseases such as anemia, Sickle cell anemia, or hemolytic diseases, or malignant disease. In certain embodiments, red blood cells are transfused to treat trauma, blood loss during surgery, or blood diseases such as anemia, Sickle cell anemia, or hemolytic disease. In certain embodiments, platelets are transfused to treat congenital platelet disorders or malignant disease. In certain embodiments, a mixed population of red blood cells and platelets are transfused.

It should be noted that many differentiated hematopoietic cell types, particularly red blood cells, typically exist in vivo as a mixed population. Specifically, circulating red blood cells of varying levels of age and differentiation are found in vivo. Additionally, red blood cells mature over time so as to express less fetal hemoglobulin and more adult hemoglobin. The present invention contemplates transfusion of either purified populations of red blood cells or of a mixed population of red blood cells having varying levels of age and levels of differentiation. In particular embodiments, the invention contemplates transfusion of red blood cells expressing fetal hemoglobin (hemoglobin F).

This invention provides a method for producing differentiated hematopoietic cells from human hemangio-colony forming cells in vitro, said method comprising the steps of:
(a) providing human hemangio-colony forming cells; and
b) differentiating said hemangio-colony forming cells into differentiated hematopoietic cells.

This invention also provides a method for performing blood transfusions using hematopoietic cells that were differentiated in vitro from human hemangio-colony forming cells, said method comprising the steps of:
(a) providing human hemangio-colony forming cells;
(b) differentiating said hemangio-colony forming cells into differentiated hematopoietic cells; and
(c) performing blood transfusions with said differentiated hematopoietic cells.

This invention also provides a method for performing blood transfusions using hematopoietic cells that had been differentiated in vitro from human hemangio-colony forming cells, said method comprising the steps of:
(a) culturing a cell culture comprising human embryonic stem cells in serum-free media in the presence of at least one growth factor in an amount sufficient to induce the differentiation of said embryonic stem cells into embryoid bodies;
(b) adding at least one growth factor to said culture comprising embryoid bodies and continuing to culture said culture in serum-free media, wherein said growth factor is in an amount sufficient to expand human hemangio-colony forming cells in said embryoid bodies culture;
(c) differentiating said hemangio-colony forming cells into differentiated hematopoietic cells; and
(d) performing blood transfusions with said differentiated hematopoietic cells.

In certain embodiments, said stem cells, embryoid bodies and hemangio-colony forming are grown in serum-free media throughout steps (a) and (b) of said method.

This invention also provides a method for performing blood transfusions using hematopoietic cells that had been differentiated in vitro from human hemangio-colony forming cells, said method comprising the steps of:
(a) culturing a cell culture comprising human embryo-derived cells in serum-free media in the presence of at least one growth factor in an amount sufficient to induce the differentiation of said embryo-derived cells into embryoid bodies;
(b) adding at least one growth factor to said culture comprising embryoid bodies and continuing to culture said culture in serum-free media, wherein said growth factor is in an amount sufficient to expand human hemangio-colony forming cells in said embryoid bodies culture;
(c) disaggregating said embryoid bodies into single cells;
(d) adding at least one growth factor to said culture comprising said single cells and continuing to culture said culture in serum-free media, wherein said growth factor is in an amount sufficient to expand human hemangio-colony forming cells in said culture comprising said single cells;
(e) differentiating said hemangio-colony forming cells into differentiated hematopoietic cells; and
(f) performing blood transfusions with said differentiated hematopoietic cells.

In certain embodiments, said embryo-derived cells, embryoid bodies, hemangio-colony forming cells and single cells are grown in serum-free media throughout steps (a)-(d) of said method.

In certain embodiments, the embryo-derived cell is an embryonic stem cell.

In certain embodiments, the growth factor is a protein that comprises a homeobox protein, or a functional variant or an active fragment thereof. In certain embodiments, the homeobox protein comprises a HOXB4 protein, or a functional variant or an active fragment thereof.

In certain embodiments, the differentiated hematopoietic cells are produced as a single cell type such as red blood cells, platelets, and phagocytes. Note, however, that when a single cell type is produced, the cell type may be heterogeneous in terms of the level of maturity or differentiation of the particular cell type. By way of example, differentiated red blood cells may be heterogeneous in terms of level of maturity and cellular age. Without being bound by theory, such heterogeneity of erythrocytic cells may be beneficial because it mimics the way in which red blood cells are found in vivo.

In certain embodiments, the single cell types are mixed to equal the proportion of differentiated cell types that is found in blood. In certain embodiments, multiple differentiated hematopoietic cell types are produced in the same step. In certain embodiments, the phagocyte is selected from: granulocytes: neutrophils, basophils, eosinophils, lymphocytes or monocytes. In certain embodiments, the hematopoietic cell types are produced in a proportion approximately equal to the proportion of differentiated hematopoietic cell types found in blood, 96% red blood cells, 1% platelets, and 3% phagocytes. In certain embodiments, plasma is added to the differentiated hematopoietic cells before transfusion. In certain embodiments, packed cells, for example packed red blood cells, are transfused in the absence or substantial absence of plasma.

In certain embodiments, the differentiated hematopoietic cells produced from the methods of the application are functional. In certain embodiments, the platelets produced from the methods of the application are functional. In certain embodiments, the phagocytes produced from the methods of the application are functional. In certain embodiments, the red blood cells produced from the methods of the application are functional. In certain embodiments, the red blood cells express hemoglobin F prior to transfusion. In certain embodiments, the red blood cells carry oxygen. In certain embodiments, the red blood cells have a lifespan equal to naturally derived red blood cells. In certain embodiments, the red blood cells have a lifespan that is 75% of that of naturally derived red blood cells. In certain embodiments, the red blood cells have a lifespan that is 50% of that of naturally derived red blood cells. In certain embodiments, the red blood cells have a lifespan that is 25% of that of naturally derived red blood cells.

In certain embodiments, the methods of the application produce $1\times10^6$ cells per 100 mm dish. In certain embodiments, $2\times10^6$ cells are produced per 100 mm dish. In certain embodiments, $3\times10^6$ cells are produced per 100 mm dish. In certain embodiments, $4\times10^6$ cells are produced per 100 mm dish. In certain embodiments, $5\times10^6$ cells are produced per 100 mm dish. In certain embodiments, $6\times10^6$ cells are produced per 100 mm dish. In certain embodiments, $7\times10^6$ cells are produced per 100 mm dish. In certain embodiments, $8\times10^6$ cells are produced per 100 mm dish. In certain embodiments, $9\times10^6$ cells are produced per 100 mm dish. In certain embodiments, $1\times10^7$ cells are produced per 100 mm dish. In certain embodiments, $5\times10^7$ cells are produced per 100 mm dish. In certain embodiments, $1\times10^8$ cells are produced per 100 mm dish.

In certain embodiments, the differentiation step is performed using conditions known to one of skill in the art as discussed above. In certain embodiments, the differentiation step is performed using methods specific to differentiate cells into red blood cells (see WO2005/118780, herein incorporated by reference). In certain embodiments, the differentiation step is performed using methods specific to differentiate cells into platelets. In certain embodiments, the differentiation step is performed using methods specific to differentiate cells into leukocytes.

Differentiation agents which can be used according to the present invention include cytokines such as interferon-alpha A, interferon-alpha A/D, interferon-.beta., interferon-gamma, interferon-gamma-inducible protein-10, interleukin-1, interleukin-2, interleukin-3, interleukin-4, interleukin-5, interleukin-6, interleukin-7, interleukin-8, interleukin-9, interleukin-10, interleukin-1, interleukin-12, interleukin-13, interleukin-15, interleukin-17, keratinocyte growth factor, leptin, leukemia inhibitory factor, macrophage colony-stimulating factor, and macrophage inflammatory protein-1 alpha.

Differentiation agents according to the invention also include growth factors such as 6Ckine (recombinant), activin A, AlphaA-interferon, alpha-interferon, amphiregulin, angiogenin, B-endothelial cell growth factor, beta cellulin, B-interferon, brain derived neurotrophic factor, C10 (recombinant), cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoietin, estrogen receptor-alpha, estrogen receptor-B, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5S nerve growth factor (NGF), 7S-NGF, macrophage inflammatory protein-1B, macrophage inflammatory protein-2, macrophage inflammatory protein-3 alpha, macrophage inflammatory protein-3B, monocyte chemotactic protein-1, monocyte chemotactic protein-2, monocyte chemotactic protein-3, neurotrophin-3, neurotrophin-4, NGF-B (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoetin, transforming growth factor alpha, transforming growth factor-B1, transforming growth factor-B2, transforming growth factor-B3, transforming growth-factor-B5, tumor necrosis factor (alpha and B), and vascular endothelial growth factor.

Differentiation agents according to the invention also include hormones and hormone antagonists, such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin.

In addition, differentiation agents according to the invention include extracellular matrix components such as fibronectin, proteolytic fragments of fibronectin, laminin, thrombospondin, aggrecan, and syndezan.

Differentiation agents according to the invention also include antibodies to various factors, such as anti-low density lipoprotein receptor antibody, anti-progesterone receptor, internal antibody, anti-alpha interferon receptor chain 2 antibody, anti-c-c chemokine receptor 1 antibody, anti-CD 118 antibody, anti-CD 119 antibody, anti-colony stimulating factor-1 antibody, anti-CSF-1 receptor/c-fins antibody, anti-epidermal growth factor (AB-3) antibody, anti-epidermal growth factor receptor antibody, anti-epidermal growth factor receptor, phospho-specific antibody, anti-epidernal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor receptor antibody, anti-fibroblast growth factor, basic antibody, anti-gamma-interferon receptor chain antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progesterone receptor antibody, anti-retinoic acid receptor-alpha antibody, anti-thyroid hormone nuclear receptor antibody, anti-thyroid hormone nuclear receptor-alpha 1/Bi antibody, anti-transferrin receptor/CD71 antibody, anti-transforming growth factor-alpha antibody, anti-transforming growth factor-B3 antibody, anti-tumor necrosis factor-alpha antibody, and anti-vascular endothelial growth factor antibody.

This invention also provides a library of differentiated hematopoietic cells that can provide matched cells to potential patient recipients as described above. In certain embodiments, the cells are stored frozen. Accordingly, in one embodiment, the invention provides a method of conducting a pharmaceutical business, comprising the step of providing differentiated hematopoietic cell preparations that are homozygous for at least one histocompatibility antigen, wherein cells are chosen from a bank of such cells comprising a library of human hemangio-colony forming cells that can be expanded by the methods disclosed herein, wherein each hemangio-colony forming cell preparation is hemizygous or homozygous for at least one MHC allele present in the human population, and wherein said bank of hemangio-colony forming cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the hemangio-colony forming cells. In certain embodiments, hemangio-colony forming cells of all blood types are included in the bank. In certain embodiments, hemangio-colony forming cells are matched to a patient to ensure that differentiated hematopoietic cells of the patient's own blood type are produced. In certain embodiments, hemangio-colony forming cells are negative for antigenic factors A, B, Rh, or any combination thereof. In certain embodiments, the differentiated hematopoietic cells are universal donor cells. By way of example, hematopoietic cells that are type O and Rh negative can be universally used for blood transfusion. In certain embodiments, the invention provides methods for producing type O, Rh negative red blood cells for universal transfusion.

In certain embodiments, red blood cells differentiated from hemangio-colony forming cells express fetal hemoglobin. Transfusion of red blood cells that express fetal hemoglobin may be especially useful in the treatment of Sickle cell anemia. As such, the present invention provides improved methods for treating Sickle cell anemia.

In one embodiment, after a particular hemangio-colony forming cell preparation is chosen to be suitable for a patient, it is thereafter expanded to reach appropriate quantities for patient treatment and differentiated to obtain differentiated hematopoietic cells prior to administering cells to the recipient. Methods of conducting a pharmaceutical business may also comprise establishing a distribution system for distributing the preparation for sale or may include establishing a sales group for marketing the pharmaceutical preparation.

In any of the foregoing, hemangio-colony forming cells can be directly differentiated or hemangio-colony forming cells can be frozen for later use. In certain embodiments, the invention provides a frozen culture of hemangio-colony forming cells suitable for later thawing and expansion, and also suitable for differentiation to hematopoietic or endothelial lineages.

Human hemangio-colony forming cells can be used to generate substantial numbers of hematopoietic cell types that can be used in blood transfusions. For examples, substantial numbers of homogeneous or heterogeneous populations RBCs and/or platelets can be generated from human hemangio-colony forming cells. Hemangio-colony forming cells and hematopoietic cell types differentiated therefrom can be banked, as is currently done with donated blood products, and used in transfusions and other treatments. Banking of these products will help alleviate the critical shortage of donated blood products. Additionally, hemangio-colony forming cells and derivative products can be genetically manipulated in vitro to provide universal donor blood products.

As such, in certain aspects the invention provides a method of conducting a blood banking business. The subject banking business involves the derivation and storage (long or short term) of hemangio-colony forming cells and/or hematopoietic cell types (e.g., RBCs, platelets, lymphocytes, etc.) generated therefrom. Cells can be cryopreserved for long term storage, or maintained in culture for relatively short term storage. Cells can be typed and cross-matched in much the same way the currently available blood products are typed, and the cells can be stored based on type. Additionally and in certain embodiments, cells can be modified to specifically generate cells that are A negative and/or B negative and/or Rh negative to produce cells that are universally or nearly universally suitable for transfusion into any patient.

Note that hemangio-colony forming cells and/or differentiated hematopoietic cell types can be generated using any of the methods of the invention detailed through the specification.

In certain embodiments of a method of conducting a blood banking business, the cells (hemangio-colony forming cells and/or differentiated hematopoietic cell types) are generated and stored at one or more central facilities. Cells can then be transferred to, for example, hospitals or treatment facilities for use in patient care. In certain other embodiments, cells are maintained in a cryopreserved state and specifically thawed and prepared for transfusion based on orders from hospitals or other treatment facilities. Such orders may be a standing order (e.g., generate and provide a certain quantity of cells of a certain number of units In certain embodiments, the method includes a system for billing hospitals or insurance companies for the costs associated with the banked products.

In certain embodiments of any of the foregoing, the cells can be allocated based on cell number, volume, or any unit that permits the user to quantify the dose being administered to patients and/or to compare these doses to that administered during a standard blood transfusion.

In certain embodiments, the cells are generated, stored, and administered as a mixed population of cells. For example, the preparation may include cells of varying developmental stages, as well as distinct cell types. In other embodiments, the cells are generated, stored, and/or administered as a substantially purified preparation of a single cell type.

In certain embodiments, the preparations of cells are screened for one or more infectious diseases. Screening may occur prior to or subsequent to generation or storage. For example, the preparations of cells may be screened to identify hepatitis, HIV, or other blood-borne infectious disease that could be transmitted to recipients of these products.

Induction of Tolerance in Graft Recipients

The human hemangioblast cells generated and expanded by the methods of this invention, or expanded by the methods of this invention, may be used to induce immunological tolerance. Immunological tolerance refers to the inhibition of a graft recipient's immune response which would otherwise occur, e.g., in response to the introduction of a nonself MHC antigen (e.g., an antigen shared with the graft and the tolerizing hemangioblasts) into the recipient. Thus, tolerance refers to inhibition of the immune response induced by a specific donor antigen as opposed to the broad spectrum immune inhibition that may be elicited using immunosuppressants. Tolerance may involve humoral, cellular, or both humoral and cellular responses. Tolerance may include the elimination and/or inactivation of preexisting mature donor-reactive T cells as well as long-term (e.g. lifelong) elimination and/or inactivation of newly developing donor-reactive T cells.

The methods described in the present invention of generating and expanding human hemangioblasts offer several advantages for inducing tolerance. The methods of the present invention result in the generation of large, previously unobtainable numbers of human hemangioblasts. Large numbers of human hemangioblasts allow induction of tolerance in graft recipients with less toxic preconditioning protocols. Furthermore, the methods of the present invention provide for the generation of a library of human hemangioblasts, each of which is hemizygous or homozygous for at least one MHC allele present in the human population, wherein each member of said library of hemangioblast cells is hemizygous or homozygous for a different set of MHC alleles relative to the other members in the library. Such a library of human hemangioblasts can be used in the selection of tolerizing human hemangioblast cells such that cells can be selected to match any available donor graft.

Bone marrow transplantation and subsequent establishment of hematopoietic or mixed chimerism have previously been shown to induce specific tolerance to new tissue types derived from hematopoietic stem cells in both murine and human models. Hematopoietic or mixed chimerism refers to the production in a recipient of hematopoietic cells derived from both donor and recipient stem cells. Hence, if a recipient achieves hematopoietic chimerism, the recipient will be tolerant to donor-specific antigens. In many protocols for inducing tolerance, the tolerizing donor cells that are administered to the recipient engraft into the bone marrow of the recipient. To create hematopoietic space in the recipient bone marrow for the donor cells, some protocols require a step of creating hematopietic space (e.g., by whole body irradiation), and such a step is typically toxic or harmful to the recipient. However, if very large numbers of donor tolerizing cells are available, there is evidence from rodent models that irradiation can be completely eliminated, thereby achieving hematopoietic or mixed chimerism with the advantage of less toxic pre-conditioning regimens. Thus, mixed chimerism can be achieved, for example, with specific, non-myeloablative recipient conditioning.

Accordingly, as the novel methods described herein enable the production of large numbers of human hemangioblast cells, the present invention offers the advantage of inducing immune tolerance with less rigorous or less toxic conditioning protocols. For example, the hematopoietic space-creating step may be eliminated if a sufficient number of tolerizing donor cells are used.

Accordingly, in certain embodiments of the present invention, human hemangioblast cells generated and expanded or expanded by the methods described herein may be used to induce immunological tolerance. While not wishing to be bound by any theory on the mechanism, the human hemangioblast cells may induce immunological tolerance by homing to the recipient's bone marrow and engrafting into the recipient's bone marrow in order to produce mixed chimerism.

In certain embodiments, donor human hemangioblast cells are administered to a recipient patient (e.g., by intravenous injection) prior to implanting a graft or transplanting an organ, tissue, or cells from the donor into the recipient patient. In certain embodiments, human hemangioblasts are administered to induce tolerance in patients in need thereof (e.g., graft or transplant recipients). Accordingly, in certain embodiments the method of inducing tolerance in a human recipient patient comprises the steps of: (a) selecting a patient in need of a transplant or cellular therapy; (b) administering to said patient human hemangioblast cells derived from a donor or that are matched to the donor, wherein said hemangioblast cells are generated and expanded or expanded according to the methods of this invention, and (c) implanting a donor organ, tissue, or cell graft into the recipient patient, wherein said hemangioblast cells induce tolerance to donor antigens. In certain embodiments, the patient will receive an organ, tissue, or cell therapy, wherein the organ, tissue, or cells are obtained from the donor or a donor cell source. For example, hemangioblast cells from a donor can be (1) expanded according to the methods described herein to generate a large number of donor tolerizing cells, and (2) expanded and differentiated in vitro to obtain hematopoietic or endothelial cells or tissues, which can be subsequently implanted into the recipient patient. In other embodiments, the organ, tissue, or cell therapy is not derived from donor hemangioblast cells but is matched to the donor hemangioblasts.

As used herein, the term "matched" relates to how similar the HLA typing is between the donor and the recipient (e.g., graft). In one embodiment, the term "matched" with respect to donor hemangioblast cells and graft refers to a degree of match t the MHC class I and/or at the MHC class II alleles such that rejection does not occur. In another embodiment, the term "matched" with respect to donor hemangioblasts and graft refers to a degree of match at the MHC class I and/or at the MHC class II alleles such that the donor graft is tolerized by its matching donor hemangioblast cells. In another embodiment, the term "matched" with respect to donor hemangioblast and graft refers to a degree of match at the MHC class I and/or at the MHC class II alleles such that immunosuppression is not required.

The methods described herein for inducing tolerance to an allogeneic antigen or allogeneic graft may be used where, as between the donor and recipient, there is degree of mismatch at MHC loci or other loci, such that graft rejection results. Accordingly, for example, in certain embodiments, there may be a mismatch at least one MHC locus or at least one other locus that mediates recognition and rejection, e.g., a minor antigen locus. In some embodiments, for example, the HLA alleles of the recipient and donor are mismatched and result in one or more mismatched antigens. With respect to class I and class II MHC loci, the donor and recipient may be, for example: matched at class I and mismatched at class II; mismatched at class I and matched at class II; mismatched at class I and mismatched at class II; matched at class I, matched at class II. In any of these combinations other loci which control recognition and rejection, e.g., minor antigen loci, may be matched or mismatched. Mismatched at MHC class I means mismatched for one or more MHC class I loci, e.g., mismatched at one or more of HLA-A, HLA-B, or HLA-C. Mismatched at MHC class II means mismatched at one or more MHC class II loci, e.g., mismatched at one or more of a DPA, a DPB, a DQA, a DQB, a DRA, or a DRB. For example, the hemangioblasts and the graft may be matched at class II HLA-DRB1 and DQB1 alleles. The hemangioblasts and graft may further be matched at two or more class I HLA-A, B, or C, alleles (in addition to having matched DRB1 and DQB1 alleles).

In other embodiments, the tolerizing donor cells are cells derived from the hemangioblasts generated and expanded or expanded by the methods described herein. According to this embodiment, donor human hemangioblasts are differentiated in vitro to give rise to donor hematopoietic stem cells, and the donor hematopoietic stem cells are then administered to the recipient patient to induce tolerance. In any of the above methods, the donor hemangioblasts or hematopoietic stem cells derived therefrom and administered to said recipient prepare the recipient patient for the matched (with respect to the donor tolerizing cells) transplant or graft by inducing tolerance in said recipient.

In other embodiments, the method of inducing tolerance further comprises the step(s) of creating hematopoietic space (to promote engraftment of hemangioblasts or hematopoietic stem cells derived therefrom). In another embodiment, the method of inducing tolerance further comprises the step(s) of temporarily inhibiting rejection of donor hemangioblast cells or hematopoetic stem cells derived therefrom by, for example, eliminating and/or inactivating preexisting donor-reactive T cells. In order to create hematopoietic space, the method may include irradiation (e.g., whole body, lymphoid, or selective thymic irradiation). To prevent rejection of donor cells, the method may further comprise the administration of drugs or antibodies (e.g., inhibitors of cell proliferation, anti-metabolites, or anti-T cell or anti-CD8 or anti-CD4 antibodies), and/or other treatments that promote survival and engraftment of the donor cells and the formation of mixed chimerism (e.g., the administration of stromal cells or growth factors, cytokines, etc. to said recipient, or other agents that deplete or inactive the recipient's natural antibodies). In certain embodiments, the irradiation, antibodies, drugs, and/or other agents administered to create hematopoietic space and/or promote survival of donor cells in the recipient, is sufficient to inactivate thymocytes and/or T cells in the recipient. Such a step of creating hematopoietic space and/or temporarily inhibiting rejection of donor cells may be performed, for example, before the introduction of the donor hemangioblast cells to said recipient. Alternatively, the patient may receive an agent or method for blocking, eliminating, or inactivating T cells concurrently with the administration of the donor tolerizing cells.

In certain embodiments, a combination of hematopoietic space-creating and immunosuppressive methods are used. For example, a recipient may receive an anti-T cell antibody in combination with low dose whole body irradiation and/or thymic irradiation. In one embodiment, the recipient may receive anti-CD4 and anti-CD8 antibodies, followed by a mild, nonmyeloablative dose of whole body irradiation (e.g., a dose that eliminates a fraction of the recipient's bone marrow without rendering the bone marrow unrecoverable) and selective thymic irradiation or alternatively, an additional dose of T cell-inactivating antibodies or costimulatory blocking reagents (e.g., CTLA4-Ig and/or anti-CD40L antibody). Following the irradiation, donor hemangioblast cells, or hematopoietic stem cells derived therefrom, may be administered to the recipient (e.g., by intravenous injection). In this embodiment, whole body irradiation to promote engraftment of donor cells may be replaced by administering a large number of donor human hemangioblasts or hematopoietic stem cells derived therefrom. Obtaining such large numbers of donor human cells can be achieved according to the methods described herein.

In another embodiment, treatments to deplete or inactivate recipient T cells may help to prevent inhibition of engraftment or promote survival of the administered donor tolerizing human hemangioblast cells. In another embodiment, the method may include clonal deletion of donor-reactive cells in the recipient patient. For example, a patient may receive a mild dose of whole body irradiation, followed by administration of donor human hemangioblasts and T cell costimulatory blockade. Alternatively, a patient may receive T cell costimulatory blockade and administration of large numbers of donor human hemangioblast cells without receiving irradiation.

In another embodiment, tolerance may be achieved without myeloablative conditioning of the recipient. In one embodiment, a recipient may receive donor human hemangioblasts in combination with anti-CD40L to facilitate engraftment of donor hemangioblasts. For example, a recipient may receive large numbers of donor hemangioblasts, along with anti-CD40L monoclonal antibody, followed within a few days by a dose of CTLA4-Ig. Such a protocol may delete donor-reactive T cells and block the CD40-CD40L interaction. The novel methods described herein for generating and expanding human hemangioblasts in vitro render such a mild tolerance protocol feasible.

Following recipient conditioning and/or depletion or blocking of donor-reactive T cells, donor tolerizing human hemangioblasts generated by the methods of the present invention are administered to the recipient. Donor human hemangioblasts may be derived from hemangioblasts obtained from a tissue or cell source from the donor. Alternatively, donor human hemangioblasts may be obtained from a different non-donor source that is matched to the donor.

In certain embodiments, tolerance is induced in a recipient patient by administering donor human hemangioblasts in multiple administrations (e.g., by two, three, four, or more administrations of the donor cells). Accordingly, tolerance may be induced by a method comprising multiple administrations of donor tolerizing cells, wherein the multiple administrations are given to the recipient within a timeframe of a week or less.

In certain embodiments, the ability of the human hemangioblast cells of this invention to induce immunological tolerance may be evaluated using different experimental model systems. For example, the ability to establish a human immune system in a SCID mouse has been used to study the human immune response in an experimental model. It has been previously shown that human fetal liver and thymus tissue may be used to reconstitute a functional human immune system in an immuno-incompetent mouse recipient. Similarly, the functional capacity of the human hemangioblast cells of this invention can be assessed using a similar experimental model system. For example, the ability of human hemangioblasts to replace human fetal liver in establishing a functional human immune system in the mouse can be evaluated using the above-described experimental model. Further, in a mouse with a functional human immune system (e.g., where a human fetal liver and thymus tissue is used to establish a human immune system in a SCID mouse to produce a hu-SCID mouse), human "donor" hemangioblasts (mismatched with respect to the fetal liver and thymic tissue used to establish the hu-SCID mouse) may be administered to the hu-SCID mouse, according to any of the methods described above, in order to achieve mixed chimerism. Tolerance to donor antigen can be subsequently tested upon implantation of an allograft matched with respect to the donor hemangioblasts into these animals.

In certain embodiments, the present invention relates to cell combinations. Effective cell combinations comprise two components: a first cell type to induce immunological tolerance, and a second cell type that regenerates the needed function. Both cell types may be produced by the methods of the present invention and obtained from the same donor. For example, human hemangioblast cells from a donor may be used as the tolerizing donor cells. Cells from the donor (e.g., embryonic stem cells, pluripotent stem cells or early progenitor cells, or hemangioblasts) may also be used to generate, for example, hematopoietic cells or endothelial cells (as described herein), neural cells such as oligodendrocytes, hepatocytes, cardiomyocytes or cardiomyocyte precursors, or osteoblasts and their progenitors. Accordingly, the donor human hemangioblasts may be used to induce tolerance in a recipient such that the recipient is tolerant to cells or tissues derived from said donor hemangioblast cells or from said donor embryonic or pluripotent stem cells.

In another embodiment, the two cell components of the cell combinations of the present invention may be obtained from different sources or donors, wherein the two sources or donors are matched. For example, hemangioblasts may be generated from an embryonic stem cell source, whereas the graft cells or tissues may be obtained from a source that is different from the embryonic stem cell source used to generate the human hemangioblasts. In such embodiments, the two sources are matched.

For any of the therapeutic purposes described herein, human hemangioblast or hematopoietic cells derived therefrom for immunotolerance may be supplied in the form of a pharmaceutical composition, comprising an isotonic excipient prepared under sufficiently sterile conditions for human administration.

Hemangioblasts in Gene Therapy

Other aspects of the invention relate to the use of hemangioblast cells, or hematopoietic or endothelial cells differentiated therefrom, or in turn cells further differentiated from these cells, in gene therapy. The preparation of mammalian hemangioblast cells of the invention may be used to deliver a therapeutic gene to a patient that has a condition that is amenable to treatment by the gene product of the therapeutic gene. The hemangioblasts are particularly useful to deliver therapeutic genes that are involved in or influence angiogenesis (e.g VEGF to induce formation of collaterals in ischemic tissue), hematopoiesis (e.g. erythropoietin to induce red cell production), blood vessel function (e.g. growth factors to induce proliferation of vascular smooth muscles to repair aneurysm) or blood cell function (e.g. clotting factors to reduce bleeding) or code for secreted proteins e.g. growth hormone. Methods for gene therapy are known in the art. See for example, U.S. Pat. No. 5,399,346 by Anderson et al. A biocompatible capsule for delivering genetic material is described in PCT Publication WO 95/05452 by Baetge et al. Methods of gene transfer into bone-marrow derived cells have also previously been reported (see U.S. Pat. No. 6,410,015 by Gordon et al.). The therapeutic gene can be any gene having clinical usefulness, such as a gene encoding a gene product or protein that is involved in disease prevention or treatment, or a gene having a cell regulatory effect that is involved in disease prevention or treatment. The gene products may substitute a defective or missing gene product, protein, or cell regulatory effect in the patient, thereby enabling prevention or treatment of a disease or condition in the patient.

Accordingly, the invention further provides a method of delivering a therapeutic gene to a patient having a condition amenable to gene therapy comprising, selecting the patient in need thereof, modifying the preparation of hemangioblasts so that the cells carry a therapeutic gene, and administering the modified preparation to the patient. The preparation may be modified by techniques that are generally known in the art. The modification may involve inserting a DNA or RNA segment encoding a gene product into the mammalian hemangioblast cells, where the gene enhances the therapeutic effects of the hemangioblast cells. The genes are inserted in such a manner that the modified hemangioblast cell will produce the therapeutic gene product or have the desired therapeutic effect in the patient's body. In one embodiment, the hemangioblasts are prepared from a cell source originally acquired from the patient, such as bone marrow. The gene may be inserted into the hemangioblast cells using any gene transfer procedure, for example, naked DNA incorporation, direct injection of DNA, receptor-mediated DNA uptake, retroviral-mediated transfection, viral-mediated transfection, non-viral transfection, lipid-mediated transfection, electrotransfer, electroporation, calcium phosphate-mediated transfection, microinjection or proteoliposomes, all of which may involve the use of gene therapy vectors. Other vectors can be used besides retroviral vectors, including those derived from DNA viruses and other RNA viruses. As should be apparent when using an RNA virus, such virus includes RNA that encodes the desired agent so that the hemangioblast cells that are transfected with such RNA virus are therefore provided with DNA encoding a therapeutic gene product. Methods for accomplishing introduction of genes into cells are well known in the art (see, for example, Ausubel, id.).

In accordance with another aspect of the invention, a purified preparation of human hemangioblast cells, in which the cells have been modified to carry a therapeutic gene, may be provided in containers or commercial packages that further comprise instructions for use of the preparation in gene therapy to prevent and/or treat a disease by delivery of the therapeutic gene. Accordingly, the invention further provides a commercial package (i.e., a kit) comprising a preparation of mammalian hemangioblast cells of the invention, wherein the preparation has been modified so that the cells of the preparation carry a therapeutic gene, and instructions for treating a patient having a condition amenable to treatment with gene therapy.

Other Commercial Applications and Methods

Certain aspects of the present invention pertain to the expansion of human hemangioblasts to reach commercial quantities. In particular embodiments, human hemangioblasts are produced on a large scale, stored if necessary, and supplied to hospitals, clinicians or other healthcare facilities. Once a patient presents with an indication such as, for example, ischemia or vascular injury, or is in need of hematopoietic reconstitution, human hemangioblasts can be ordered and provided in a timely manner. Accordingly, the present invention relates to methods of generating and expanding human hemangioblasts to attain cells on a commercial scale, cell preparations comprising human hemangioblasts derived from said methods, as well as methods of providing (i.e., producing, optionally storing, and selling) human hemangioblasts to hospitals and clinicians. Further, hemangioblast lineage cells may be produced in vitro and optionally stored and sold to hospitals and clinicians.

Accordingly certain aspects of the present invention relate to methods of production, storage, and distribution of hemangioblasts expanded by the methods disclosed herein. Following human hemangioblast generation and expansion in vitro, human hemangioblasts may be harvested, purified and optionally stored prior to a patient's treatment. Alternatively, in situations in which hemangioblast lineage cells are desired, human hemangioblasts may be differentiated further in vitro prior to a patient's treatment. Thus in particular embodiments, the present invention provides methods of supplying hemangioblasts to hospitals, healthcare centers, and clinicians, whereby hemangioblasts or hemangioblast lineage cells produced by the methods disclosed herein are stored, ordered on demand by a hospital, healthcare center, or clinician, and administered to a patient in need of hemangioblast or hemangioblast lineage therapy. In alternative embodiments, a hospital, healthcare center, or clinician orders human hemangioblasts based on patient specific data, human hemangioblasts are produced according to the patient's specifications and subsequently supplied to the hospital or clinician placing the order.

Further aspects of the invention relate to a library of hemangioblasts and/or hemangioblast lineage cells that can provide matched cells to potential patient recipients. Accordingly, in one embodiment, the invention provides a method of conducting a pharmaceutical business, comprising the step of providing hemangioblast preparations that are homozygous for at least one histocompatibility antigen, wherein cells are chosen from a bank of such cells comprising a library of human hemangioblasts that can be expanded by the methods disclosed herein, wherein each hemangioblast preparation is hemizygous or homozygous for at least one MHC allele present in the human population, and wherein said bank of hemangioblast cells comprises cells that are each hemizygous or homozygous for a different set of MHC alleles relative to the other members in the bank of cells. As mentioned above, gene targeting or loss of heterozygosity may be used to generate the hemizygous or homozygous MHC allele stem cells used to derive the hemangioblasts. In one embodiment, after a particular hemangioblast cell preparation is chosen to be suitable for a patient, it is thereafter expanded to reach appropriate quantities for patient treatment. Such methods may further comprise the step of differentiating the hemangioblasts to obtain hematopoietic and/or endothelial cells prior to administering cells to the recipient. Methods of conducting a pharmaceutical business may also comprise establishing a distribution system for distributing the preparation for sale or may include establishing a sales group for marketing the pharmaceutical preparation.

Other aspects of the invention relate to the use of the human hemangioblasts of the present invention as a research tool in settings such as a pharmaceutical, chemical, or biotechnology company, a hospital, or an academic or research institution. For example, human hemangioblasts and hemangioblast derivative cells (e.g., endothelial cells) may be used to screen and evaluate angiogenic and anti-angiogenic factors or may be used in tissue engineering. In addition, because the hemangioblasts obtained and expanded by the methods disclosed herein have dual potential to differentiate into hematopoietic and endothelial cells, they may be used for the cellular and molecular biology of hematopoiesis and vasculogenesis. Further, the human hemangioblasts may be used for the discovery of novel markers of these cells, genes, growth factors, and differentiation factors that play a role in hematopoiesis and vasculogenesis, or for drug discovery and the development of screening assays for potentially toxic or protective agents.

In other embodiments of the present invention, hemangioblast lineage cells (such as blood cells) are also used commercially. Hematopoietic cells may be used to generate blood products, such as hemoglobin and growth factors, that may be used for clinical and research applications.

The present invention also includes methods of obtaining human ES cells from a patient and then generating and expanding human hemangioblasts derived from the ES cells. These hemangioblasts may be stored. In addition, these hemangioblasts may be used to treat the patient from which the ES were obtained or a relative of that patient.

As the methods and applications described above relate to treatments, pharmaceutical preparations, and the storing of hemangioblasts, the present invention also relates to solutions of hemangioblasts that are suitable for such applications. The present invention accordingly relates to solutions of hemangioblasts that are suitable for injection into a patient. Such solutions may comprise cells formulated in a physiologically acceptable liquid (e.g., normal saline, buffered saline, or a balanced salt solution). A solution may optionally comprise factors that facilitate cell differentiation in vivo. A solution may be administered to a patient by vascular administration (e.g., intravenous infusion), in accordance with art accepted methods utilized for bone marrow transplantation. In some embodiments, the cell solution is administered into a peripheral vein, a superficial peripheral vein, or alternatively, by central venous administration (e.g., through a central venous catheter). The number of cells in the solution may be at least about $10^2$ and less than about $10^9$ cells. In other embodiments, the number of cells in the solution may range from about $10^1$, $10^2$, $5\times10^2$, $10^3$, $5\times10^3$, $10^4$, $10^5$, $10^6$, $10^7$, or $10^8$ to about $5\times10^2$, $10^3$, $5\times10^3$, $10^4$, $10^5$, $10^6$, $10^7$, $10^8$, or $10^9$, where the upper and lower limits are selected independently, except that the lower limit is always less than the upper limit. Further, the cells may be administered in a single or in multiple administrations.

The present invention will now be more fully described with reference to the following examples, which are illustrative only and should not be considered as limiting the invention described above.

Example 1: Hemangioblasts Derived from Human ES Cells Exhibit Both Hematopoietic and Endothelial Potential The human embryonic stem cell lines H1 and H9 are cultured in ES cell media with mouse embryonic fibroblasts (MEFs). Cultured human ES cells are detached, pelleted by centrifugation at 200 g, and resuspended in embryoid body (EB) formation medium. EB formation medium comprises serum-free Stemline media (Sigma®) supplemented with BMP-4 and VEGF. Cells are then plated on ultra-low attachment culture dishes and cultured in a $CO_2$ incubator. After 24-48 hours, early hematopoietic cytokines (TPO, Flt-3 ligand, and SCF) are added and the cells incubated for another 24-48 hours to form EBs.

Embryoid bodies (EB) are cultured for 2-6 days or optionally 2-5 days and then collected, washed with PBS and disaggregated into single cell suspensions using Trypsin/EDTA. The numbers of EBs are determined and approximately 5-10×$10^6$ cells/mL are cultured in serum-free methylcellulose medium that is optimized for hemangioblast growth comprising BL-CFU medium (Stem Cell Technology™) and that is supplemented with cytokines and a PTD-HOXB4 fusion protein. The cells are then replated onto a new ultra-low attachment culture dish to allow the growth of hemangioblast colonies.

The EBs are monitored daily for the formation of hemangioblast colonies. At approximately 3 days, the formation of hemangioblast colonies are observed. The hemangioblasts are characterized by a very distinctive grape-like cell morphology.

Some of the cells should be able to form EBs again (secondary EBs). The secondary EBs do not have grape-like morphology, as shown in FIG. 16b. The hemangioblasts are also smaller than the secondary EBs.

These hemangioblast colonies are then selected, picked and replated into methylcellulose CFU-medium to test for their capacity to further differentiate and form hematopoietic colony-forming units (CFUs). Similarly, these hemangioblast colonies are selected, picked and replated onto fibronectin-coated culture plates optimized for the first step towards endothelial differentiation.

To test for the generation of hematopoietic progenitor cells from these selected hemangioblast colonies, the growth of colony-forming units (CFU) for granulocytes, erythrocytes, macrophages and megakaryocytes are measured during the next 3-10 days of growth.

To test for the generation of endothelial cells from these isolated hemangioblast colonies, the ability of the hemangioblasts to form branched tube-cords when they are replated into thick layers of Matrigel is examined.

The ability of the isolated hemangioblast colonies to differentiate into endothelial cells could also be confirmed using other endothelial-specific assays, such as LDL uptake or the presence of endothelial cell surface markers.

Example 2: Additional Characterization of hESC-Derived BC Cells or Hemangioblasts Human ES cell culture. The hES cell lines used in this study were previously described H1, H7, and H9 (NIH-registered as WA01, WA07, and WA09) cell lines and four lines (MA01, MA03, MA40, and MA09) derived at Advanced Cell Technology. Undifferentiated human ES cells were cultured on inactivated (mitomycin C-treated) mouse embryonic fibroblast (MEF) cells in complete hES media until they reached 80% confluence (Klimanskaya & McMahon; Approaches of derivation and maintenance of human ES cells: Detailed procedures and alternatives, in *Handbook of Stem Cells. Volume 1: Embryonic Stem Cells*, ed. Lanza, R. et. al. (Elsevier/Academic Press, San Diego, 2004). Then the undifferentiated hES cells were dissociated by 0.05% trypsin-0.53 mM EDTA (Invitrogen™) for 2-5 min and collected by centrifugation at 1,000 rpm for 5 minutes.

EB Formation.

To induce hemangioblast precursor (mesoderm) formation, hES cells (2 to $5 \times 10^5$ cells/ml) were plated on ultra-low attachment dishes (Corning™) in serum-free Stemline media (for e.g., Stemline I or II, Sigma™) with the addition of BMP-4 and $VEGF_{165}$ (50 ng/ml, R&D Systems™) and cultured in 5% $CO_2$. Approximately 48 hours later, the EB medium was replenished and supplemented with a cocktail of early hematopoietic/endothelial growth factors. For example, half the media were removed 48 hours later and fresh media were added with the same final concentrations of BMP-4 and VEGF, plus SCF, TPO and FLT3 ligand (20 ng/ml, R&D Systems). The triple protein transduction domain (tPTD)-HoxB4 fusion protein (1.5 µg/ml) was added to the culture media between 48-72 hr to expand the hemangioblasts and their precursors.

Hemangioblast or Blast Cell Expansion.

After 3.5-5 days, EBs were collected and dissociated by 0.05% trypsin-0.53 mM EDTA (Invitrogen™) for 2-5 min, and a single cell suspension was prepared by passing through 22G needle 3-5 times and a 40 µM strainer. Cells were collected by centrifugation at 1,000 rpm for 5 minutes and counted. Cell pellets were resuspended in 50-200 µl of serum-free Stemline media. To expand hemangioblasts, single cell suspensions from EBs derived from differentiation of 2 to $5 \times 10^5$ hES cells were mixed with 2 ml BL-CFC/ hemangioblast expansion media (BGM) containing 1.0% methylcellulose in Iscove's MDM, 1-2% Bovine serum albumin, 0.1 mM 2-mercaptoethanol and a cocktail of growth factors. For example, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF, 3 to 6 units/ml rh-EPO, 50 ng/ml rh-SCF, 50 ng/ml rh-FLt3 ligand, 50 ng/ml rh-VEGF and 50 ng/ml rh-BMP-4) ("rh" stands for "recombinant human") and 1.5 µg/ml of tPTD-HoxB4 fusion protein, with/without 50 ng/ml of TPO and FL, was added. The cell mixtures were plated on ultra-low attachment dishes (e.g., $2-5 \times 10^5$ cells/2 ml in one well of a six-well plate) and incubated at 37° C. in 5% $CO_2$ for 4-7 days. After 4-6 days, grape-like hemangioblast blast colonies (referred to as BL-CFCs or BCs) were visible by microscopy, as shown in FIG. 16a.

Approximately 0.35±0.01% and 0.52±0.06% of individual cells from WA01 hES cells and MA01 hES cells developed into grape-like blast colonies (BCs), respectively. The BCs contained <10 cells at the beginning of day 3, rapidly expanding from days 4 to 6 to >100 cells (FIG. 16a). The colonies were generally less compact and more morphologically homogenous than secondary EBs (FIG. 16b). Cytospin preparation and Wright-Giemsa staining of the hES-derived blast colonies confirmed morphologic features of immature blast cells (FIG. 16c). To extend these results to other hES cell lines (WA07 [H7], WA09 [H9], MA01, MA03, MA09, and MA40), supplements of FL (50 ng/ml) and Tpo (50 ng/ml) were necessary for sustained growth of the BC colonies (without FL and Tpo, small (10-20 cell) hES-BCs were obtained which died after 4-8 days). The discrepancy observed between different hESC lines may be due to the instrinsic properties of these cell lines as previously observed by Bowles et al. (2006 *Stem Cells* 24: 1359-1369). Epo (3-6 units/ml of human recombinant Epo) was also essential for BC formation and growth in all hES cell lines tested.

A time course was examined (from 2 days to 6 days) of human BL-CFC formation in EBs, and a narrow time period was found during which human ESC-derived EBs generated the greatest numbers of BL-CFCs (or hES-BCs). Day 2 EBs generated hES-BCs at a low frequency ($57.3 \pm 7.4$ BCs/$1 \times 10^5$ EB cells for WA01 hES cells, mean±SE, n=3; $395 \pm 10.4$ BCs/$1 \times 10^5$ EB cells for MA01 hES cells, n=3), and by day 6 only gave rise to hematopoietic (erythroid) progenitors. However, day 3.5 EBs generated large numbers of hemangioblasts or hES-BCs ($347.4 \pm 11.1$ BCs/$1 \times 10^5$ EB cells for WA01 hES cells, n=3; $523.3 \pm 60.1$ BCs/$1 \times 10^5$ EB cells for MA01 hES cells, n=3) in all hESC lines tested, including hESC lines derived from both blastocysts (WA01 and WA09) and single blastomeres (MA01 and MA09). Although efficiencies depended on the hESC line and growth conditions (see Table 1), one 6-well plate of WA01-GFP and MA01 hES cells ($12-13 \times 10^6$ cells) generated approximately $22.18 \pm 3.51 \times 10^6$ (expanded for 6-8 days, mean±SE, n=17), and $49.73 \pm 7.23 \times 10^6$ (expanded for 6-8 days, n=9) and $396.4 \pm 91.63 \times 10^6$ (expanded for 10-13 days, n=6) hemangioblast or hES-BC cells, respectively. Accordingly, the cells could be readily expanded under the well-defined and reproducible conditions described above.

TABLE 1

Efficiency of hES-BC cells derived from different hES cell lines

| hES cell lines | hES-BC cells $(10^5)$*/$1 \times 10^6$ hES cells |
|---|---|
| WA01(H1) | 11.7; 26.7; 8.4; 20.0; 22.8; 31.9; 27.5; 8.4; 10.0; 16.7; 8.8; 14.2; 9.4; 7.5; 10.0; 52.5; and 28.0 (17 experiments)* |
| WA07 (H7) | 6.5 and 17.0 (2 experiments)* |
| WA09 (H9) | 1.8; 2.0; and 2.2 (3 experiments)* |
| MA01 | 22.5; 25.0; 45.0; 42.5; 32.5; 42.8; 27.1; 80.0; and 55.5 (9 experiments)* 156.7; 220.8; 437.5; 192.0; 325.0; and 650.0 (6 experiment)# |
| MA09 | 6.5 and 11.3 (2 experiments)* |
| MA40 | 2.2; 2.5; and 3.0 (3 experiments)* |

*hES-BC cells were collected and purified after culturing in BGM for 6-8 days, then the number of cells was counted using a hemocytometer. The efficiency was calculated based on $2 \times 10^6$ cells/well of hES cells in a standard 6-well plate.
BCs were expanded for 10-13 days.

Cryopreservation of Hemangioblasts.

Hemangioblasts (or blast cells or hES-BC cells) can be cryopreserved with serum-free media. For cryopreservation of hemangioblast cells, purified cells were divided into two identical portions: half of these cells were directly plated for both hematopoietic CFU assay and endothelial cell development, the other half was resuspended in 8% DMSO with Stemline medium and stored in liquid nitrogen. Then cells were thawed and examined for hematopoietic and endothelial development potentials. After thawing, the hemangioblast cells were plated for both hematopoietic and endothelial lineage development as described herein and compared with fresh, purified cells. For endothelial cell lineage, $78 \pm 2\%$ (mean±SE, n=3) of cells were recovered after the freezing process, while 61±7% (n=3) of total hematopoetic CFUs and 46±4% (n=3) of CFU-erythroid were retained as compared to fresh hES-BC cells. No loss of more primitive multipotential progenitors for CFU-mix was observed after recovering hES-BC cells from liquid nitrogen storage.

Characterization of Hemangioblasts.

For BL-CFC immunocytochemical analysis, purified BL-CFCs were cytospun onto polylysine treated glass slides and fixed in 4% paraformaldehyde. For examining the expression of most genes, primary antibodies were incubated at 4° C. overnight, followed by fluorescent dye labeled secondary antibodies, and finally examined under fluorescent microscope. Normal human BM cells, K562 cells and HUVEC were used as controls.

Immunocytochemical analysis revealed that the hES cell-derived BL-CFCs or BCs expressed several hemangioblast related proteins but no CD31, CD34 and KDR, or other adhesion molecules. The hES-BCs expressed GATA-1 (FIGS. 16d and 16e) and GATA-2 proteins. GATA-1 is a zinc finger transcription factor essential for both primitive (embryonic) and definitive (adult) erythropoiesis and is expressed in murine hemangioblastic cells (Ferreira et al. 2005 *Mol Cell Biol* 25: 1215-1227 and Yokomizo et al. 2007 *EMBO J* 26: 184-196). GATA-2 is a zinc finger transcription factor that functions at multiple steps in hemangioblast development and differentiation (Lugus et al. 2007 *Development* 134: 393-405)). The hES cell-derived BL-CFCs or BCs also expressed LMO2 (a LIM-domain protein critical for hemangioblast development (Gering et al. 2003 *Development* 130: 6187-6199) (FIGS. 16g and 16h) and CXCR-4 (FIGS. 16n and 16o). CXCR-4 is the receptor for chemokine SDF-1, which is expressed on the surface of endothelial cells derived from hESCs, hematopoietic stem cells, and mouse hemangiocytes. CXCR-4 plays an important role in the migration, retention, and development of hematopoietic progenitors in the bone marrow. The cells additionally expressed TPO and EPO receptors (FIGS. 16t and 16u, and 16q and 16r, and Table 1), and readily reacted with antibody specific for CD71, the transferrin receptor (FIGS. 16j and 16k) (see Table 2 and FIG. 16d-v). The cells expressed little or no CD31, CD34 and KDR, or other adhesion molecules (Table 2). The absence of CD34, CD31, and KDR expression, and the absence of CD133 expression, is a unique profile of surface marker expression.

For gene profiling analysis, total RNA was isolated from purified BL-CFCs/hES-BC cells, 3.5 day-EBs and undifferentiated ES cells using the RNAeasy kit (Qiagen). Fragmented antisense cRNA was used for hybridizing with human U133.2 arrays (Affymetrix®, Inc) at the Core Genomic Facility of University of Massachusetts (Worcester, Mass.). For expression profiling of the β-cluster globin genes, individual CFU colonies were picked up, RNA was isolated and amplified, and β-, γ- and ε-globin gene expression was analyzed as described previously (Lu et al. 2004 *Blood* (103): 4134-4141).

Molecular profiling by Affymetrix™ Arrays indicated a significant increase in genes associated with hemangioblast and early primitive erythroblast development as compared to early-stage EBs (Table 2). SCL and LMO2, two genes critical for hemangioblast development (D'Souza et al. 2005 *Blood* (105): 3862-3870; Park et al. 2004 *Development* (131): 2749-2762; Gering et al. 2003 *Development* (130): 6187-6199)), as well as FLT-1 (a receptor for VEGF) were readily detectable in the BL-CFCs/blast colonies. Embryonic (ε-globin, 549-fold) and fetal (γ-globin, 817-fold) globin gene expression was dramatically increased in the BL-CFCs/hES-BCs; NF-E2 (12-fold), GATA-1 (6-fold), EKLF (7-fold), ICAM-4 (4-fold), glycophorins (14-fold) and Epo receptor (4-fold) message levels were also moderately increased.

TABLE 2

Characterization of BL-CFC (hES-BCs) by Affymetrix Arrays and Immunocytochemistry

| Affymetrix Arrays | | | Immunocytochemistry | |
|---|---|---|---|---|
| Genes | EBs | BL-CFC | Antibodies | BL-CFC |
| Hemangioblasts | | | GATA-1 | + |
| | | | GATA-2 | + |
| TAL1/SCL | − | + | β-catenin | + |
| LMO2 | + | +↑ | CXCR-4 | + |
| GATA-2 | + | + | Tpo-receptor | + |
| FLT1 | − | + | Epo-receptor | + |
| | | | EGR-1 | + |
| HSC and Erythrioblast | | | CD71 (transferrin receptor) | + |
| | | | Neurokinin B1 | + |
| Epo-receptor | + | +↑ | KDR | − |
| c-Kit | + | − | PECAM-1 (CD31) | − |
| CXCR-4 | + | + | VE-cadherin | − |
| GATA-1 | − | + | CD34 | − |
| NF-E2 | − | + | OCT-4 | − |
| EKLF | − | + | Nanog | − |
| ICAM4 (CD242) | − | + | TRA-I-88 | − |
| Band3 (CD233) | − | + | SSEA-4 | − |
| Band7.2 | + | − | CD41 | − |
| Glycophorins | − | + | CD43 | − |
| Arkrin-1 | − | + | Integrin α4 | ± |
| c-Myc | + | +↑ | Integrin β1 | ± |
| ε-Globin | − | + | | |
| γ-Globin | − | + | | |
| PF-4 | − | + | | |
| PDGF-R2 (CD140A) | + | − | | |
| Pim-1 | + | +↑ | | |
| Endothelial Cell | | | | |
| Tie-2 | + | − | | |
| VE-cadherin | − | + | | |
| MADCAM1 | − | + | | |
| DOC1 | − | + | | |
| EZFIT | − | + | | |
| Integrin β3 (CD61) | − | + | | |
| Selectin-P (CD62) | − | + | | |
| VEGF | + | − | | |
| Undifferentiated ES Cell | | | | |
| OCT-4 | + | − | | |
| TRA-1 | + | +↓ | | |
| Wnt5a | + | − | | |
| FGF-R | + | +↓ | | |
| FGF-R2 | + | − | | |
| FGF-R3 | + | − | | |
| Mesoderm | | | | |
| BMP-4 | + | − | | |
| BMP-2 | + | − | | |
| BMP-7 | − | + | | |
| BMP-R1A | + | − | | |
| AVC-R2B | + | +↓ | | |
| MEST | + | +↓ | | |
| Brunchy T | + | − | | |
| Adhesion molecules | | | | |
| E-cadherin | + | − | | |
| P-cadherin | + | − | | |
| N-cadherin | + | +↓ | | |
| Integrin β5 | + | − | | |
| Integrin β1 | + | +↓ | | |
| Connexin 43 | + | +↓ | | |

For immunochemistry: +, moderate to strong staining; −, negative staining; ±, very weak staining.
For Affymetrix Arrays: +, expression level above background; −, expression level below background; +↑, expression level in BL-CFC is higher than expression level in EBs; +↓, expression level in BL-CFC is lower than expression level in EBs.

Functional Characterization of Hemangioblasts.

The grape-like hemangioblast colonies were picked and isolated manually under dissection microscope and resuspended in serum-free Stemline (Stemline I) media. The cells were then tested for lineage potential by the methods described below.

Clonality of hES-Blast Cells.

To determine whether hES-blast colonies were clonal and originated from a common bipotential progenitor cell, cell mixing experiments were performed as previously described in mouse studies (Choi et al. 1998 *Development* (125): 725-732; Kennedy et al. 1997 *Nature* (386): 488-493). Cells from EBs of WA01-GFP and MA01 hES cells were mixed and plated in BGM. hES-blast colonies were examined 4-6 hours later by phase and fluorescence microscopy. In a series of three experiments, 100% (77 out of 77) of the blast colonies were found to be either GFP positive or GFP negative (no mixed BCs were observed, FIGS. 18*a* and 18*b*).

To rule out the possibility that the GFP negative colonies contained cells with an inactive GFP gene, GFP positive and GFP negative colonies were examined for the presence of GFP sequence. Twelve individual GFP positive and twelve individual GFP negative colonies from the mixing experiments were handpicked under phase and fluorescence microscopy. Genomic DNA was isolated by a MicroDNA kit (Qiagen™), and GFP specific PCR reactions were performed. As an internal control for the PCR reactions, myogenin primers were included in all PCR reactions, which generate a fragment of 245 bp. PCR products were separated on a 2% agarose gel and visualized by ethidium bromide staining. The polymerase chain reaction (PCR) analysis confirmed the absence of the GFP gene sequence in all negative colonies (FIG. 18, PCR analysis)).

Dilution studies further confirmed the clonogenicity of both primary and secondary BCs (Table 3, FIG. 18*c*). Limited dilution studies were carried out using different numbers of cells (from $1.5 \times 10^3$ to $1.5 \times 10^4$) from differentiated EBs. After diluting single EB-cell suspensions with 150 ml BGM (100 cells/ml), they were plated in 15 ultra-low 96-well plates and incubated at 37° C. for BC development. To confirm the clonal origin of blast colonies, the plates were checked under masked conditions by two associates 4 hours after plating. Wells with double or triple cell clumps were excluded from further investigation.

As reported by Kennedy et al. (1997 *Nature* 386: 488-493) in mouse ES cell studies, human blast colony (hES-BC or BC) development was also cell density dependent with poor development at low cell number. Seven BCs developed from fifteen 96-well plates (FIG. 18*c*). Additional limiting dilution studies were performed to determine whether the BCs contained cells that have the potential to generate secondary BCs.

For secondary BC growth, primary blast colonies were handpicked and dissociated into single cells. The single cells were then mixed (200, 300, and 1000 cells, respectively) with 20 ml BGM to make serial dilutions and plated in six ultra-low 96-well plates (0.1 ml/well). Wells with double or triple cell clumps were excluded from the study. A total of 29 secondary BCs with identical morphological characteristics as primary BCs developed from five 96-well plates. These experiments confirmed the clonogenicity of both primary and secondary hES-BCs (Table 3).

Bipotential Capacity of hES-Blast Colonies.

Two strategies were used to demonstrate the bipotential capacity of clonally-derived blast cells. In the first method, for single BC expansion, individual hES-BC colonies were handpicked and transferred to a fibronectin-coated 48-well plate containing Stemline II with growth factors supporting the growth of hematopoietic and endothelial lineages. The growth factors in the liquid cultures included recombinant human SCF (20 ng/ml), Tpo (20 ng/ml), FL (20 ng/ml), IL-3 (20 ng/ml) VEGF (20 ng/ml), G-CSF (20n ng/ml), BMP-4 (15 ng/ml), IL-6 (10 ng/ml), IGF-1 (10 ng/ml), endothelial cell growth supplement (ECGS, 100 µg/ml) and Epo (3 U/ml). Following one week in culture, non-adherent hematopoietic cells were removed by gentle pipetting and used directly for hematopoietic CFU assay. Following removal of the non-adherent cells, the adherent populations were cultured for one more week in EGM-2 endothelial cell medium (Cambrex™), and then examined for the expression of vWF.

When individual BL-CFCs were transferred to liquid cultures containing growth factors supporting the growth of both hematopoietic and endothelial lineages, both non-adherent and adherent cells developed in more than 60% (15 of 24) BL-CFCs (FIGS. 18*d* and 18*e*, Table 2); 65% (16 of 24) of them formed hematopoietic colonies including erythroid (FIG. 18*i*), myeloid (FIGS. 18*j* and 18*k*) and multilineage (FIG. 18*l*) after replating in semi-solid medium supplemented with a spectrum of hematopoietic cytokines. Over 95% (23 of 24) of the individual BCs generated adherent, stromal-like cells, which formed capillary-vascular structures on Matrigel (FIG. 18*f*) that took up Ac-LDL (FIG. 18*g*) and expressed vWF (FIG. 18*h*).

In the second method, individual BCs from both primary and secondary blast cell colonies were picked and split into two groups; one group was tested for hematopoietic CFU and the other group was tested for endothelial progenitor formation. For primary BCs, over 90% (22 of 24) gave rise to both hematopoetic and endothelial lineages; 100% and 92% developed hematopoetic and endothelial cells, respectively (Table 3). Similarly, seven individual BCs from limiting dilution experiments were also examined for their potential to differentiate into hematopoietic and endothelial lineages. Five BCs generated both hematopoietic and endothelial progeny (Table 3), showing a lower efficiency than as compared with BCs from regular experiments (71% vs. 92%), possibly due to the non-optimal conditions of development. For the 29 secondary BCs, over half (15 of 29) gave rise to both hematopoetic and endothelial lineages, whereas 6 (21%) and 3 (10%) generated only hematopoetic or endothelial cells, respectively (Table 3). Although the primary BCs contained heterogeneous populations, including precursors of hematopoietic and endothelial cells, the secondary limiting dilution experiments clearly demonstrate the existence of hemangioblasts in primary BCs.

TABLE 3

Hematopoietic and endothelial lineage development from clonally-derived blast colonies

| | No. colonies | Hematopoietic lineage (%) | Endothelial lineage(%) | Hematopoietic and endothdelial lineages (%) |
|---|---|---|---|---|
| Primary BCs * | 24 | 16 (67) | 23 (96) | 15 (62) |
| Primary BCs ** | 24 | 24 (100) | 22 (92) | 22 (92) |
| Primary BCs derived from limited dilution | 7 | 6 (86) | 6 (86) | 5 (71) |
| Secondary BCs | 29 | 21 (72) | 20 (69) | 15 (52) |

\* Individual BCs were transferred to liquid cultures containing both hematopoietic and endothelial cytokines on fibronectin coated plastic wells. After 1 week of culture, the non-adherent and adherent cells were removed and examined for hematopoietic CFU and endothelial cell development.
\*\* Individual BCs were transferred to EGM-2 media; half of the cells were cultured on fibronectin coated wells for endothelial lineage development, and the other half plated directly for hematopoietic CFU assay.

Hematopoietic Progenitor Assay.

For the hematopoietic progenitor assay, half of the cells were mixed with 1 ml of serum-free hematopoietic colony-forming-unit (CFU) media (H4436, Stem Cell Technologies™) plus 1.5 µg/ml of tPTD-HoxB4 and 0.5% EX-CYTE (Serologicals Proteins Inc.™). Cells may also be mixed with serum-free hematopoetic colony-forming cell assay media containing 1.0% methylcellulose in Iscove's MDM, 1-2% Bovine serum albumin, 0.1 mM 2-mercaptoethanol, 10 µg/ml rh-Insulin, 200 µg/ml iron saturated human transferrin, 20 ng/ml rh-GM-CSF, 20 ng/ml rh-IL-3, 20 ng/ml rh-IL-6, 20 ng/ml rh-G-CSF, 3 units/ml rh-Epo, 50 ng/ml rh-SCF) and 1.5 to 5 µg/ml of PTD-HoxB4 fusion protein. The cell mixtures were plated on untreated 12-well cell culture plates, and incubated at 37° C. for 10-14 days.

Hematopoietic CFUs were examined under the microscope 10-14 days after initial plating. For morphological characterization, single hematopoietic CFU were picked and washed twice with PBS, cytospun on to a glass slide, stained with Wright-Giemsa dye, and cell morphology was examined under a microscope.

As an illustration of the hematopoietic potential of hemangioblasts, hematopoietic CFUs were observed from hemangioblasts that were generated from H1-GFP ES cells, as shown in FIG. 1.

The morphologies of other hematopoietic CFUs that were observed are illustrated in FIGS. 2-6. The CFUs for erythrocytes (CFU-E) were characterized by the morphology displayed in FIG. 2. The multipotent CFUs (CFU-GEMM/Mix) were characterized by the morphology displayed in FIGS. 3 and 4. The CFUs for granulocytes (CFU-G) and macrophage (CFU-M) were characterized by the morphology displayed in FIG. 5. The CFUs for granulocyte/macrophage (CFU-GM) and megakaryocyte macrophage (CFU-Mk) were characterized by the morphology displayed in FIG. 6.

As another illustration of the hematopoietic potential of hemangioblasts, colonies of erythroid (FIG. 17a), granulocyte (FIG. 17b), macrophage (FIG. 17c) and multilineage (FIG. 17d) hematopoietic cells were also observed when single-cell suspensions were plated in serum-free methylcellulose media containing the spectrum of cytokines discussed above for 10 to 14 days. Wright-Giemsa staining (FIG. 17e-g), immunostaining (FIG. 17i-k) and FACS analysis (FIG. 17v-y) using antibodies against CD235a (erythrocytes), CD13 (myeloid) and CD45 (leukocytes) confirmed the identity of their hematopoietic lineages. Most CFUs (>50%) were multilineage with an erythroid core and formed within a few days after plating (see FIG. 1 for example).

Figure 17A:
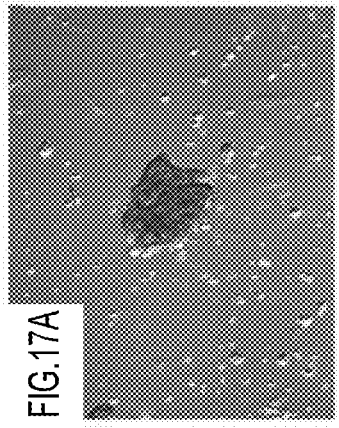
FIG. 17a-17cc illustrates the functional characterization of hemangioblasts (BL-CFC or blast cells) derived from human ES cells in vitro: 17a-17d Hematopoietic CFUs derived from purified hemangioblasts: 17a CFU-erythroid (×lOO); 17b CFU-granulocyte (×lOO); 17c CFU-macrophage; and 17d CFU-multilineage (mix, ×lOO); 17e-17h Wright-Giemsa staining of CFU-cells: 17e erythroid (×1000); 17f granulocyte (×1000); 17g macrophage (×400) and 17h, mix (×1000). 17i-17k Immunostaining of CFU cells: 17i CFU-erythroid cells stained with CD235a (arrows, ×1000); 17j CFU-granulocyte cells stained with CD13 (arrows, ×1000) and 16 k CFU-mix cells stained with CD45 (arrows, ×1000). 17m-17p and 17v-17y FACS analysis of pooled CFU cells: 17m mouse IgG isoytype control; 17n CD45; 17o CD13 and 17p CD235; 17v mouse IgG isotype controls; 17w CD45 and CD235a; 17x CD13 and CD45; and 17y CD13 and CD235a. 17q-17u and 17z-17cc Endothelial cells derived from purified hemangioblasts, or blast cells or hES-BC cells: 17q Capillary tube-like structures formed on Matrigel after plating adherent cells derived from hemangioblasts (×100); 17r Ac-LDL uptake (gray) by endothelial cells derived from hemangioblasts (×200); 17s Expression of vWF (arrows) in hemangioblast-derived endothelial cells, nuclei were stained with DAPI (×600); 17t Localization of PEC AMI (bright staining) in hemangioblast-derived endothelial cells, nuclei (round features in the figure) were stained with DAPI (×200); 17u Localization of VE-cadherin (arrows) in hemangioblast-derived endothelial cells, nuclei (round features) were stained with DAPI (×200). 17z Ac-LDL update (arrow heads) and vWF expression (arrows, ×600); 17aa uptake of Ac-LDL (arrow heads) and expression of VE-candherin (arrows, ×600); 17bb expression of vWF (arrows) and CD31 (arrow heads, ×600); 17cc expression of VE-candherin (arrows) and CD31 (arrow heads, ×600). See Example 2.
Figure 17B:
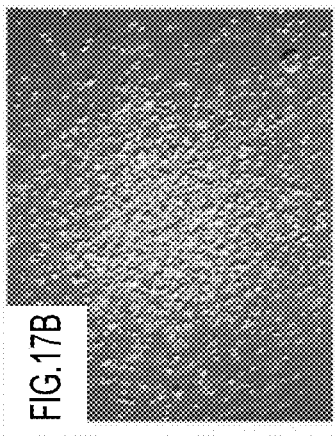
Figure 17C:
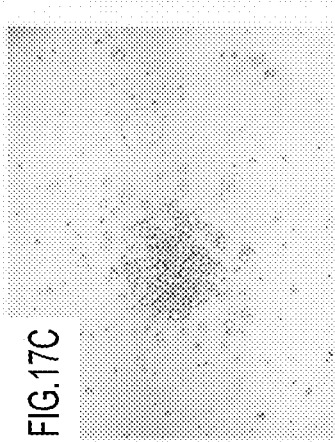
Figure 17D:
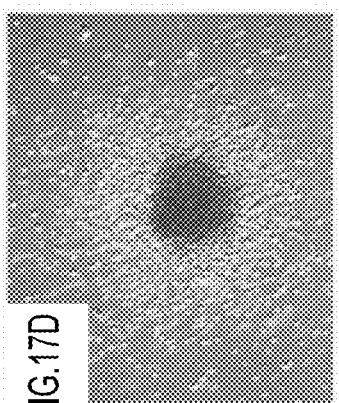
Figure 17E:
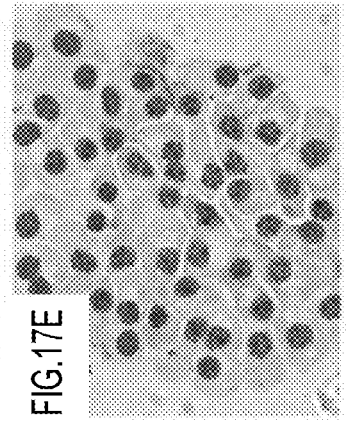
Figure 17F:
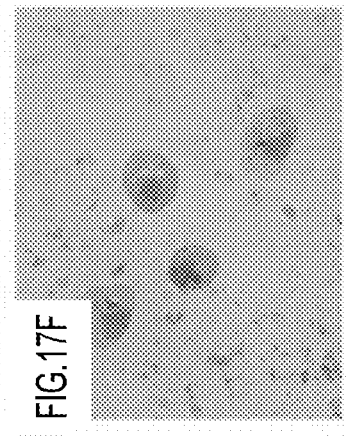
Figure 17G:
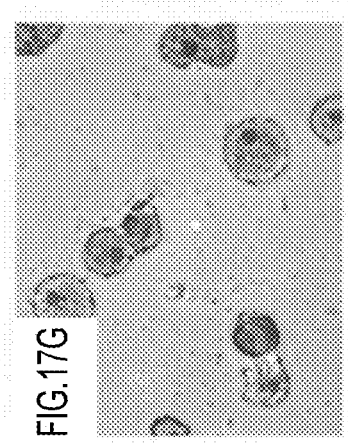
Figure 17H:
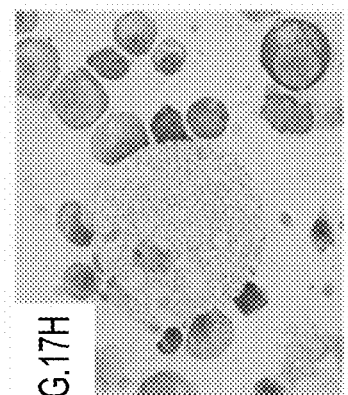

Erythroid colonies resembled that of primitive erythroid with brilliant red color, Wright-Giemsa staining showed all erythroids were nucleated (FIG. 17e-g). To further distinguish the developmental stage of the erythroids, CFU colonies were analyzed for the expression patterns of the β-cluster globin genes (Lu et al. 2004 *Blood* (103): 4134-4141). All the erythroid and multilineage colonies expressed mainly the embryonic ε-globin gene; no β-globin gene message was detected (data not shown), suggesting a primitive yolk-sac-like status.

For immunological characterization, CFU-E, CFU-G, and CFU-Mix cells cytospun onto glass slides were stained with anti-human CD235a, CD13, and CD45 antibodies. For the FACS analysis presented in FIGS. 17 m-p, CFU cells collected from one well were stained with mouse IgG1 isotype control, CD235a, CD13, and CD45 and analyzed by a Coulter flow cytometer. The Wright-Giemsa staining, immunostaining, and FACS analysis confirmed the identity of their hematopoietic lineages (FIGS. 17e-p).

For the FACS analysis presented in FIGS. 17v-y, three-color cytometric analysis was performed using standard procedures on a LSRII flow cytometer (BD Biosciences™). Cells were collected from a well with multiple types of hematopoietic CFUs and isolated by diluting methylcellulose with 5 volumes of IMDM medium. The single cell suspension was aliquoted and stained with either isotype controls or antigen-specific antibodies. The antibody combinations used were CD235a conjugated to fluorescein-isothiocyanate (FITC), CD45 conjugated to R-Phycoerythrin (R-PE), and CD13 conjugated to—allophycocyanin (APC). An aliquot of cells was also—stained with mouse IgG conjugated to FITC, PE, and APC as isotype controls (BD Bioscience™) Samples were run on a LSRII flow cytometer and analyzed with FlowJo™ version 6.3.2 software.

Endothelial Progenitor Assay.

For the endothelial progenitor assay, the other half of cells was plated on a fibronectin coated plate (BD Bioscience™) in EGM-2 or EGM-2MV complete media (Cambrex™) for 3-7 days. The ability of the isolated hemangioblast colonies to differentiate into endothelial cells was also confirmed using tube formation on Matrigel, LDL uptake and immunohistochemistry to detect the presence of endothelial cell surface markers.

Tube Formation on Matrigel.

Figure 7B:
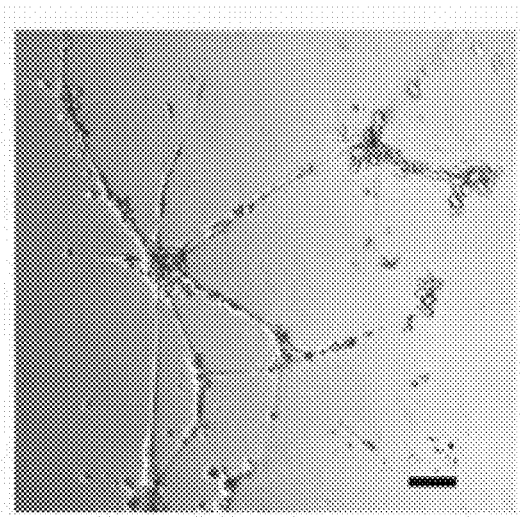

Matrigel (BD Bioscience™) was added to each well of a 4-well tissue culture plate (0.2 ml) or a 96-well pate (0.05 ml) and allowed to solidify at 37° C. for 45 to 90 min. After gelation, 0.2-0.3 ml (e.g., 0.1 ml for a 96-well plate) of cell suspension in EGM-2 or EGM-2MV media containing 0.5 to $1.5 \times 10^5$ cells derived from the above culture was placed on top of the Matrigel, and incubated at 37° C., 5% $CO_2$. Formation of capillary-like (tube) structures was checked after 16-24 hr incubation. FIG. 7 depicts a representative photograph of tube-cord formation of hemangioblasts derived from H9 (a) and ACT30 (b) cells; following replating on Matrigel based medium, the hemangioblasts gave rise to adherent cells that formed capillary-vascular like structures and that also took up Ac-LDL. FIG. 8(a) also depicts a representative photograph of tube-cord structure of hemangioblasts with endothelial potential that were derived from H1-GFP cells. FIG. 17q also depicts the capillary tube-like structures formed on Matrigel after replating the adherent cells derived from hemangioblasts. Such cells were also able to take up AC-LDL (data not shown).

Ac-LDL Uptake.

Hemangioblasts grown for 3-7 days on fibronectin coated wells were added with 10 µg/ml of Alexa Fluor 647-labeled AC-LDL (Invitrogen™) and incubated for 4-6 hr. The cells were then washed 3 times with 1×PBS and fixed with 4% paraformaldehyde for 30 min. The uptake of AC-LDL was visualized under a fluorescent microscope. For example, FIG. 8b illustrates the uptake of AC-LDL of hemangioblasts derived from H1-GFP cells. FIGS. 17z and 17aa also illustrate that incubation with AlexaFluor 594 labeled AC-LDL revealed a punctuate staining pattern characteristic of endothelial cells.

Immunocytochemistry.

Hemangioblasts grown for 3-7 days on fibronectin coated wells were washed 3 times with 1×PBS and fixed with 4% paraformaldehyde for 30 min. For the expression of von Willebrand factor (vWF), PECAM-1 (CD31), VE-cadherin, KDR and CD34, cells were permeabilized and then incubated with primary anti-human vWF (Dako™ or Chemicon™), PECAM-1 and KDR (Cell Signaling Technologies™), VE-cadherin (R&D Systems™), and CD34 (Dako) antibodies respectively overnight at 4° C., then incubated with corresponding secondary antibodies labeled with Rhodamine or FITC (Jackson Laboratory™) for 30-60 min. The expression of the vWF protein was also detected by incubating with a goat anti-mouse IgG-Alexa Fluor 647 secondary antibody (Jackson Laboratory™) for 30-60 min. After final wash, cells were checked under a fluorescent microscope. FIG. 9 illustrates the expression of vWF in hemangioblasts that were derived from H1-GFP ES cells. FIG. 17s also illustrates the expression of vWF (arrows) in hemangioblasts-derived endothelial cells. Adherent cells in blood vessel-like structures were positive for PECAM-1 (CD31), KDR and VE-cadherin (FIGS. 17t, 17u, and 17z-17cc).

Neo-vessel formation was also observed when adherent cells or handpicked BL-CFCs were mixed with Matrigel and implanted in vivo for 4-5 weeks. Histological examination of the Matrigel plugs confirmed the presence of microvessels that were immunoreactive with human specific nuclei and vWF antibodies. See FIGS. 10 and 11.

Example 3: Method of Producing and Purifying an Exemplary HOXB4 Protein

An exemplary HOXB4 protein is made and purified. This is a TAT-HA-HOXB4 fusion protein.

A pTAT-HA-HOXB4 expression vector was generated by cloning a PCR fragment (sense primer 5'-TAC CTA CCC ATG GAC CAC TCG CCC-3' (SEQ ID NO: 16) and antisense primer 5'-TCG TGG CTC CCG AAT TCG GGG GCA-3' (SEQ ID NO: 17) encompassing the HoxB4 open reading frame with and without N-terminal 32 amino acids into the NcoI and EcoRI sites of pTAT-HA expression vector (a gift from Dr. SF. Dowdy, University of California San Diego, La Jolla, Calif.), which contains an N-terminal TAT PTD. The generated pTAT-HA-HoxB4 plasmid was confirmed by sequence analysis and transformed into BL21 (DE3)pLysS bacteria (Invitrogene™).

Bacterial cells growing at log phase were induced with 1 mM IPTG at 30 C for 4 hours and collected by centrifugation. Since the 6×His-fused recombinant TAT-HoxB4 protein was found to be sequestered into inclusion bodies by the host bacteria, the cells were disrupted by sonication in denaturation solution (6 M guanidinium, 20 mM NaPO$_4$, and 0.5 M NaCl, pH 7.8) and the 6×His-fused TAT-HoxB4 recombinant proteins were then bound to nickel resins (ProBond resin, Invitrogen™).

After several washings, the TAT-HoxB4 fusion proteins were eluted in 20 mM NaPO$_4$, pH 4.0, 0.5 M NaCl, 8 M urea plus 10 mM imidazole. The TAT-HoxB4 fusion proteins were then desalted on a Sephadex G-25 column into IMDM medium, aliquoted and stored at −80° C. immediately.

The purity and concentration of the TAT-HoxB4 fusion proteins were determined by SDS-PAGE gel electrophoresis and visualized with Coomassie blue staining. The purified TAT-HA-HoxB4 recombinant protein runs as a ≈37 KD protein. The concentration of the purified TAT-HA-HoxB4 protein was estimated by comparison with a BSA protein standard in the same gel.

Based on computer modeling, Ho et al. (2001 *Cancer Res* 61: 474-477) demonstrated that a modified PTD possesses significantly enhanced protein transduction potential compared with the native TAT PTD, both in vitro and in vivo. To produce the modified PTD-HA-HoxB4 fusion protein, sense 5'-CGA TGG GGA TCC GGC TAC GCA CGC GCA GCT GCG CGC CAG GCT CGC GCC GGT GGA TCC ACC ATG-3' (SEQ ID NO: 18) and antisense 5'-CAT GGT GGA TCC ACC GGC GGC GCG AGC CTG GCG CGC AGC TGC GCG TGC GTA GCC GGA TCC CCA TCG-3' (SEQ ID NO: 19) oligos were digested with BamHI and purified using a kit (Qiagen™). Then TAT fragment in pTAT-HA-HoxB4 plasmid was replaced with the modified PTD fragment, and triplicated PTD inserts were selected based on restriction fragment size and confirmed by DNA sequence analysis. This plasmid is referred to as ptPTD-HA-HoxB4. pTAT-HA-HoxB4 and ptPTD-HA-HoxB4 plasmids were transformed into BL21(DE3)pLysS bacteria (Invitrogen™), and HoxB4 fusion protein expression was induced by the addition of 1 mM IPTG at 30° C. for 4 h. The 6×His-fused recombinant TAT-HoxB4 and tPTD-HoxB4 proteins were sequestered into inclusion bodies by the host bacteria, so the cells were disrupted by sonication in denaturation solution (6 M guanidinium, 20 mM NaPO$_4$, and 0.5 M NaCl, pH 7.8) and the 6×His-fused TAT-HoxB4 and tPTD-HoxB4 recombinant proteins were then bound to nickel resins (ProBond resin, Invitrogen™) After several washings, the TAT-HoxB4 and tPTD-HoxB4 fusion proteins were eluted in 20 mM NaPO4, pH 4.0, 0.5 M NaCl, 8 M urea plus 10 mM imidazole. The TAT-HoxB4 and tPTD-HoxB4 fusion proteins were then desalted in Sephadex G-25 columns into IMDM medium, and aliquoted and stored at −80° C. immediately. The purity and concentration of the TAT-HoxB4 and tPTD-HoxB4 fusion proteins were determined by SDS-PAGE gel electrophoresis and visualized with Coomassie blue staining. The purified TAT-HoxB4 and tPTD-HoxB4 recombinant proteins ran as ≈38 KD proteins. The concentrations of the purified TAT-HoxB4 and tPTD-HoxB4 proteins were estimated by comparison with a BSA protein standard in the same gel. For stability assays, TAT-HoxB4 and tPTDHoxB4 proteins were added to IMDM medium with 5% FBS or Stemline II medium with live hESCs in Ultra low 24-well plates and incubated at 37° C. Aliquots of the medium were removed at different times and subjected for SDS-PAGE gel electrophoresis, and visualized with Coomassie blue staining.

Beslu et al. (2002 *Blood* 100: 22a) have reported that the first 31 amino acids of the N-terminus of HoxB4 are dispensable for its function, and that the removal of the N-terminal 33 amino acids generates a more stable protein. The results confirmed that the full length TAT-HoxB4 protein was unstable, forming a ≈30 KD protein after several thawing cycles, whereas the N-terminus-deleted TAT-HoxB4 and tPTD-HoxB4 proteins retained their integrity after repeated thawing and overnight incubation at 37° C. (FIG. 19C). As shown in FIG. 19A, tPTD-HoxB4 and TATHoxB4 were relatively pure proteins after multiple column chromatography under denaturing conditions and desalting. The purified tPTD-HoxB4 protein ran as a single ≈38 KD band under native SDS-PAGE, with a maximum solubility in PBS or IMDM medium of 250 to 300 µg/ml as estimated by comparison with BSA protein standards. Similar results were obtained from the TAT-HoxB4 fusion protein.

Krosl et al. (2003 *Nat Medicine* 9: 1428-1432) have observed that TAT-HoxB4 protein is very unstable in environments containing FBS and it has to be refreshed every second hour in order to retain biological function. The results presented here confirmed that tPTD-HoxB4 was labile in medium containing 5% FBS, with a half life less than one hour (FIG. 19B); pretreatment of FBS at 70° C. for 30 minutes eliminated most of the enzymatic activity. To further examine its stability, tPTD-HoxB4 protein was added to serum free Stemline medium and cultured with hESCs at 37° C. As shown in FIG. 19C, a substantial fraction of tPTD-HoxB4 protein could be detected, even after 48 h of culture with hESCs.

Example 4: Matrigel Plugs Transplanted into SCID Mice Give Rise to Endothelial Cells Hemangioblast-derived endothelial cells or pure hemangioblasts ($1 \times 10^6$ cells) derived from H1-GFP human ES cells were purified and resuspended in 700 µl of Matrigel (BD Biosciences™). These cells were injected subcutaneously in the dorsal region of 4-week-old SCID mice (Jackson Laboratory™). Five weeks after injection, the Matrigel plugs were removed from the animals and frozen sections were prepared from the plugs. Cross sections of the Matrigel plugs were fixed, and stained by standard hematoxylin and eosin (H&E) staining, as well as immunohistochemistry using an anti-human specific nuclei antibody (MAB1281, Chemicon™) and human specific anti-vWF antibody, followed by fluorescent dye labeled corresponding secondary antibodies (goat anti-mouse IgG-Texas Red secondary antibody for MAB1281). FIG. 10 demonstrates vessels in cross sections of Matrigel plugs with H&E staining; and FIG. 11 demonstrates that the vessels in cross sections of Matrigel plugs are cells derived from human hemangioblasts, which are positive for human specific nuclei antibody.

Example 5: In Vivo Ischemia/Reperfusion Studies of the Eye

Two techniques, intravitreal injection and adoptive transfer, were used to directly examine the contribution of the hES-derived hemangioblasts to the in vivo repair process. Ischemia/reperfusion (I/R) injury was induced by elevation of the intraocular pressure. This model of I/R injury results in damage to the retinal endothelium including vaso-obliteration and generation of acellular capillaries. Seven days following retinal I/R injury, the mice were injected either systemically via the retro-orbital sinus (n=13) or intravitereally (n=4) with fluorescently labeled hemangioblast (also referred to as "hES-BC") cells collected from day 6 hES-BCs.

One day following injection, the mice were euthanized and the retinas removed and labeled with rhodamine-conjugated *Ricinus communis* agglutinin I. This agglutinin binds to glycoproteins expressed specifically by endothelial cells and thus is used to fluorescently label the exterior surfaces of blood vessels.

Figure 20A:
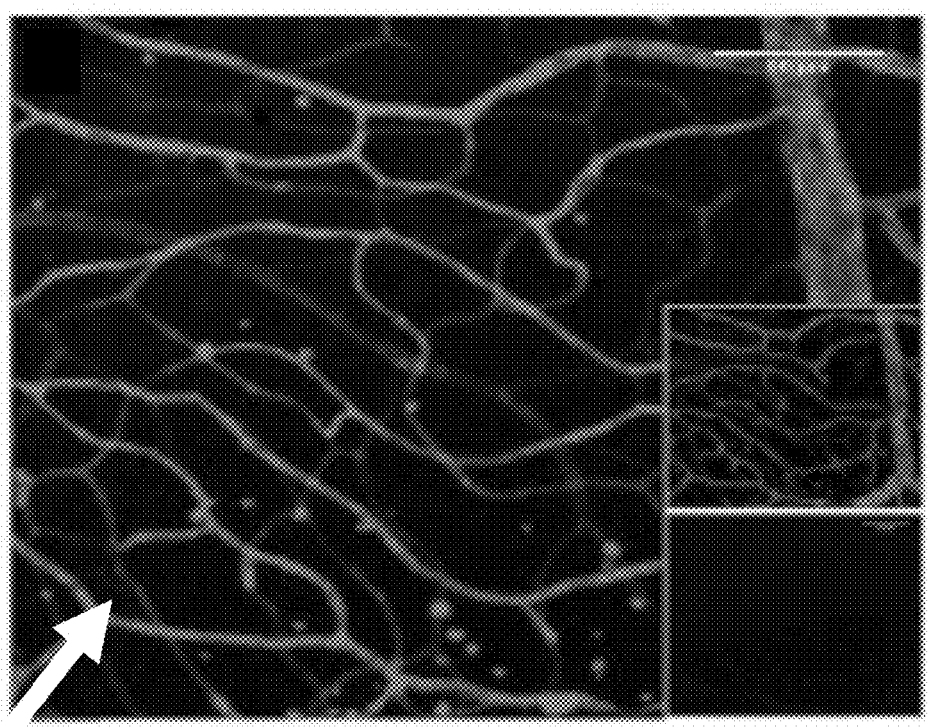

Confocal microscopy demonstrated green fluorescent labeling for hemangioblast (hES-BC) derived endothelial cells, which represented 33.5±10% of the retinal vasculature in the injured eye. No green fluorescence was observed in the control eye (FIGS. 20a and 20b, respectively), demonstrating that the hemangioblast (hES-BC) cells homed to acellular regions where they assimilated into injured regions only, resulting in reendothelialization of non-perfused acellular capillaries within the injured retina (FIGS. 21a and 21b). This repair process was observed in all (n=17) animals in a uniform manner.

A second set of animals with I/R injury (n=6) were handled as described above, and were then, prior to sacrifice, perfusion-fixed with 3-5 ml of TRITC-conjugated dextran in order to visualize vascular lumens of vessels and to conclusively demonstrate that vessels repaired by these cells were patent and thus functional. Red staining depicted patent vessels, green staining demonstrated the hemangioblast (hES-BC) derived endothelial cells, and yellow staining showed where hemangioblast (hES-BC) cells have generated a patent vasculature. FIG. 21d shows a large vessel with yellow (red and green, appearing as light gray) fluorescence two days after hES-BC cell injection, indicating that the cells had incorporated into the vascular wall and that the vessel was perfused. Particularly striking in these animals was the large number of microvessels that were observed to be only green, which appeared to represent new collateral compensatory neovasculature that had not yet matured enough to develop patent lumens, and therefore remained nonperfused with TRITC-dextran. FIG. 20c shows the uninjured control eye of the same animal and clearly demonstrates that BC cells were not in any way associated with vasculature that has had no injury. In retinal flatmounts from mice sacrificed 7 days following hES-BC cell injection, the number of green tubes (non-lumenized, non-perfused vessels) was less compared to mice sacrificed on day 2. There were more yellow vessels (appearing as light gray or white) representing hES-BC cell derived vessels (green) perfused with TRITC-dextran (red). These represented fully functional vessels and demonstrated that hemangioblast (hES-BC) cells had incorporated into vessels of injured eyes which resulted in more areas with perfused microvessels (FIG. 20e).

Figure 20B:
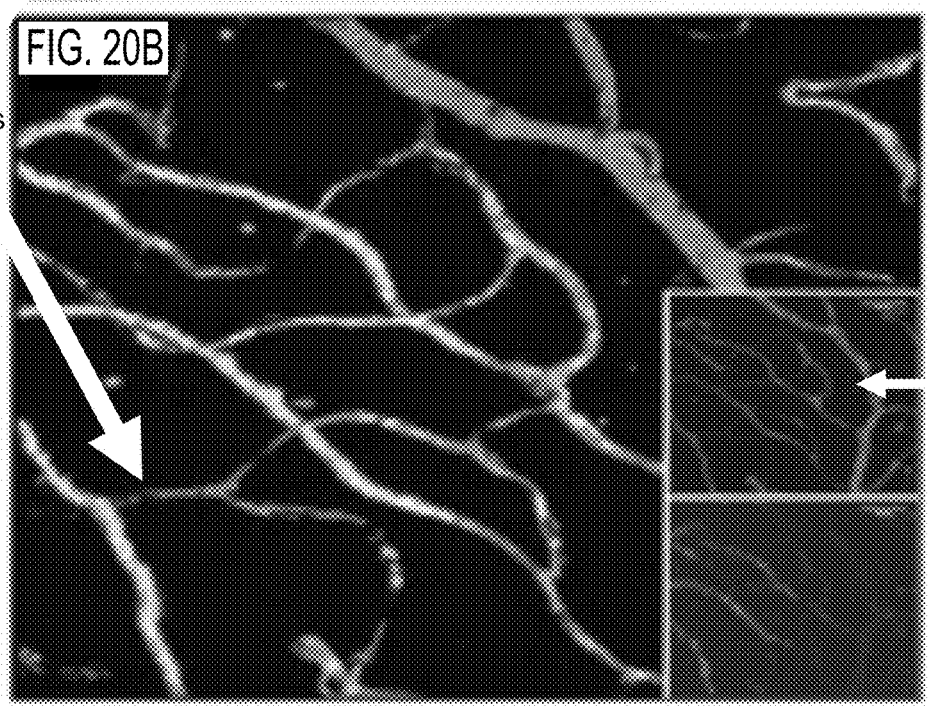
Figure 20F:
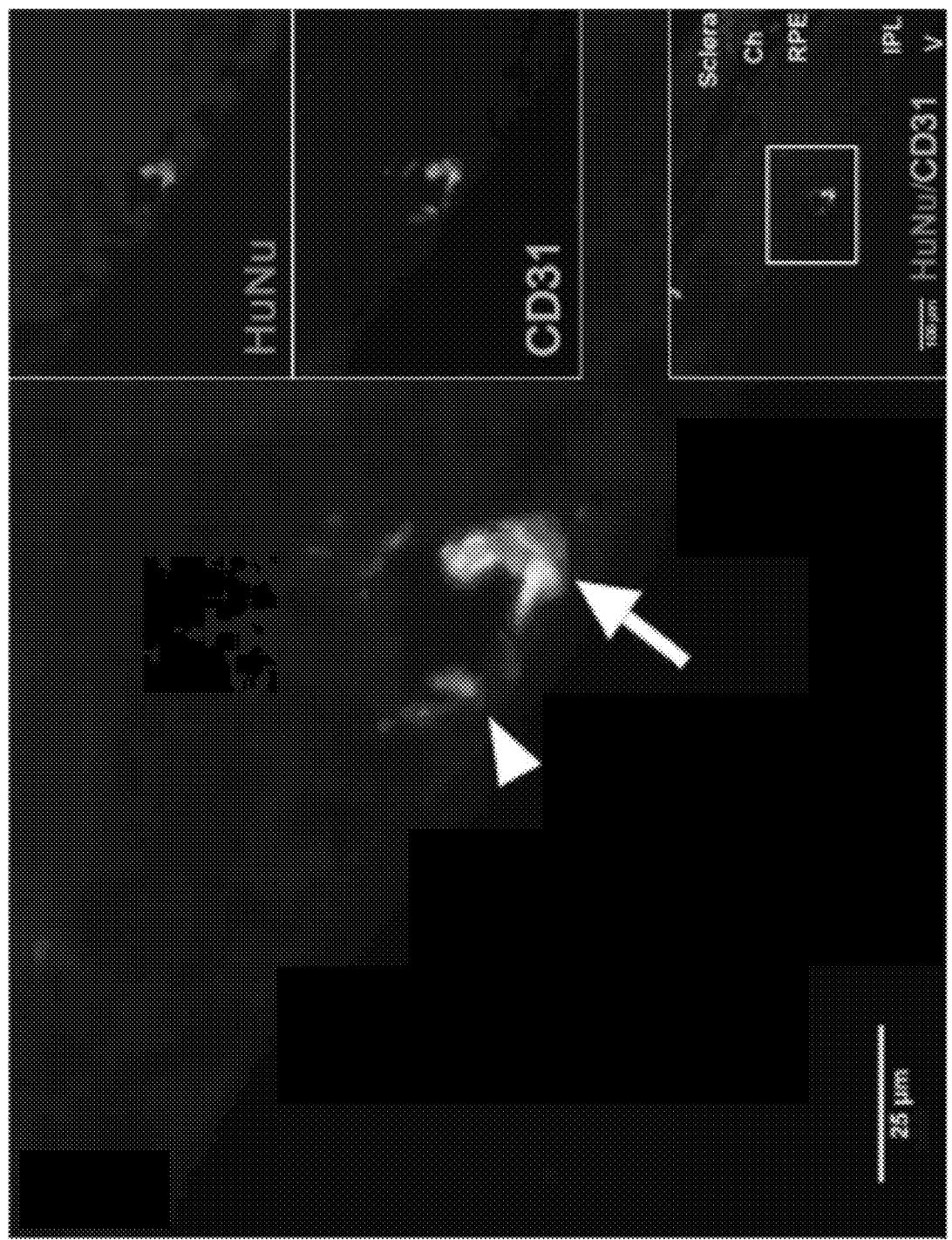

Fluorescent immunocytochemistry colocalizes hemangioblast (hES-BC) cell-derived endothelial cells to existing injured vasculature in cross sections of mouse eyes that underwent I/R injury, and a representative cross section of a vessel in the ganglion cell layer in a retina from an injured eye is shown (FIG. 20f). Colocalization of human nuclear antigen staining with anti-CD31 staining of the vessel suggests that some endothelial cells in the vasculature were derived from hemangioblast (hES-BC) cells. FIG. 20f shows a high magnification view of a vascular lumen in the ganglion cell layer adjacent to the inner limiting membrane. The lumen is surrounded by endothelial cells (FIG. 20f, arrowhead, CD31) and also by mature endothelial cell(s) derived from hemangioblast (hES-BC) cells (FIG. 20f, arrow, human nuclear antigen).

Methods.

For the in vivo ischemia/reperfusion studies, C57BL6/J mice (Jackson Laboratory) were age 7 to 10 weeks of age at the beginning of the study. The ischemia/reperfusion injury was induced by elevation of the intraocular pressure (IOP). Mice were kept under inhalation anesthesia (Isoflurane vapor) during induction of ischemia. The anterior chamber of the eye was cannulated with a 30-gauge needle attached to an infusion line of saline and the eye was subjected 2 h of hydrostatic pressure (80-90 mmHg measured by Tono Pen; Medtronic Solan, Jacksonville, Fla.) on the anterior chamber. This resulted in retinal ischemia as confirmed by whitening of the iris and loss of the red reflux. After 120 minutes the needle was withdrawn and the IOP was normalized, resulting in reperfusion injury. The contralateral eye served as a control.

Seven days following retinal ischemia reperfusion injury, the mice were injected either systemically via retro-orbital sinus (n=13) or injected intravitreally (n=4) with fluorescently labeled hemangioblasts collected from day 6 hES-BCs. Fluorescent vital labeling of hemangioblasts was accomplished using the dye PKH-67 (Sigma-Aldrich™) according to manufacturer's guidelines. For systemic injection each mouse received $4 \times 10^5$ labeled hemangioblasts in 100 µl, while for intravitreal injection each mouse received $5 \times 10^4$ hemangioblasts in 2 µl. The contralateral control eye of the intravitreous injection group was injected with an equivalent volume of sterile isotonic saline. One day later the mice were euthanized and the eyes removed and fixed in 4% paraformaldehyde for 1 h. After washing, the eyes were dissected by a circumferential limbic incision to remove the cornea and lens, followed by the vitreous humor. The intact neural retina was next removed by gently detaching it from the underlying choroid. The intact retina was placed in permeabilization buffer. The retinas were isolated and incubated overnight at 4° C. in 1:1000 Rhodamine-conjugated *R. communis* agglutinin I(Vector Laboratories) in 10 mM HEPES, 150 mM NaCl and 0.1% Tween 20 (pH 7.5). After 24 h, the retinas were washed in 10 mM HEPES and 150 mM NaCl at for 24 h at 4° C. and then mounted on coverslips for imaging using an MRC-1024 Confocal Laser Scanning Microscope (BioRad) at the Optical Microscopy Facility at the University of Florida (Gainesville). Alternatively, a Zeiss laser scanning confocal microscope was used to image the retinas.

For microscopy using the Zeiss laser scanning microscope, the retinas were placed on glass coverslips and their curvature was flattened by 4 or 5 radial incisions extending from the ciliary margin to within 1 mm of the optic disc. Simultaneous red and green fluorescence digital image captures of the mounted retinas were then made with a Zeiss laser scanning confocal microscope using either a 10× or 20× objective. The z-section depth was kept constant at 2 µm, and the entire retinal vasculature through the thickness of the neural retina (which includes the superficial, mid, and deep vascular plexi) was scanned, resulting in typically 25-35 z-section images per fluorescent channel. Image captures were made from random locations in the mid-periphery of the retinas as these areas are where the most vascular damage is typically observed in these models. The 3-dimensional z-stacks were then flattened using ImageJ software (ImageJ 1.37c, Wayne Rasband, National Institutes of Health, USA, http://rsb.info.nih.gov/ij/index.html) so that the three vascular plexi are visible in a single 2-dimensional plane.

A second set of mice (n=6) that were also subjected to I/R injury in the right eye received approximately $2\times10^5$ PKH-67-labeled hES-BCs or hemangioblasts in 100 µl administered by left retro-orbital sinus injection. Mice were euthanized at 2 days and 7 days (n=3 each) post injury and perfused with 3-5 ml TRITC-conjugated dextran (Sigma-Aldrich®, St. Louis, Mo., 5 mg/ml) in 4% buffered paraformaldehyde via left ventricular puncture. Eyes were then removed, dissected, and the retinas mounted flat for digital image capture by confocal microscopy as described earlier. The contralateral (uninjured) eye served as the control. This perfusion fixation method allows the visualization of patent vessels, as only functional vessels can be perfused.

Example 6: In Vivo Repair in a Diabetes Model

In vivo repair was also studied in spontaneously diabetic obese BBZDR/Wor rats with Type II diabetes of greater than 3 months. These rats develop many characteristics of pre-proliferative diabetic retinopathy including acellular capillaries and endothelial dysfunction, pericyte loss, and blood retinal barrier breakdown (Shi et al. 1998 *Blood* (92): 362-367; Asahara et al. 1997 *Science* (275): 964-967; Kalka et al. 2000 *Circ. Res.* (86): 1198-1202; Murohara et al. 2000 *J. Clin. Invest.* (105): 1527-1536; Urbich et al. 2004 *Trends Cardiovasc. Med.* (14): 318-322).

Male obese type 2 diabetic BBZDR/Wor rats (Biomedical Research Models, Worcester, Mass.) with duration of diabetes of at least 3 months, along with lean age- and sex-matched controls, were used to examine the ability of BCs to participate in reendothelialization of damaged capillaries. Rats were immune suppressed by intramuscular injection of cyclosporine (2 mg/Kg/day) beginning one day prior to administering the cells, and continuing for the duration of the study. hES-EBc were pelleted by centrifugation and resuspended in sterile saline at a concentration of $3\times10^4/\mu l$; 5 µl of that suspension was injected into each eye of each of six diabetic and control rats. The animals were euthanized 2 days (n=3 diabetic, n=3 control) and 7 days (n=3 diabetic, n=3 control) after administering the hES-BCs. Four of the six eyes from each treatment group were processed and retinal flatmounts were prepared as described for the mouse I/R study using rhodamine-conjugated *R. communis* to visualize vessels. The rat retinas were additionally reacted with monoclonal anti-GFP (Chemicon™, Temecula, Calif.; 1:250 in PBS) followed by FITC-conjugated goat anti-mouse IgG (Abcam™, Cambridge, Mass.; 1:200 in PBS) to visualize the GFP-expressing BCs. Digital image captures were performed by confocal microscopy as described for the mouse I/R study.

The remaining two eyes from each treatment group were fixed, dehydrated in 2.5M sucrose, and then embedded in OCT medium for cryosectioning. At least 50 sections (10 µm thickness, every 10th section kept) were collected and reacted (with appropriate washes between incubations) with monoclonal rat anti-CD31 (Abcam™, 1:100 in PBS), rabbit antihuman vWF (Sigma-Aldrich™, 1:200 in PBS), and 1:50 biotinylated anti-human nuclear antigen, followed by FITC-conjugated anti-rat IgG (Sigma-Aldrich®, 1:320 in PBS) and AMCA-conjugated goat anti-rabbit IgG (Vector Laboratories™, Burlingame, Vt., 1:75 in PBS), and finally Texas red-conjugated streptavidin (Vector Laboratories, 1:500 in PBS). The sections were then mounted with Vectashield antifade medium (Vector Laboratories™) and digital image captures were made with a Zeiss Axioplan 2 epifluorescence microscope coupled to a Spot CCD camera.

As in the I/R mouse model, intravitreally administered hES-BC cells (hemangioblasts) incorporated extensively into areas with both larger and smaller (FIGS. 21a and 21b) vasculature. FIG. 20b also reveals a large vessel that is nearly all green and narrows very rapidly (light gray vessel on the top right of FIG. 21b). These "pinched-off" vessels are characteristic of pre-proliferative diabetic retinopathy, where microthrombi result in vessel degeneration and downstream ischemia. Small vessels that continue from and branch extensively from this pinched larger vessel show a high degree of incorporation of green BC cells (shown as light gray in FIG. 21). By contrast, no green hES-BC cells colocalized with resident vessels in eyes from the non-diabetic control animal. Eyes from the non-diabetic control animal confirm that the BC cells do not incorporate into the uninjured vasculature but rather remain as sheets atop the retina after intravitreal administration of hES-BC cells (FIG. 21c, light gray area).

Immunohistochemical analysis showed colocalized staining with CD31 and human nuclear antigen in cells lining vessel lumens in the ganglion cell layer of the diabetic rat retinas (FIGS. 21e and 21f), immediately posterior to the internal limiting membrane that separates the neural retina from the vitreous. This anatomical location is the site of the superficial retinal vascular plexus and is the typical location of vascular pathology in diabetes. This precise localization and robust incorporation clearly demonstrates that hemangioblasts participate in repair of vessels that are involved in diabetic retinopathy. Most sections showed vessels with clearly visible lumens whose peripheries were lined with cells staining for both endothelial (CD31) and human nuclear antigen markers (FIGS. 21e and 21f, arrows), whereas there was no evidence of hemangioblast (hES-BC) cell incorporation in the non-diabetic control rat eyes that were also injected with BC cells (FIG. 21d, arrows).

Example 7: In Vivo Repair in a Murine Hind Limb Ischemic Model

The ability of BC cells to generate vascular endothelial cells was also examined in a murine hind limb ischemic model. The experiments were performed on 8- to 12-week-old (20~30 g) NOD-SCID β2 mice (Jackson Laboratory). Ischemia of the right hind limb was induced by femoral artery ligation surgery, and hemangioblast (hES-BC) cells ($6 \times 10^5$ hES-BC cells) or cell free medium were injected into the area of peri-ischemic muscle immediately following the surgery.

To demonstrate physiological functions of injected hemangioblast (hES-BC) cells, right ischemic hind limb blood flow was monitored for 4 weeks and compared with blood flow of the left normal hind limb. An immunofluorescent technique was used to detect human specific vWF (R and D System™, MN) and to identify blood vessel endothelial cells from engrafted hemangioblast (hES-BC). A secondary antibody conjugated with Alexa Fluor 594 was used. For blood flow analysis, laser Doppler blood-flow imaging was used to asses the blood flow in mice before (day 0) and after (day 3 to 30) femoral artery ligation, and blood flow rate is calculated as the ratio of flow in the ischemic limb to that in the non-ischemic limb.

As shown in FIGS. 22f and 22g, hemangioblast (hES-BC) cells significantly enhanced the restoration of blood flow rate in ischemic limbs as compared to medium control ($p<0.0001$). Improvement persisted for four weeks until near normal flow rates were achieved.

Four weeks after injection of hES-blast colony cells into the peri-ischemic muscle, the animals were sacrificed and immunostained for human specific vWF. Intra-muscular areas were identified containing positive staining of human specific vWF cells showing vascular organization (FIG. 22 d-e). Control tissue from infarcted muscle injected with cell free medium showed no human vWF staining (FIG. 22c).

Example 8: In Vivo Repair in a Murine Myocardial Infarct Model

In a series of experiments in the murine myocardial infarct (MI) model, myocardial infarction was induced in 8 to 12 week old (~20-30 gram) NOD/SICD β2 mice (Jackson Laboratory™) by ligation of the left coronary artery as described previously (Yang et al. 2002 J. Appl Physiol (93): 1140-1151). Fifteen minutes after MI induction, $3 \times 10^5$ GFP− hemangioblast (hES-BC) cells derived from H1-GFP hES cells or cell free medium were transplanted into the ischemic and peri-ischemic myocardium. The experimental protocol was approved by the Animal Care Committee of Memorial Sloan-Kettering Cancer Center. Thirty days post hemangioblast (hES-BC) cell injection, 71% ($^{12}/_{17}$) of the animals injected with hemangioblast (hES-BC) cells survived as compared to 42% ($^{8}/_{19}$) animals injected with medium control (FIG. 22h, P<0.002).

Animals were sacrificed four weeks after injection of hemangioblast (hES-BC) cells into ischemic and peri-ischemic myocardium and the hearts were quickly removed and washed in PBS. The hearts were embedded in tissue freezing medium (Fisher Scientific™, NJ). Frozen tissue was sectioned to 10-μm slides.

Infarcted tissue recovered for immunostaining demonstrated that areas of regenerating tissue contained considerable numbers of endothelial cells staining specifically for human vWF. Confocal microscopy confirmed the incorporation of human specific vWF− positive endothelial cells into the lumen of microvessels in the infarcted tissue (FIG. 22i). These cells were closely associated but had not yet formed highly organized vascular tissue (FIG. 22b). No human vWF positive cells were detectable in infarcted heart tissue from control mice (FIG. 22a).

The transplanted hemangioblast (hES-BC) cells also gave rise to cardial myocytes. To identify regenerated myocytes from engrafted hemangioblast (hES-BC) cells, a double immunofluorescent staining technique was used to detect GFP that expressed only in human cells derived from H1-GFP hES cells (Santa Cruz Biotechnology Inc.™, CA) and cTnI, a cardiomyocyte marker (Santa Cruz Biotechnology Inc.™, CA). A secondary antibody conjugated with Alexa Fluor 488 for GFP or Alexa Fluor 594 for TnI was used. Images were taken under fluorescent microscopy. N=3. FIG. 23 shows immunostaining of GFP (brightest or lightest stained areas) and cTnI (medium gray areas) on MI mice; cells stained positive for both GFP and cTnI are cardiomyocytes derived from injected hES=BC cells (FIG. 23, magnification 200×). The arrows indicate double positive staining cells derived from injected hES-BC cells.

The results from Examples 7 and 8 demonstrate that hemangioblast cells reduce mortality after myocardial infarction and restore blood flow to near normal level in ischemic hind limbs.

Example 9: Hemangioblasts or hES-BC Cells can Give Rise to Smooth Muscle Cells In Vitro The hemangioblasts, or hES-BC cells, of the present invention can also differentiate into smooth muscle cells, and thus, in certain embodiments, may be pluripotent.

To examine gene expression in the hemangioblast (hES-BC) cells, cells were handpicked under dissection microscope at day 6 and total RNA was isolated. Using an RNAeasy Micro Kit (Qiagen™), the RNA was subjected to first strand cDNA synthesis with SMART II and CDS primers (Clontech™), using Superscript III reverse transcriptase (Invitrogen™), and cDNA pools were constructed using the SMART cDNA synthesis kit (Clontech™). Smooth muscle gene expression pattern was analyzed using primers specific for smooth muscle calponin (CNN1), SM22, smooth muscle actin (α-SMA) and GAPDH (quality control) by PCR. Total RNA from human aorta smooth muscle cells (AoSM) was used as a positive control, and mouse fibroblast 3T3 total RNA was used as a negative control. PCR products were separated on a 1% agarose gel and exposed by ethidium bromide fluorescence.

Figure 24A:
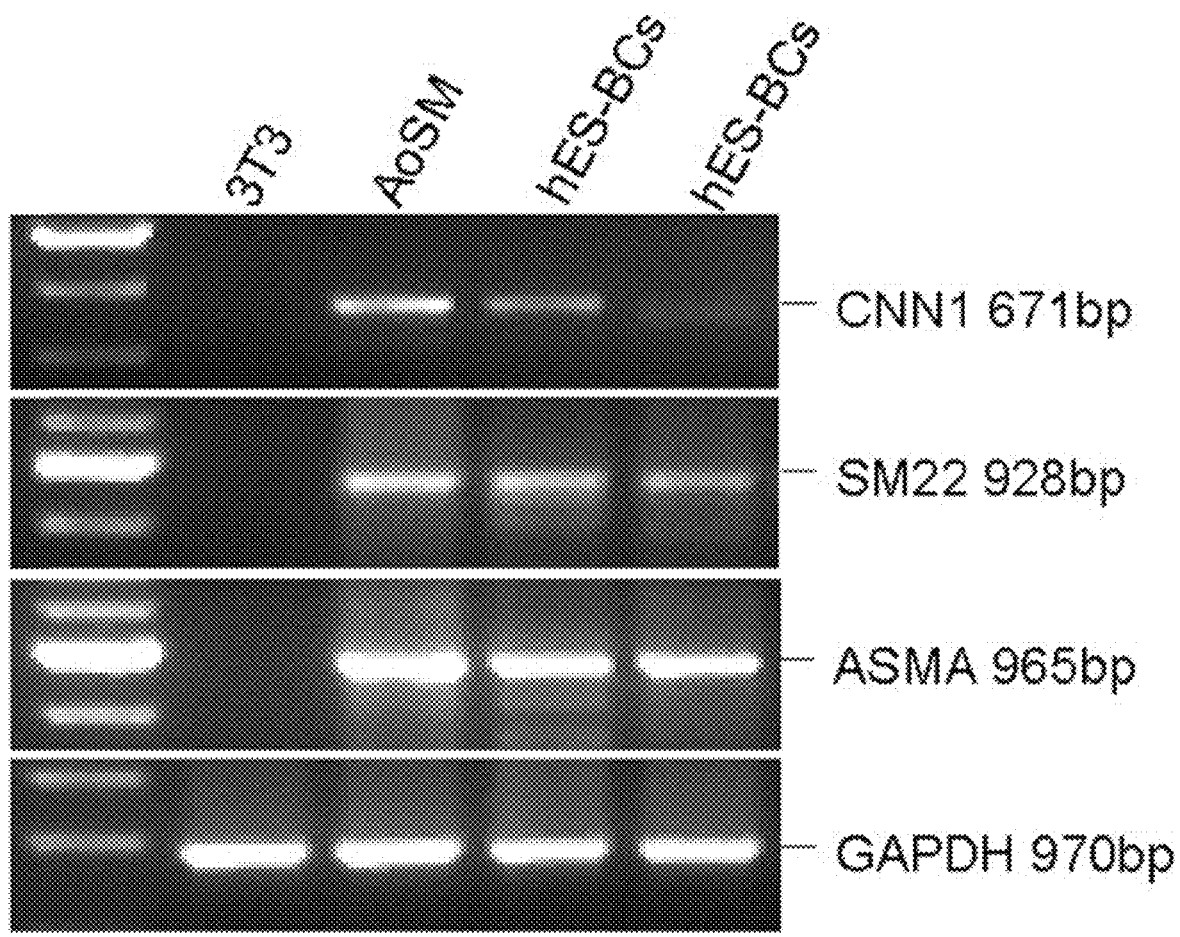
FIGS. 24A-24B illustrate differentiation of hemangioblast (hES-BC) cells into smooth muscle cells. 24A Hemangioblasts express smooth muscle specific genes as determined by PCR of RNA isolated from hemangioblasts (hES-BCs). 24B The hemangioblasts (hES-BCs) also differentiate into smooth muscle cells in vitro. Immumostaining for calponin and α-SMA shows that differentiated cells express these two smooth muscle cell markers.
Figure 24B:
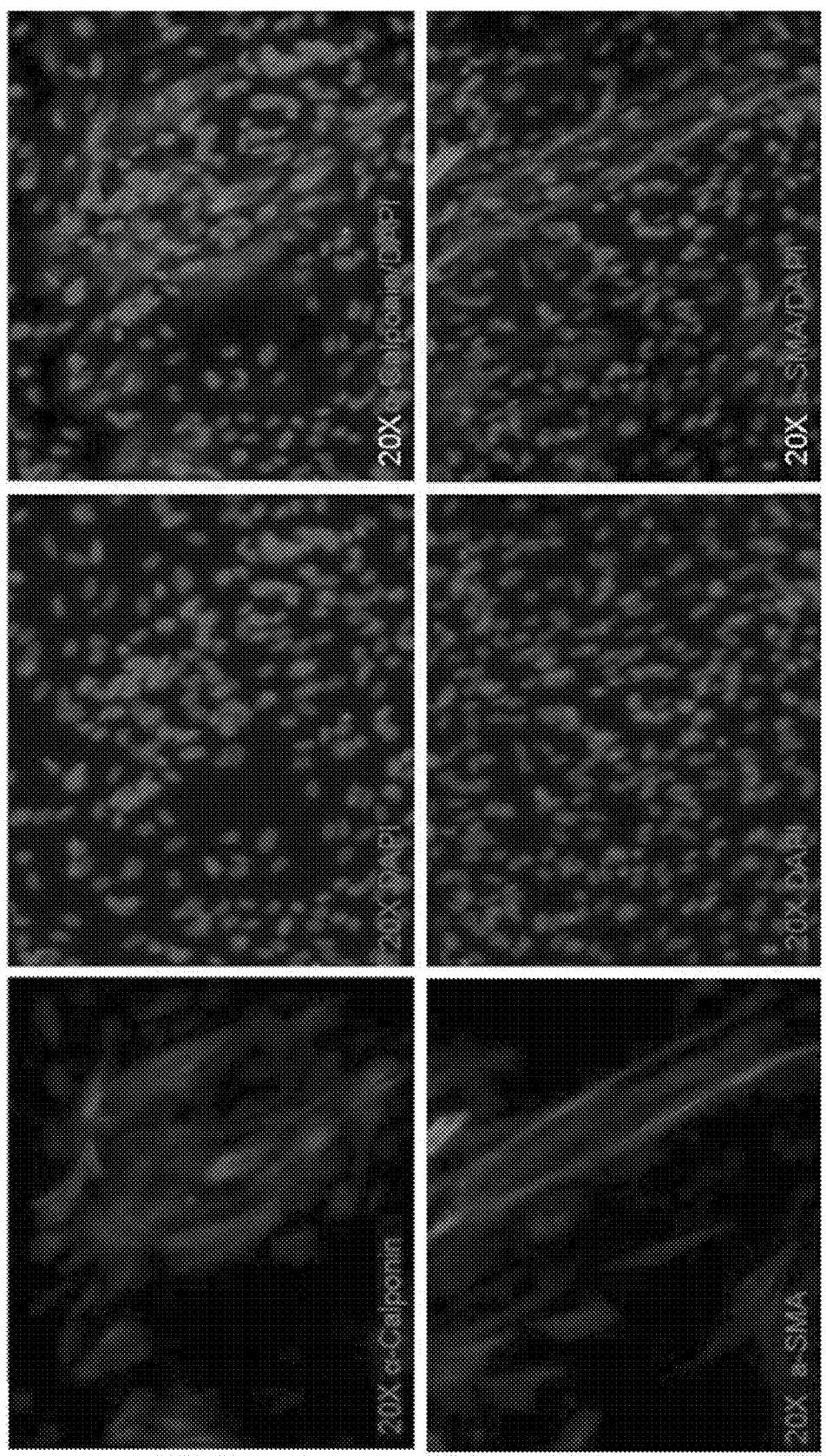

FIG. 24 shows that hemangioblast (hES-BC) cells express smooth muscle specific genes CNN1, α-SMA and SM22.

To derive smooth muscle cells from the hemangioblasts of the present invention, purified hemangioblast (hES-BC) cells were plated on fibronectin-coated culture slides (BD Bioscience™) in Smooth Muscle Medium (Lonza™) and differentiation was induced for 2-9 days. Cells were then fixed with 4% paraformaldehyde for 15 min, washed with 1×PBS and permeabilized with 0.4% Triton X100. For detecting the expression of smooth muscle proteins, the permeabilized cells were incubated with primary antibodies against calponin (CNN1) and α-SMA (Dako) at 4° C. overnight, then followed by Rhodamine labeled secondary antibodies and examined under fluorescent microscope.

The results presented in FIG. 24 clearly demonstrate that some hemangioblast (hES-BC) cells give rise to CNN1 and α-SMA positive smooth muscle cells after in vitro differentiation under the above conditions.

Example 10: Induction of Immunological Tolerance in Transplant Recipients in a Mouse Model System Human hemangioblast cells generated and expanded according to the methods of the present invention may be used to induce donor-specific tolerance in transplant recipients. Hemangioblasts or derivative hematopoietic stem cells can engraft in unconditioned recipients when the cells are given in large numbers. The ability of hemangioblasts to engraft and produce chimerism may be tested in the immunocompromised NOD/SCID-Tg mouse model system in which mice have been reconstituted with human immune cells. Immunodeficient NOD/SCID-Tg mice can be treated with whole body irradiation and injected with human donor hemangioblasts on the same day. Human fetal thymus and fetal liver fragments are implanted under the kidney capsule of mice to achieve human lymphopoiesis and reconstitution of the human immune system. The implanted human thymus and liver fragments are mismatched with respect to the human donor hemangioblasts. The mice can then be tested for tolerance to grafts matched to the human hemangioblasts as compared to tolerance to third party, non-matched grafts.

In order to optimize engraftment, thymic space may be induced by the administration of thymic irradiation. In the mouse model, recipient mice can receive anti-T cell mAbs such as anti-CD4 and anti-CD8 mAbs, 7 Gy thymic irradiation on day 0, and human hemangioblasts on days 0 through 4.

To evaluate tolerance, mixed lympyhocyte reactions and cell mediated lympholysis studies may be Additionally, human hemangioblasts can be substituted for the human fetal liver fragments in the method described above in order to test the ability of the hemangioblasts to induce chimerism in the hu-SCID mouse or similar model system.

Example 11: Induction of Immunological Tolerance in Transplant Recipients

In humans, tolerance may be achieved using the large numbers of human hemangioblasts generated and expanded or expanded by the methods of the present invention.

Peripheral chimerism may be achieved through the large numbers of hemangioblasts without the need for whole body irradiation. However, to achieve central deletional tolerance, it may be optimal to create space in the thymus in order to allow high levels of intrathymic chimerism to develop. Space in the thymus can be achieved by specific irradiation or by the use of multiple administrations of anti-T cell antibodies or with drugs that deplete the thymus.

The following procedure is designed to lengthen the time an implanted organ, tissue, or cell survives in a patient (graft survival) and to decrease the level of immunosuppression required in transplantation procedures. The organ can be any organ, e.g., a liver, a kidney, a pancreas, or a heart. Tissue can be any type of tissue, such as skin, bone, corneas, tendons, ligaments, heart valves, etc. Cells or cell therapies include, but are not limited to, hematopoietic cells (such as, for example, mesenchymal stem cells as a treatment for ischemia or other cells for the treatment of hematologic disorders), pancreatic cells such as insulin-secreting pancreatic beta-cells for the treatment of diabetes mellitus, retinal pigment epithelium cells for the treatment of macular degeneration, and cell-based therapies for the treatment of neurological disorders.

The method may include one or more of the following steps: inactivation of recipient T cells or costimulatory blockade; inactivation of recipient NK cells; transplantation of tolerance-inducing cells, e.g., human hemangioblasts; optionally, the implantation of donor stromal tissue or administration of human cytokines; and the administration of thymic irradiation. The combination of a sufficiently large number of donor human hemangioblasts in combination with thymic irradiation and/or T cell costimulatory blockade significantly reduces or eliminates the need for whole body irradiation. The method may include any or all of these steps, and the steps may be carried out in the following sequence.

First, a preparation of horse anti-human thymocyte globulin (ATG) or other depleting anti T cell depleting agent is intravenously injected into the recipient. The antibody preparation eliminates mature T cells. If not eliminated, mature T cells could promote rejection of both the human hemangioblast cells or hematopoietic stem cells derived therefrom, and, after sensitization, the graft itself. The ATG preparation also eliminates natural killer (NK) cells. NK cells probably have no effect on the implanted organ, but may act immediately to reject the newly introduced human hemangioblast cells.

The presence of donor antigen in the recipient thymus during the time when recipient T cells are regenerating post-transplant is critical for tolerizing recipient T cells. If donor human hemangioblasts are not able to become established in the recipient thymus and induce tolerance before recipient T cells regenerate, repeated doses of anti-recipient T cell antibodies may be necessary throughout the non-myeloablative regimen. Continuous depletion of recipient T cells may be required for several weeks.

The second step in the non-myeloablative procedure may be to supply specific growth factors or cytokines, to promote engraftment of donor human hemangioblast or stem cells.

Human hemangioblast cells of the donor (or that are matched to the donor) may then be injected into the recipient. Donor cells home to appropriate sites of the recipient and grow contiguously with remaining recipient's cells and proliferate, forming a chimeric lymphohematopoietic population. By this process, newly forming B cells (and the antibodies they produce) are exposed to donor antigens, so that the transplant will be recognized as self.

Tolerance to the donor is also observed at the T cell level in recipients in which human hemangioblast or derived hematopoietic stem cells engraftment has been achieved. When a matched organ graft is placed in such a recipient several months after hematopoietic or bone marrow chimerism has been induced, the graft should be accepted by both the humoral and the cellular arms of the immune system. This approach has the added advantage of permitting organ transplantation to be performed sufficiently long after transplant of donor human hemangioblast cells such that the normal health and immunocompetence of the recipient patient will have been restored at the time of organ transplantation.

Many of the methods to create hematopoietic space utilize whole body irradiation, thereby promoting engraftment. The need for irradiation may be substantially reduced or eliminated by the administration of large numbers of donor hemangioblast cells. Administration of donor human hemangioblasts may be combined with a treatment, e.g., thymic irradiation, which induces thymic space, or T cell costimulatory blockade.

Finally, T cells, particularly, thymic or lymph node T cells, may be further suppressed by administering to the recipient a short course of an immunosuppressive agent, e.g., cyclosporine or similar agent To evaluate tolerance, mixed lympyhocyte reactions and cell mediated lympholysis studies may be performed in recipients.

While any of these procedures may aid the survival of an implanted organ, tissue, or cell, best results may be achieved when some or all of the steps are used in combination.

Example 12: Human RBC Transfusion

In order to confirm the viability and functionality of red blood cells (RBCs) produced by the methods of the invention, transfusions using human RBCs will be performed in NOD-scid mice. Mice will be splenectomized under Nembutal anesthesia one week prior to transfusion. Recipients will be bled immediately prior to transfusion to drop the hematocrit to 25%. Within one hour after bleeding, recipients will be transfused via i.v. injection with $6 \times 10^9$ human RBVs in 0.5 mL PBS. Cells from the initial transfusion will be labeled with carboxyfluorescein diacetate (CFSE) for fluorescent monitoring purposes. Transfusions will be repeated on day two and every four days thereafter. On day 1 post-transfusion and every four days thereafter for up to 4 weeks, recipient mice will be monitored by collecting 20 μL of blood from a tail nick with a heparinized capillary tube. The percentage of RBC and human RBC will be determined by microscopy and flow cytometry with FITC-anti-Fy6 antibody. The half-life of transplanted cells will be calculated. Expression of hemoglobin F will be determined to verify oxygen transport capacity of RBCs. It is expected that the RBCs will express hemoglobin F and have a half-life comparable to normally derived RBCs. It is therefore expected that the RBCs will be functional.

The present disclosure demonstrates that hemangioblasts, or human ES-BC cells, can be reliably derived and expanded under well-defined and reproducible conditions-representing an inexhaustible source of cells for patients with compromised vasculature. The concentration of these cells would not be limited by availability, but rather could be titrated to the precise clinical requirement of the individual. Repeated infusion of the identical cell population over the lifetime of the patient would also be possible if deemed necessary by the physician. Furthermore, the ability to create banks of matching or reduced-complexity HLA hES lines could potentially reduce or eliminate the need for immunosuppressive drugs and/or immunomodulatory protocols altogether.

This disclosure also demonstrates for the first time that hemangioblasts derived from embryonic stem cells can be used to achieve vascular repair in four different animal models. The formation of new blood vessels was rapid and robust, thus indicating that hES-derived hemangioblasts have robust reparative potential in vivo. These results also indicate that hemangioblasts may be used to restore vascularization and function in patients with vascular disease. Adoptive transfer of endothelial precursor cells such as hemangioblasts may therefore be useful in restoring blood flow and increasing capillary density, decreasing limb loss and facilitating recovery from myocardial injury.

This disclosure further provides methods for generating differentiated cell types for use in transfusion. For example, this disclosure provides methods for generating red blood cells for use in transfusion. In certain embodiments, the red blood cells express hemoglobin F.

All experiments were performed in accordance with the protocol approved by the Animal Care and Use Committee of The University of Florida and the tenets of the ARVO Statement for the Use of Animals in Ophthalmic and Vision Research.

```
SEQUENCE LISTING
(Human HOXB4 amino acid sequence - Genbank
Accession No: GI: 13273315)
                                                   SEQ ID NO: 1
   1 mamssflinsnyvdpkfppceeysqsdylpsdhspgyyaggqrressfqpeagfgrraac 61 tvqryaacrdpgpppppppppppppppglsprapapppagallpepgqrceavssspppp 121 pcaqnplhpspshsackepvvypwmrkvhvstvnpnyaggepkrsrtaytrqqvleleke 181 fhynryltrrrrveiahalclserqikiwfqnrrmkwkkdhklpntkirsggaagsaggp 241 pgrpnggpral (Human HOXB4 DNA sequence - Genbank Accession
No: GI: 85376187)
                                                   SEQ ID NO: 2
   1 GGAAAACGAGTCAGGGGTCGGAATAAATTTTAGTATATTTTGTGGGCAATTCCCAGAAAT

61 TAATGGCTATGAGTTCTTTTTTGATCAACTCAAACTATGTCGACCCCAAGTTCCCTCCAT

121 GCGAGGAATATTCACAGAGCGATTACCTACCCAGCGACCACTCGCCCGGGTACTACGCCG

181 GCGGCCAGAGGCGAGAGAGCAGCTTCCAGCCGGAGGCGGGCTTCGGGCGGCGCGCGGCGT

241 GCACCGTGCAGCGCTACGCGGCCTGCCGGGACCCTGGGCCCCGCCGCCTCCGCCACCAC

301 CCCCGCCGCCCCCGCCACCGCCCGGTCTGTCCCCTCGGGCTCCTGCGCCGCCACCCGCCG

361 GGGCCCTCCTCCCGGAGCCCGGCCAGCGCTGCGAGGCGGTCAGCAGCAGCCCCCGCCGC

421 CTCCCTGCGCCCAGAACCCCCTGCACCCCAGCCCGTCCCACTCCGCGTGCAAAGAGCCCG
```

-continued
```
 481 TCGTCTACCCCTGGATGCGCAAAGTTCACGTGAGCACGGTAAACCCCAATTACGCCGGCG
 541 GGGAGCCCAAGCGCTCTCGGACCGCCTACACGCGCCAGCAGGTCTTGGAGCTGGAGAAGG
 601 AATTTCACTACAACCGCTACCTGACACGGCGCCGGAGGGTGGAGATCGCCCACGCGCTCT
 661 GCCTCTCCGAGCGCCAGATCAAGATCTGGTTCCAGAACCGGCGCATGAAGTGGAAAAAAG
 721 ACCACAAGTTGCCCAACACCAAGATCCGCTCGGGTGGTGCGGCAGGCTCAGCCGGAGGGC
 781 CCCCTGGCCGGCCCAATGGAGGCCCCCGCGCGCTCTAGTGCCCCCGCACGCGGGAGCCAC
 841 GAACCTCGGGGTGGGGGTGGGCAGTGAGTGCAGGGGATGGGGTGGGGGGACAGGAGGGGG
 901 CCCTGGGGCCTGGGCCCCGGAAAAATCTATCTGCCCTCCCCCACACTTTATATACGAATA
 961 AACGCAGAAGAGGGGGAGGGGAAGCTTTATTTATAGAAATGACAATAGAGGGCCACGGGG
1021 AGGCCCCCCCAGAAGCAAGATTCAAATCTCTTGCTTTCTTTCTTAAAAAAAAGAAAAAGA
1081 AAAAGCAAGAAGAAGGAAGAAAGAAAAAGACAGAAAGAGAAATAGGAGGAGGCTGCAGCT
1141 CCTCGTTTTCAGCTTTGGCGAAGATGGATCCACGTTTCATCTTTAATCACGCCAGGTCCA
1201 GGCCCATCTGTCTTGTTTCCTCTGCCAGGAGAAGACGGGCCTCGGTGGCGACCATTACC
1261 TCGACACCCGCTAACAAATGAGGCCCGGCTCGGCCGCCTCCGCCTCTGCTACTGCCGCTG
1321 CTGGAAGACAGCCTGGATTTCCTTTCTTTGTCCCCCACTCCCGATACCCAGCGAAAGCAC
1381 CCTCTGACTGCCAGATAGTGCAGTGTTTTGGTCACGGTAACACACACACACTCTCCCTCA
1441 TCTTTCGTGCCCATTCACTGAGGGCCAGAATGACTGCTCACCCACTTCCACCGTGGGGTT
1501 GGGGGTGGGCAACAGAGGAGGGGAGCAAGTAGGGAAGGGGTGGCCTTGACAACTCAGGA
1561 GTGAGCAGGAAAATTGAGTCCAAGGAAAAAGAGAGACTCAGAGACCCGGGAGGGCCTTCC
1621 TCTGAAAGGCCAAGCCAAGCCATGCTTGGCAGGGTGAGGGGCCAGTTGAGTTCTGGGAGC
1681 TGGGCACTACTCTGCCAGTCCAGAGTTGTACAGCAGAAGCCTCTCTCCTAGACTGAAAAT
1741 GAATGTGAAACTAGGAAATAAAATGTGCCCCTCCCAGTCTGGGAGGAGGATGTTGCAGAG
1801 CCCTCTCCCATAGTTTATTATGTTGCATCGTTTATTATTATTATTGATAATATTATTATT
1861 ACTATTTTTTGTGTCATGTGAGTCCTCTCTCCTTTTCTCTTTCTGACATTCCAAAACCA
1921 GGCCCCTTCCTACCTCTGGGGCTGCTTGAGTCTAGAACCCTTCGTATGTGTGAATATCTG
1981 TGTGCTGTACAGAGTGACAATAGAAATAAATGTTTGGTTTCTTGTGACCAGCAAAAAAAA
2041 AA
```

(Human HOXB4 amino acid sequence - Genbank
Accession No: GI: 29351568)

SEQ ID NO: 3
```
  1 mamssflinsnyvdpkfppceeysqsdylpsdhspgyyaggqrressfqpeagfgrraac
 61 tvqryaacrdpgppppppppppppppppglsprapapppagallpepgqrceavssspppp
121 pcaqnplhpspshsackepvvypwmrkvhvstvnpnyaggepkrsrtaytrqqvleleke
181 fhynryltrrrrveiahalclserqikiwfqnrrmkwkkdhklpntkirsggaagsaggp
241 pgrpnggpral
```

(Human HOXB4 DNA sequence - Genbank Accession
No: GI: 29351567)

SEQ ID NO: 4
```
  1 GGAAAACGAGTCAGGGGTCGGAATAAATTTTAGTATATTTTGTGGGCAATTCCCAGAAAT
 61 TAATGGCTATGAGTTCTTTTTTGATCAACTCAAACTATGTCGACCCCAAGTTCCCTCCAT
121 GCGAGGAATATTCACAGAGCGATTACCTACCCAGCGACCACTCGCCCGGGTACTACGCCG
181 GCGGCCAGAGGCGAGAGAGCAGCTTCCAGCCGGAGGCGGGCTTCGGCGGCGCGCGGCGT
241 GCACCGTGCAGCGCTACGCGGCCTGCCGGACCCTGGGCCCCGCCGCCTCCGCCACCAC
301 CCCCGCCGCCCCCGCCACCGCCCGGTCTGTCCCCTCGGGCTCCTGCGCCGCCACCCGCCG
```

```
 361 GGGCCCTCCTCCCGGAGCCCGGCCAGCGCTGCGAGGCGGTCAGCAGCAGCCCCCGCCGC

421 CTCCCTGCGCCCAGAACCCCCTGCACCCCAGCCCGTCCCACTCCGCGTGCAAAGAGCCCG

481 TCGTCTACCCCTGGATGCGCAAAGTTCACGTGAGCACGGTAAACCCCAATTACGCCGGCG

541 GGGAGCCCAAGCGCTCTCGGACCGCCTACACGCGCCAGCAGGTCTTGGAGCTGGAGAAGG

601 AATTTCACTACAACCGCTACCTGACACGGCGCCGGAGGGTGGAGATCGCCCACGCGCTCT

661 GCCTCTCCGAGCGCCAGATCAAGATCTGGTTCCAGAACCGGCGCATGAAGTGGAAAAAAG

721 ACCACAAGTTGCCCAACACCAAGATCCGCTCGGGTGGTGCGGCAGGCTCAGCCGGAGGGC

781 CCCCTGGCCGGCCCAATGGAGGCCCCCGCGCGCTCTAGTGCCCCCGCACGCGGGAGCCAC

841 GAACCTCGGGGTGGGGGTGGGCAGTGAGTGCAGGGGATGGGGTGGGGGACAGGAGGGGG

901 CCCTGGGGCCTGGGCCCCGGAAAAATCTATCTGCCCTCCCCCACACTTTATATACGAATA

961 AACGCAGAAGAGGGGGAGGGGAAGCTTTATTTATAGAAATGACAATAGAGGGCCACGGGG

1021 AGGCCCCCCCAGAAGCAAGATTCAAATCTCTTGCTTTCTTTCTTAAAAAAAAGAAAAAGA

1081 AAAAGCAAGAAGAAGGAAGAAAGAAAAAGACAGAAAGAGAAATAGGAGGAGGCTGCAGCT

1141 CCTCGTTTTCAGCTTTGGCGAAGATGGATCCACGTTTCATCTTTAATCACGCCAGGTCCA

1201 GGCCCATCTGTCTTGTTTCCTCTGCCGAGGAGAAGACGGGCCTCGGTGGCGACCATTACC

1261 TCGACACCCGCTAACAAATGAGGCCCGGCTCGGCCGCCTCCGCCTCTGCTACTGCCGCTG

1321 CTGGAAGACAGCCTGGATTTCCTTTCTTTGTCCCCCACTCCCGATACCCAGCGAAAGCAC

1381 CCTCTGACTGCCAGATAGTGCAGTGTTTTGGTCACGGTAACACACACACACTCTCCCTCA

1441 TCTTTCGTGCCCATTCACTGAGGGCCAGAATGACTGCTCACCCACTTCCACCGTGGGGTT

1501 GGGGGTGGGCAACAGAGGAGGGGAGCAAGTAGGGAAGGGGGTGGCCTTGACAACTCAGGA

1561 GTGAGCAGGGAAATTGAGTCCAAGGAAAAAGAGAGACTCAGAGACCCGGGAGGGCCTTCC

1621 TCTGAAAGGCCAAGCCAAGCCATGCTTGGCAGGGTGAGGGGCCAGTTGAGTTCTGGGAGC

1681 TGGGCACTACTCTGCCAGTCCAGAGTTGTACAGCAGAAGCCTCTCTCCTAGACTGAAAAT

1741 GAATGTGAAACTAGGAAATAAAATGTGCCCCTCCCAGTCTGGGAGGAGGATGTTGCAGAG

1801 CCCTCTCCCATAGTTTATTATGTTGCATCGTTTATTATTATTATTGATAATATTATTATT

1861 ACTATTTTTTGTGTCATGTGAGTCCTCTCTCCTTTTCTCTTTCTGACATTCCAAAACCA

1921 GGCCCCTTCCTACCTCTGGGGCTGCTTGAGTCTAGAACCCTTCGTATGTGTGAATATCTG

1981 TGTGCTGTACAGAGTGACAATAGAAATAAATGTTTGGTTTCTTGTGAAAAAAAAAAAAAA
```

(HIV TAT protein residues 47-57 conferring membrane translocation activity)

SEQ ID NO: 5

YGRKKRRQRRR (TAT PTD)

SEQ ID NO: 6

RKKRRQRRR (TAT PTD)

SEQ ID NO: 7

YARKARRQARR (TAT PTD)

SEQ ID NO: 8

YARAAARQARA (TAT PTD)

SEQ ID NO: 9

YARAARRAARR (TAT PTD)

SEQ ID NO: 10

RARAARRAARA

-continued

| | |
|---|---|
| (Antp PTD) | SEQ ID NO: 11 |

RQIKIWFQNRRMKWKK

| | |
|---|---|
| (HSV VP22 PTD) | SEQ ID NO: 12 |

DAATATRGRSAASRPTERPRAPARSASRPRRPVE

| | |
|---|---|
| (HeptaARG PTD) | SEQ ID NO: 13 |

RRRRRRR

| | |
|---|---|
| (TAT PTD) | SEQ ID NO: 14 |

YARAAARQARA

| | |
|---|---|
| (TAT PTD - multimer of three) | SEQ ID NO: 15 |

YARAAARQARAYARAAARQARAYARAAARQARA

| | |
|---|---|
| (sense primer for pTAT-HA-HoxB4) | SEQ ID NO: 16 |

TAC CTA CCC ATG GAC CAC TCG CCC

| | |
|---|---|
| (antisense primer for pTAT-HA-HoxB4) | SEQ ID NO: 17 |

TCG TGG CTC CCG AAT TCG GGG GCA

| | |
|---|---|
| (sense primer for modified pTAT-HA-HoxB4) | SEQ ID NO: 18 |

CGA TGG GGA TCC GGC TAC GCA CGC GCA GCT GCG CGC CAG

GCT CGC GCC GGT GGA TCC ACC ATG

| | |
|---|---|
| (antisense primer for modified pTAT-HA-HoxB4) | SEQ ID NO: 19 |

CAT GGT GGA TCC ACC GGC GCG AGC CTG GCG CGC AGC TGC

GCG TGC GTA GCC GGA TCC CCA TCG

---

What is claimed is:

1. A method for generating human embryonic stem cell-derived hemangio-colony forming cells in vitro, the method comprising:
   (a) culturing human embryonic stem cells in a serum-free media comprising vascular endothelial growth factor (VEGF) and bone morphogenic protein 4 (BMP—4) for promoting the formation of embryoid bodies;
   (b) culturing the cells produced in step (a) in a serum-free media comprising at least two growth factors selected from the group consisting of VEGF, BMP-4 and basic fibroblast growth factor (bFGF), thereby forming embryoid bodies;
   (c) disaggregating the embryoid bodies after step (b) into single cells; and
   (d) culturing the single cells in a serum free media comprising at least two growth factors selected from the group consisting of insulin, transferrin, granulocyte macrophage colony—stimulating factor (GM-CSF), interleukin-3 (IL-3), interleukin-6 (IL-6), granulocyte colony—stimulating factor (G-CSF), stem cell factor (SCF), thrombopoietin (TPO), FLT3 (FL), vascular endothelial growth factor (VEGF), and bone morphogenic protein 4 (BMP-4), thereby generating human hemangio-colony forming cells,
   wherein the human embryonic stem cell-derived hemangio-colony forming cells are capable of differentiating into hematopoidic cells and endothelial cells, and wherein the human embryonic stem cell-derived hemangio-colony forming cells express at least two markers selected from the group consisting of CD61, integrin β1 and NF-E2.

2. The method of claim 1, wherein the serum free media in step (b) or step (d) further comprises a HOXB4 protein.

3. The method of claim 1, wherein the serum free media of step (b) further comprises one or more growth factors selected from the group consisting of stem cell factor (SCF), Flt-3L (FL) thrombopoietin (TPO) and erythropoietin (EPO).

4. The method of claim 1, wherein the human embryonic stem cells are cultured in the serum free media comprising BMP-4 and VEGF in step (a) for at least the first 48 hours of cell culture.

5. The method of claim 3, wherein step (b) is performed within 48-72 hours of culturing the human embryonic stem cells in step (a).

6. The method of claim 1, wherein step (b) is performed within 48-72 hours of culturing the human embryonic stem cells in step (a).

7. The method of claim 1, wherein the serum free media of step (a), step (b) and step (d) further comprise erythropoietin (EPO).

8. The method of claim 1, further comprising purifying the human hemangio-colony forming cells.

9. The method of claim 8, wherein the purifying of the hemangio-colony forming cells comprises the use of immunoaffinity column chromatography with an anti-CD71 antibody.

10. The method of claim 1, further comprising isolating the human hemangio-colony forming cells.

11. The method of claim 10, wherein the isolating of the hemangio-colony forming cells comprises isolating the hemangio-colony forming cells by size and/or by morphology.

12. The method of claim 1, wherein step (d) is performed 72 hours after the initiation of culturing the human embryonic stem cells in step (a).

13. The method of claim 1, wherein the culturing in step (a), step (b) and step (d) is performed under low attachment conditions.

14. The method of claim 1, wherein the serum free media in step (d) further comprises methylcellulose.

15. The method of claim 1, wherein in step (a) the concentration of VEGF is 25-100 ng/ml, and the concentration of BMP-4 is 25-100 ng/ml.

16. The method of claim 3, wherein in step (b) the concentration of VEGF is 25-100 ng/ml, the concentration of BMP-4 is 25-100 ng/ml, the concentration of SCF is 10-50 ng/ml, the concentration FL is 10-50 ng/ml, and the concentration of TPO is 10-50 ng/ml.

17. The method of claim 1, wherein in step (d) the concentration of insulin is 10 μg/ml, the concentration of transferrin is 200 μg/ml, the concentration of GM-CSF is 20 μg/ml, the concentration of IL-3 is 20 ng/ml, the concentration of IL-6 is 10 ng/ml or 20 ng/ml, the concentration of G-CSF is 20 ng/ml, the concentration of SCE is 20 ng/ml or 50 ng/ml, the concentration of TPO is 20 ng/ml or 50 ng/ml, the concentration of FL is 20 ng/ml or 50 ng/ml, the concentration of VEGF is 25-100 ng/ml, and the concentration of BMP-4 is 25-100 ng/ml.

18. The method of claim 1, wherein the embryonic stem cells are from a library of embryonic stem cells that are hemizygous or homozygous for at least one major histocompatibility (MHC) allele present in a human population, and each member of the library is hemizygous or homozygous for a unique set of MHC alleles compared to other members of the library of embryonic stem cells, thereby generating a library of human hemangio-colony forming cells that are hemizygous or homozygous for at least one major histocompatibility (MHC) allele present in a human population, and each member of the library of human hemangio-colony forming cells is hemizygous or homozygous for a unique set of MHC alleles compared to other members of the library of human hemangio colony forming cells.

19. The method of claim 1, further comprising differentiating the hemangio-colony forming cells into human hematopoietic cells.

20. The method of claim 1, further comprising differentiating the hemangio-colony forming cells into human endothelial cells.

* * * * *

SEQUENCE LISTING

<160> NUMBER OF SEQ ID NOS: 19

<210> SEQ ID NO 1
<211> LENGTH: 251
<212> TYPE: PRT
<213> ORGANISM: Homo sapiens

<400> SEQUENCE: 1

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
                20                  25                  30

His Ser Pro Gly Tyr Tyr Ala Gly Gly Gln Arg Arg Glu Ser Ser Phe
            35                  40                  45

Gln Pro Glu Ala Gly Phe Gly Arg Arg Ala Ala Cys Thr Val Gln Arg
        50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
                85                  90                  95

Pro Pro Ala Gly Ala Leu Leu Pro Glu Pro Gly Gln Arg Cys Glu Ala
            100                 105                 110

Val Ser Ser Ser Pro Pro Pro Pro Cys Ala Gln Asn Pro Leu His
        115                 120                 125

Pro Ser Pro Ser His Ser Ala Cys Lys Glu Pro Val Val Tyr Pro Trp

```
                130                 135                 140
Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
                165                 170                 175

Leu Glu Lys Glu Phe His Tyr Asn Arg Tyr Leu Thr Arg Arg Arg Arg
                180                 185                 190

Val Glu Ile Ala His Ala Leu Cys Leu Ser Glu Arg Gln Ile Lys Ile
                195                 200                 205

Trp Phe Gln Asn Arg Arg Met Lys Trp Lys Lys Asp His Lys Leu Pro
210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
                245                 250

<210> SEQ ID NO 2
<211> LENGTH: 2042
<212> TYPE: DNA
<213> ORGANISM: Homo sapiens

<400> SEQUENCE: 2
ggaaaacgag tcaggggtcg gaataaattt tagtatattt tgtgggcaat tcccagaaat      60
taatggctat gagttctttt ttgatcaact caaactatgt cgaccccaag ttccctccat     120
gcgaggaata ttcacagagc gattacctac ccagcgacca ctcgcccggg tactacgccg     180
gcggccagag gcgagagagc agcttccagc cggaggcggg cttcgggcgg cgcgcggcgt     240
gcaccgtgca gcgctacgcg gcctgccggg accctgggcc ccgccgcct ccgccaccac     300 ccccgccgcc cccgccaccg cccggtctgt ccctcgggc tcctgcgccg ccacccgccg     360
gggccctcct cccggagccc ggccagcgct gcgaggcggt cagcagcagc ccccgccgc     420 ctccctgcgc ccagaacccc ctgcacccca gcccgtccca ctccgcgtgc aaagagcccg     480
tcgtctaccc ctggatgcgc aaagttcacg tgagcacggt aaaccccaat tacgccggcg     540
gggagcccaa gcgctctcgg accgcctaca cgcgccagca ggtcttggag ctggagaagg     600
aatttcacta caaccgctac ctgacacggc gccggaggt ggagatcgcc cacgcgctct     660
gcctctccga gcgccagatc aagatctggt tccagaaccg cgcatgaag tggaaaaaag     720 accacaagtt gcccaacacc aagatccgct cgggtggtgc ggcaggctca gccggagggc     780
cccctggccg gcccaatgga ggccccgcg cgctctagtg cccccgcacg cgggagccac     840
gaacctcggg gtgggggtgg gcagtgagtg caggggatgg ggtgggggga caggagggg     900 ccctggggcc tggccccgg aaaaatctat ctgccctccc ccacactta tatacgaata     960 aacgcagaag agggggaggg gaagctttat ttatagaaat gacaatagag ggccacgggg    1020 aggcccccc agaagcaaga ttcaaatctc ttgctttctt tcttaaaaaa aagaaaaaga    1080
aaaagcaaga agaaggaaga aagaaaaaga cagaaagaga aataggagga ggctgcagct    1140
cctcgttttc agctttggcg aagatggatc cacgtttcat ctttaatcac gccaggtcca    1200
ggcccatctg tcttgtttcc tctgccgagg agaaagacggg cctcggtggc gaccattacc    1260
tcgacacccg ctaacaaatg aggcccggct cggccgcctc cgcctctgct actgccgctg    1320
ctggaagaca gcctggattt cctttctttg tcccccactc ccgatacca gcgaaagcac    1380 cctctgactg ccagatagtg cagtgttttg gtcacggtaa cacacacaca ctctccctca    1440
```

```
tctttcgtgc ccattcactg agggccagaa tgactgctca cccacttcca ccgtgggtt      1500 gggggtgggc aacagaggag gggagcaagt agggaagggg gtggccttga caactcagga      1560
gtgagcagga aaattgagtc caaggaaaaa gagagactca gagacccggg agggccttcc      1620
tctgaaaggc caagccaagc catgcttggc agggtgaggg gccagttgag ttctgggagc      1680
tgggcactac tctgccagtc cagagttgta cagcagaagc ctctctccta gactgaaaat      1740
gaatgtgaaa ctaggaaata aaatgtgccc ctcccagtct ggaggagga tgttgcagag       1800 ccctctccca tagtttatta tgttgcatcg tttattatta ttattgataa tattattatt      1860
actatttttt tgtgtcatgt gagtcctctc tccttttctc tttctgacat tccaaaacca      1920
ggccccttcc tacctctggg gctgcttgag tctagaaccc ttcgtatgtg tgaatatctg      1980
tgtgctgtac agagtgacaa tagaaataaa tgtttggttt cttgtgacca gcaaaaaaaa      2040
aa                                                                     2042

<210> SEQ ID NO 3
<211> LENGTH: 251
<212> TYPE: PRT
<213> ORGANISM: Homo sapiens

<400> SEQUENCE: 3

Met Ala Met Ser Ser Phe Leu Ile Asn Ser Asn Tyr Val Asp Pro Lys
1               5                   10                  15

Phe Pro Pro Cys Glu Glu Tyr Ser Gln Ser Asp Tyr Leu Pro Ser Asp
                20                  25                  30

His Ser Pro Gly Tyr Tyr Ala Gly Gly Gln Arg Arg Glu Ser Ser Phe
            35                  40                  45

Gln Pro Glu Ala Gly Phe Gly Arg Arg Ala Ala Cys Thr Val Gln Arg
        50                  55                  60

Tyr Ala Ala Cys Arg Asp Pro Gly Pro Pro Pro Pro Pro Pro Pro Pro
65                  70                  75                  80

Pro Pro Pro Pro Pro Pro Gly Leu Ser Pro Arg Ala Pro Ala Pro
                85                  90                  95

Pro Pro Ala Gly Ala Leu Leu Pro Glu Pro Gly Gln Arg Cys Glu Ala
            100                 105                 110

Val Ser Ser Ser Pro Pro Pro Cys Ala Gln Asn Pro Leu His
            115                 120                 125

Pro Ser Pro Ser His Ser Ala Cys Lys Glu Pro Val Val Tyr Pro Trp
130                 135                 140

Met Arg Lys Val His Val Ser Thr Val Asn Pro Asn Tyr Ala Gly Gly
145                 150                 155                 160

Glu Pro Lys Arg Ser Arg Thr Ala Tyr Thr Arg Gln Gln Val Leu Glu
                165                 170                 175

Leu Glu Lys Glu Phe His Tyr Asn Arg Tyr Leu Thr Arg Arg Arg Arg
            180                 185                 190

Val Glu Ile Ala His Ala Leu Cys Leu Ser Arg Gln Ile Lys Ile
        195                 200                 205

Trp Phe Gln Asn Arg Arg Met Lys Trp Lys Lys Asp His Lys Leu Pro
210                 215                 220

Asn Thr Lys Ile Arg Ser Gly Gly Ala Ala Gly Ser Ala Gly Gly Pro
225                 230                 235                 240

Pro Gly Arg Pro Asn Gly Gly Pro Arg Ala Leu
                245                 250
```

```
<210> SEQ ID NO 4
<211> LENGTH: 2040
<212> TYPE: DNA
<213> ORGANISM: Homo sapiens

<400> SEQUENCE: 4
ggaaaacgag tcaggggtcg gaataaattt tagtatattt tgtgggcaat tcccagaaat      60
taatggctat gagttctttt ttgatcaact caaactatgt cgaccccaag ttccctccat     120
gcgaggaata ttcacagagc gattacctac ccagcgacca ctcgcccggg tactacgccg     180
gcggccagag gcgagagagc agcttccagc cggaggcggg cttcgggcgg cgcgcggcgt     240
gcaccgtgca gcgctacgcg gcctgccggg accctgggcc cccgccgcct ccgccaccac     300
ccccgccgcc cccgccaccg cccggtctgt ccctcgggc tcctgcgccg ccacccgccg     360
gggccctcct cccggagccc ggccagcgct gcgaggcggc cagcagcagc ccccgccgc     420 ctccctgcgc ccagaacccc ctgcacccca gcccgtccca ctccgcgtgc aaagagcccg     480
tcgtctaccc ctggatgcgc aaagttcacg tgagcacgg aaaccccaat tacgccggcg     540
gggagcccaa gcgctctcgg accgcctaca cgcgccagca ggtcttggag ctggagaagg     600
aatttcacta caaccgctac ctgacacggg gccgagggt ggagatcgcc cacgcgctct     660
gcctctccga gcgccagatc aagatctggt tccagaaccg gcgcatgaag tggaaaaaag     720
accacaagtt gcccaacacc aagatccgct cgggtggtgc ggcaggctca gccggagggc     780
cccctggccg gcccaatgga ggcccccgcg cgctctagtg ccccgcacg cgggagccac     840 gaacctcggg gtggggtgg gcagtgagtg caggggatgg ggtgggga caggaggggg     900 ccctgggcc tgggccccgg aaaaatctat ctgccctccc ccacactta tatacgaata     960 aacgcagaag agggggaggg gaagctttat ttatagaaat gacaatagag ggccacgggg    1020 aggcccccc agaagcaaga ttcaaatctc ttgctttctt tcttaaaaaa aagaaaaaga    1080
aaaagcaaga agaaggaaga aagaaaaaga cagaaagaga aataggagga ggctgcagct    1140
cctcgttttc agctttggcg aagatggatc cacgtttcat ctttaatcac gccaggtcca    1200
ggcccatctg tcttgtttcc tctgccgagg agaagacggg cctcggtggc gaccattacc    1260
tcgacacccg ctaacaaatg aggcccggct cggccgcctc cgcctctgct actgccgctg    1320
ctggaagaca gcctggattt cctttctttg tccccactc ccgataccca gcgaaagcac    1380
cctctgactg ccagatagtg cagtgttttg gtcacggtaa cacacacaca ctctccctca    1440
tctttcgtgc ccattcactg agggccagaa tgactgctca cccacttcca ccgtgggtt    1500 gggggtgggc aacagaggag gggagcaagt agggaagggg gtggccttga caactcagga    1560
gtgagcaggg aaattgagtc caaggaaaaa gagagactca gagacccggg agggccttcc    1620
tctgaaaggc caagccaagc catgcttggc agggtgaggg gccagttgag ttctgggagc    1680
tgggcactac tctgccagtc cagagttgta cagcagaagc ctctctccta gactgaaaat    1740
gaatgtgaaa ctaggaaata aaatgtgccc ctcccagtct gggaggagga tgttgcagag    1800
cctctctcca tagtttatta tgttgcatcg tttattatta ttattgataa tattattatt    1860
actatttttt tgtgtcatgt gagtcctctc tccttttctc tttctgacat tccaaaacca    1920 ggcccccttcc tacctctggg gctgcttgag tctagaaccc ttcgtatgtg tgaatatctg    1980
tgtgctgtac agagtgacaa tagaaataaa tgtttggttt cttgtgaaaa aaaaaaaaaa    2040

<210> SEQ ID NO 5
<211> LENGTH: 11
<212> TYPE: PRT
```

<213> ORGANISM: Human immunodeficiency virus

<400> SEQUENCE: 5

Tyr Gly Arg Lys Lys Arg Arg Gln Arg Arg Arg
1 5 10

<210> SEQ ID NO 6
<211> LENGTH: 9
<212> TYPE: PRT
<213> ORGANISM: Human immunodeficiency virus

<400> SEQUENCE: 6

Arg Lys Lys Arg Arg Gln Arg Arg Arg
1 5

<210> SEQ ID NO 7
<211> LENGTH: 11
<212> TYPE: PRT
<213> ORGANISM: Human immunodeficiency virus

<400> SEQUENCE: 7

Tyr Ala Arg Lys Ala Arg Arg Gln Ala Arg Arg
1 5 10

<210> SEQ ID NO 8
<211> LENGTH: 11
<212> TYPE: PRT
<213> ORGANISM: Human immunodeficiency virus

<400> SEQUENCE: 8

Tyr Ala Arg Ala Ala Ala Arg Gln Ala Arg Ala
1 5 10

<210> SEQ ID NO 9
<211> LENGTH: 11
<212> TYPE: PRT
<213> ORGANISM: Human immunodeficiency virus

<400> SEQUENCE: 9

Tyr Ala Arg Ala Ala Arg Arg Ala Ala Arg Arg
1 5 10

<210> SEQ ID NO 10
<211> LENGTH: 11
<212> TYPE: PRT
<213> ORGANISM: Human immunodeficiency virus

<400> SEQUENCE: 10

Arg Ala Arg Ala Ala Arg Arg Ala Ala Arg Ala
1 5 10

<210> SEQ ID NO 11
<211> LENGTH: 16
<212> TYPE: PRT
<213> ORGANISM: Drosophila melanogaster

<400> SEQUENCE: 11

Arg Gln Ile Lys Ile Trp Phe Gln Asn Arg Arg Met Lys Trp Lys Lys
1 5 10 15

<210> SEQ ID NO 12
<211> LENGTH: 34
<212> TYPE: PRT
<213> ORGANISM: human herpesvirus 1

<400> SEQUENCE: 12

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Arg Arg Arg Arg Arg
1               5

<210> SEQ ID NO 14
<211> LENGTH: 11
<212> TYPE: PRT
<213> ORGANISM: Human immunodeficiency virus

<400> SEQUENCE: 14

Tyr Ala Arg Ala Ala Ala Arg Gln Ala Arg Ala
1               5                   10

<210> SEQ ID NO 15
<211> LENGTH: 33
<212> TYPE: PRT
<213> ORGANISM: Human immunodeficiency virus

<400> SEQUENCE: 15

Tyr Ala Arg Ala Ala Ala Arg Gln Ala Arg Ala Tyr Ala Arg Ala Ala
1               5                   10                  15

Ala Arg Gln Ala Arg Ala Tyr Ala Arg Ala Ala Ala Arg Gln Ala Arg
            20                  25                  30

Ala

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tacctaccca tggaccactc gccc                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcgtggctcc cgaattcggg ggca                                          24

<210> SEQ ID NO 18

```
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgatggggat ccggctacgc acgcgcagct gcgcgccagg ctcgcgccgg tggatccacc    60
atg                                                                 63

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catggtggat ccaccggcgc gagcctggcg cgcagctgcg cgtgcgtagc cggatcccca    60
tcg                                                                 63
```